(12) United States Patent
You et al.

(10) Patent No.: US 9,839,690 B2
(45) Date of Patent: *Dec. 12, 2017

(54) SINGLET OXYGEN-LABILE LINKERS AND METHODS OF PRODUCTION AND USE THEREOF

(71) Applicant: The Board of Regents of the University of Oklahoma, Norman, OK (US)

(72) Inventors: Youngjae You, Edmond, OK (US); Moses Bio, Oklahoma City, OK (US); Abu Gafar Hossion, Oklahoma City, OK (US); Gregory Nkepang, Oklahoma City, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 15/187,227

(22) Filed: Jun. 20, 2016

(65) Prior Publication Data

US 2017/0014510 A1  Jan. 19, 2017

Related U.S. Application Data

(63) Continuation of application No. 14/396,802, filed as application No. PCT/US2013/038031 on Apr. 24, 2013, now Pat. No. 9,393,306.

(60) Provisional application No. 61/637,516, filed on Apr. 24, 2012, provisional application No. 61/674,552, filed on Jul. 23, 2012.

(51) Int. Cl.
| | |
|---|---|
| A61N 5/06 | (2006.01) |
| A61K 41/00 | (2006.01) |
| A61K 47/48 | (2006.01) |
| A61K 31/09 | (2006.01) |
| A61K 31/4745 | (2006.01) |
| A61K 49/00 | (2006.01) |
| A61N 5/10 | (2006.01) |

(52) U.S. Cl.
CPC .......... *A61K 41/0042* (2013.01); *A61K 31/09* (2013.01); *A61K 31/4745* (2013.01); *A61K 47/48069* (2013.01); *A61K 49/0006* (2013.01); *A61N 5/062* (2013.01); *A61N 5/10* (2013.01); *A61N 2005/0659* (2013.01); *A61N 2005/0662* (2013.01)

(58) Field of Classification Search
None
See application file for complete search history.

(56) References Cited

U.S. PATENT DOCUMENTS

| | | | |
|---|---|---|---|
| 6,331,530 B1 | 12/2001 | Breslow et al. | |
| 9,393,306 B2 * | 7/2016 | You ................... | A61K 41/0042 |
| 2004/0228831 A1 | 11/2004 | Belinka, Jr. et al. | |
| 2006/0105974 A1 | 5/2006 | Lange et al. | |
| 2008/0268061 A1 | 10/2008 | Jordan et al. | |

FOREIGN PATENT DOCUMENTS

| | | | |
|---|---|---|---|
| WO | 2009038776 A1 | 3/2009 | |
| WO | WO 2009038776 A1 * | 3/2009 | ....... A61K 47/48176 |

OTHER PUBLICATIONS

International Search Report and Written Opinion, dated Aug. 14, 2013, in PCT/US2013/038031, filed Apr. 24, 2013.
Bio, et al.; "Click and photo-unclick chemistry of aminoacrylate for visible light-triggered drug release"; Chem.Comm; 2012; vol. 48, pp. 6517-6519.
Bio, et al.; "Site-Specific and Far-Red-Light Activatable Prodrug of Combretastatin A-4 Using Photo-Unclick Chemistry"; Journal of Medicinal Chemistry; Apr. 30, 2013; vol. 56. pp. 3936-3942 and 16 pages of supporting information.
Hossion, et al.; "Visible Light Controlled Release of Anticancer Drug through Double Activation of Prodrug"; ACS Midecinal Chemistry Letters; Nov. 21, 2012, vol. 4, pp. 124-127.
Jiang, et al. Site-Specific Prodrug Release Using Visible Light; J. Am. Chem. Soc.; Mar. 12, 2008; vol. 130, No. 13; pp. 4236-4237.
Meinhardt, et al.; "Wavelength-dependent penetration depths of ultraviolet radiation in human skin" Journal of Biomedical Optics; Jul./Aug. 2008; vol. 13; pp. 044030-1-044030-5.
Moses, et al.; "Emerging Strategies for Controlling Drug Release by Using Visible/Near IR Light"; Medicinal Chemistry; vol. 3; 2013; pp. 192-198.
Murthy, et al.; "Low energy light-triggered oxidative cleavage of olefins" Tetrahedron Letters 50; 2009; pp. 1041-1044.
Nkepang, et al.; Synthesis and Singlet Oxygen Reactivity of 1,2-Diaryloxyethenes and Selected Sulfur and Nitrogen Analogs; Photochemistry and Photobiology; 2012; vol. 88; pp. 753-759.
U.S. Appl. No. 14/396,802; Youngjae You; Office Action dated Jun. 19, 2015.
U.S. Appl. No. 14/396,802; Youngjae You; Response to Office Action filed Nov. 19, 2015.
U.S. Appl. No. 14/396,802; Youngjae You; Supplemental Response to Office Action and Statement of Substance of Interview filed Feb. 17, 2016.
U.S. Appl. No. 14/396,802; Youngjae You; Notice of Allowance dated Feb. 23, 2016.

* cited by examiner

*Primary Examiner* — Isaac Shomer
(74) *Attorney, Agent, or Firm* — Dunlap Codding, P.C.

(57) ABSTRACT

Activatable compositions that include at least one functional moiety and at least one cleavable linker directly or indirectly linked to the at least one functional moiety are disclosed. The at least one functional moiety is inactive when linked to the linker and activated upon cleavage of the linker. Methods of production and use of the activatable composition are also disclosed.

21 Claims, 22 Drawing Sheets
(18 of 22 Drawing Sheet(s) Filed in Color)

SINGLET OXYGEN-LABILE LINKERS AND METHODS OF PRODUCTION AND USE THEREOF

CROSS REFERENCE TO RELATED APPLICATIONS/INCORPORATION BY REFERENCE STATEMENT

This application is a continuation of U.S. Ser. No. 14/396,802, filed Oct. 24, 2013; which claims benefit under 35 USC §119(e) of provisional applications U.S. Ser. No. 61/637,516, filed Apr. 24, 2012; and U.S. Ser. No. 61/674,552, filed Jul. 23, 2012. The entire contents of the above-referenced patent applications are hereby expressly incorporated herein by reference.

STATEMENT REGARDING FEDERALLY FUNDED RESEARCH OR DEVELOPMENT

This invention was made with government support under Contract Number W81XWH-09-1-0071 awarded by the Department of Defense (DOD). The government has certain rights in the invention.

BACKGROUND

1. Field of the Invention

The presently disclosed and claimed inventive concept(s) is related to linkers utilized for drug delivery/release systems, and more particularly, but not by way of limitation, to singlet oxygen-labile linkers for controlled drug delivery/release systems, as well as methods of production and use thereof.

2. Description of the Background Art

Spatio-temporal controlled delivery of biologically active molecules is an important technique for many biological applications. Several strategies have been explored using internal or external stimuli such as temperature, pH, ultrasound, electric current and photo excitation. The use of light as an external signal for spatio-temporal release is a very appealing tool. Current techniques use ultraviolet (UV) or short visible light to release active compounds. However, UV and short visible light exhibit very limited tissue penetration (e.g., 340 nm, <200 μm). In addition, exposure to these wavelengths of light can also cause cellular damage. Thus, compositions for use in new methods of spatio-temporal controlled delivery of biologically active molecules are desired.

Therefore, there exists a great need for new and improved compositions comprising linkers that provide controlled drug delivery/release systems. The presently disclosed and claimed inventive concept(s) is directed to said compositions and methods of production and use thereof, which overcome the disadvantages and defects of the prior art.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 26A contains fluorescence-microscopy images (10× magnification) of live cells: (i) L=irradiated area of a well, R=un-irradiated area of the same well, (ii) cells treated with 2 (from Schemes 6 and 7) (1 µM) and irradiated, (iii) cells treated with 11 (from Schemes 6 and 7) (25 nM) and irradiated, (iv) cells treated with 11 (25 nM) without irradiation. FIG. 26B graphically illustrates light-dose dependent cell damage: cells treated with 11 (25 nM), then irradiated with 540±10 nm at 8 mW/cm$^2$ from 0-20 min, the average of at least triplicates.

FIG. 29A illustrates the structures of CA4 and colchicine. FIG. 29B is a schematic representation of prodrug CMP-L-CA4. FIG. 29C is a schematic representation of pseudo-prodrug CMP-NCL-CA4. FIG. 29D is a schematic representation of pseudo-prodrug CMP-L-Rh. CMP=core-modified porphyrin; L=aminoacrylate linker; CA4=combretastatin A-4; and NCL=non-cleavable linker.

DETAILED DESCRIPTION

Figure 1:
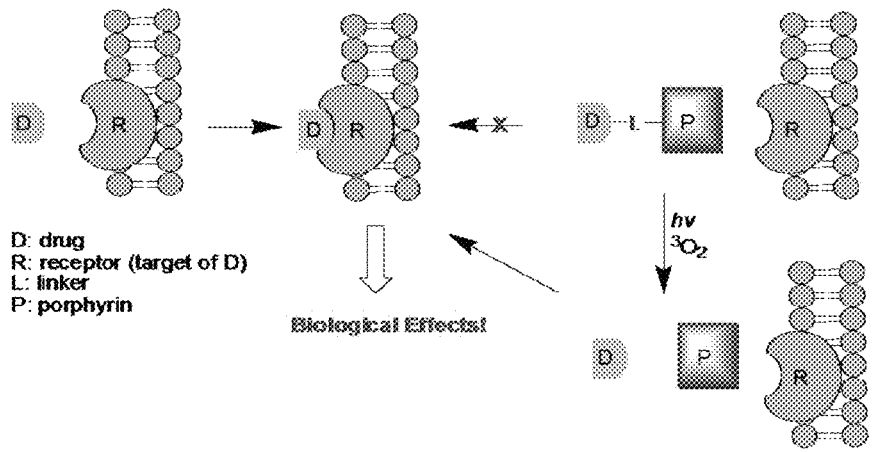
FIG. 1 is a schematic representation of the use of a singlet oxygen cleavable prodrug in accordance with the presently disclosed and claimed inventive concept(s).

At least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, delivery, and treatment of patients.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, "substantially pure" means an object species is the predominant species present (i.e., on a molar basis it is more abundant than any other individual species in the composition). Generally, a substantially pure composition will comprise more than about 50% percent of all macromolecular species present in the composition, such as more than about 55%, 60%, 65%, 70%, 75%, 80%, 85%, 90%, 95%, and 99%. In one embodiment, the object species is purified to essential homogeneity (contaminant species cannot be detected in the composition by conventional detection methods) wherein the composition consists essentially of a single macromolecular species.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The term "agent" refers to a chemical compound, a mixture of chemical compounds, a biological macromolecule, or an extract made from biological materials.

The term "antagonist" refers to an agent that reduces an activity of a protein/enzyme. The term "agonist" refers to an agent that increases an activity of a protein/enzyme.

The term "patient" includes human and veterinary subjects. In certain embodiments, a patient is a mammal. In certain other embodiments, the patient is a human.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic agent" refers to an agent that may be administered in vivo to bring about a therapeutic and/or prophylactic/preventative effect.

A "disorder" is any condition that would benefit from treatment with the polypeptide. This includes chronic and acute disorders or diseases including those pathological conditions which predispose the mammal to the disorder in question. Non-limiting examples of disorders encompassed by the presently disclosed and claimed inventive concept(s) include diabetic retinopathy, ocular inflammation, corneal inflammation, diabetic macular edema, macular degeneration, uveitis, retinal inflammation, retinal vascular leakage, retinal neovascularization, cancer, and the like.

The terms "cancer" and "cancerous" refer to or describe the physiological condition in mammals that is typically characterized by unregulated cell growth. Examples of cancer include, but are not limited to, carcinoma, lymphoma, blastoma, sarcoma, leukemia, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma, and various types of head and neck cancer.

"Mammal" for purposes of treatment refers to any animal classified as a mammal, including human, domestic and farm animals, nonhuman primates, and zoo, sports, or pet animals, such as dogs, horses, cats, cows, etc.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the presently disclosed and claimed inventive concept(s). The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

The compositions of the presently disclosed and claimed inventive concept(s) may be administered to a patient by any method known in the art, including but not limited to, oral, topical, transdermal, parenteral, subcutaneous, intranasal, intramuscular, intraperitoneal, intravitreal and intravenous routes, including both local and systemic applications.

The term "short and mid-visible light" as used herein refers to a tissue penetrable low energy light having a wavelength in a range of from about 380 nm to about 600 nm.

The term "long visible light" as used herein refers to a tissue penetrable low energy light having a wavelength in a range of from about 600 nm to about 750 nm.

The terms "near Infrared" and "near IR" are used interchangeably herein and refer to a tissue penetrable low energy light having a wavelength of greater than about 650 nm. In certain embodiments, the term "near IR" may refer to a light having a wavelength in a range of from about 650 nm to about 900 nm.

The term "close proximity" as used herein will refer to two molecules being disposed within diffusion distance of one another. The exact distance between two molecules will vary, depending on the particular distance by which the desired diffusion molecule will travel. For example but not by way of limitation, molecules disposed in close proximity to one another may be disposed within 0 to about 200 nm of one another. In other non-limiting examples, two molecules are disposed within a distance that is within about 100 nm of one another, or 50 nm of one another, or 20 nm of one another.

Turning now to particular embodiments of the presently disclosed and claimed inventive concept(s), compositions are disclosed that can be utilized for spatio-temporal release of bio-active molecules in response to exposure to an activator (such as, but not limited to, light). In certain embodiments, the presently disclosed and claimed inventive concept(s) comprise singlet oxygen-labile linkers for use in controlled reagent delivery and release. The composition includes at least one functional moiety, wherein delivery of the activated functional moiety to a particular location/site in a subject is desired. The composition further comprises a linker linked directly or indirectly to the functional moiety, whereby linkage of the linker to the functional moiety inactivates the functional moiety. The linker is cleavable by singlet oxygen generated by exposure of the composition to an activator, and cleavage of the linker (directly or indirectly) results in activation of the functional moiety by releasing the functional moiety or the minimally modified functional moiety having similar functional effects.

The composition may further include a targeting/delivery moiety that is capable of passively or actively associating with the desired delivery site. When a targeting/delivery moiety is present, the linker links the inactive functional moiety to the targeting/delivery moiety. In this manner, the composition is delivered to the desired site of delivery, and cleavage of the linker (directly or indirectly) results in activation of the functional moiety at the desired site of delivery.

In certain embodiments, the composition may further include a sensitizer (such as but not limited to, a photosensitizer) that is disposed in close proximity to the linker. Exposure of the sensitizer to an activator results in generation of singlet oxygen by the sensitizer. Generation of singlet oxygen in close proximity to the linker results in cleavage of the linker tethered to the functional moiety, thus activating the functional moiety (when a targeting/delivery moiety is present in the composition, the activation of the functional moiety occurs at the desired delivery site). The sensitizer is chosen based upon the activator utilized; for example, when visible/near IR is utilized as the activator, a photosensitizer is used; when luminescence is utilized as the activator, a combination of chemicals or a chemical and enzyme combination may be used; when light wavelengths longer than 800 nm are used, two photon absorbing photosensitizers (or two photon absorbers with photosensitizers) may be used. Non-limiting examples of photosensitizers that may be utilized in accordance with the presently disclosed and claimed inventive concept(s) include porphyrin, phthalocyanines, BODIPY (or aza-BODIPY)-type photosensitizers, chlorins, bacteriochlorins, any non-porphyrin-based photosensitizers, and combinations and derivatives thereof. In addition, non-limiting examples of other sensitizers include single-walled carbon nanotubes, conjugates of light harvesting materials (either via one or two photon absorption) and photosensitizer, nanoscintillator alone or with sensitizers, sonar sensitizers (used with ultrasound), radiosensitizers (used with ionization waves such as x-rays and γ-rays), MRI contrasting agents (used with long magnetic waves), and the like, as well as combinations and derivatives thereof.

The linker utilized in accordance with the presently disclosed and claimed inventive concept(s) may be any molecule capable of (1) being tethered to the inactive functional moiety, (2) being cleavable by singlet oxygen, (3) allowing for the direct or indirect activation of the functional moiety upon cleavage thereof, and (4) when a targeting/delivery moiety is present, linking the inactive functional moiety to the targeting/delivery moiety. Non-limiting examples of linkers that fall within the scope of the presently disclosed and claimed inventive concept(s) are described in the Examples; in particular embodiments, the linker may be aminoacrylate, aminoacrylthioate, aminoacrylamide, beta-aminoketone, and combinations and derivatives thereof.

In addition, spacers may also be included in the composition to provide optimum spacing between the different components of the composition (i.e., functional moiety, targeting moiety, linker and sensitizer, etc.), and to allow optimum interaction of generated singlet oxygen with the linker, resulting in cleavage thereof. Non-limiting examples of spacers that may be utilized in accordance with the presently disclosed and claimed inventive concept(s) include piperidin-4-ylmethanol, pyrrolidine-2-carboxylic acid, pyrrolidine-3-carboxylic acid, piperidin-4-ylmethyl-2-bromoacetate, 1-(3-bromoporpyl)piperazine (of which nitrogen will be part of the linker and the other functional group can be used for attaching the spacer part to other components (i.e., sensitizers, drugs, or other components)), and combinations and derivatives thereof.

In certain embodiments, the functional moiety may be a biologically active moiety, such as but not limited to, small molecules, peptide, proteins, nucleotides (RNA, DNA, etc.) and the like, including therapeutic moieties. Therapeutic moieties may be any molecule capable of exhibiting a desired therapeutic effect. Non-limiting examples of inactive therapeutic moieties that may be utilized in accordance with the presently disclosed and claimed inventive concept(s) include pro-drugs and nano-drug-carriers (such as but not limited to, deactivated drugs encapsulated in liposomes, polymers, nanospheres, nanocapsules, micelles, dendrimeric structures, solid lipid nanoparticles, other nanostructures, micro-particles and other micro-structures, gel and solid formulations, fullerenes (such as but not limited to, buckyballs), combinations and derivatives thereof, and the like). Particular non-limiting examples described herein include Estron, Combretastatin A4, SN-38, and paclitaxel.

In other embodiments, the functional moiety may be a detectable moiety. The detectable moiety may be any molecule capable of detection by a detection method. Non-limiting examples of detectable moieties include reporter molecules, imaging agents, and the like. Particular non-limiting examples of detectable moieties include fluorophores, MRI contrasting agents, enzymes, radioisotopes, sensitizing agents (used for ultrasound, photoacoustic imaging, radiography, and the like), and combinations and derivatives thereof.

In particular embodiments, the composition is provided in the form of a dendrimer. The dendrimeric structure is a highly branched macromolecule that provides a high drug carrying capacity (i.e., multiple functional moieties in a single composition), along with high targeting moiety capacity in a single molecular weight rather than a distribution of sizes. The dendrimeric structure of these compositions provides fine control of the release mechanism.

Regardless of the structure of the composition, the composition may include multiple functional moieties, and the multiple functional moieties may be the same or different (including the presence of therapeutic moieties, other biologically active moieties and/or detectable moieties in a single dendrimeric structure). Likewise, the composition may include multiple targeting/delivery moieties, wherein these moieties may be the same or different.

The targeting/delivery moiety may be any molecule known in the art or otherwise contemplated herein that is capable of associating with a desired location/site, whereby the composition is targeted to the site, and the individual components thereof (including the activatable functional moiety) is thus delivered to the desired location/site. Non-limiting examples include antibodies, ligands, tumor markers, aptamers, PEG, albumin, tumor specific peptides, AFFI-BODY® molecules (Affibody AB, Solna, Sweden), vitamins (such as but not limited to, folic acid), carbohydrates, hormones, low density lipoproteins (LDL), and the like, as well as combinations and derivatives thereof. The targeting/delivery moiety may bind to a receptor or other molecule exposed on the surface of a cell; optionally, the targeting/delivery moiety may pass through the cell membrane and bind to intracellular components.

The presently disclosed and claimed inventive concept(s) is further directed to methods of producing the compositions described herein above. Methods of producing the compositions are described in detail in the Examples. Additional methods of producing the compositions described herein that may be contemplated by one of skill in the art also fall within the scope of the presently disclosed and claimed inventive concept(s).

The presently disclosed and claimed inventive concept(s) includes kits containing the whole or any portion of the compositions described herein above. For example, but not by way of limitation, a kit may include a composition comprising the linker alone. Another non-limiting example of a kit includes two or more of the following components: at least one type of linker, at least one type of spacer, at least one type of sensitizer, at least one type of functional moiety, and at least one type of targeting/delivery moiety. Said kit may include unattached components, or any combination of the components may be attached to one another. A final non-limiting example of a kit includes all five of the above components; said example includes a kit containing unattached components, as well as any attached combination of the above.

Another embodiment of the presently disclosed and claimed inventive concept(s) is directed to a method of inhibiting and/or decreasing the occurrence and/or severity of at least one condition/disorder in a patient comprising administering an effective amount of an activatable composition, as described herein above, to the patient, and exposing at least a portion of the patient (such as, but not limited to, a portion associated with the desired delivery location) to an activator, whereby singlet oxygen is generated and the linker of the activatable composition is cleaved, resulting in activation of the functional moiety. When the composition contains a targeting/delivery moiety, the activation of the functional moiety occurs at the desired delivery location. The activator exposure primarily controls the location and time of activation, and the targeting/delivery moiety could further improve the local specificity of the activation.

In another embodiment of the method, at least one component of the activatable composition administered to the patient (such as but not limited to, the linker, the targeting/delivery moiety, and/or the sensitizer) is further defined as comprising a detectable moiety. In this embodiment, the method further comprises the step of detecting the presence of the activatable composition at a desired delivery site and then exposing at least a portion of the patient to the activator, whereby singlet oxygen is generated in close proximity to the at least one linker, resulting in cleavage of the linker and activation of the at least one therapeutic moiety. In a particular non-limiting example, a photosensitizer may be utilized that comprises a fluorescence dye and a targeting group. In this manner, the photosensitizer is dual-functioning: it may detect a desired delivery location (such as but not limited to, a tumor) with the targeting group, and then cooperates in the therapeutic use via singlet oxygen generation as described herein above.

Any conditions/disorders disclosed or otherwise contemplated herein may be treated in accordance with the methods described herein above. However, the scope of the presently disclosed and claimed inventive concept(s) is not limited to those conditions/disorders expressly disclosed herein. For example, the scope of the disorders/conditions that may be treated in accordance with the presently disclosed and claimed inventive concept(s) includes any disorder/condition that can be reached by the activatable composition and the activator. Particular target disorders/conditions included within the scope of the presently disclosed and claimed inventive concept(s) include any disorder/condition for which photodynamic therapy is considered a known or potential treatment strategy.

Any activator capable of activating the sensitizer to generate singlet oxygen known in the art or otherwise contemplated herein falls within the scope of the presently disclosed and claimed inventive concept(s). Non-limiting examples of activators include irradiation with visible/near IR light, irradiation with ionizing radiation (i.e., x-rays or gamma rays), exposure to electromagnetic waves/materials, exposure to luminescence, exposure to fluorescence, exposure to ultrasound, and the like, as well as any combination thereof.

Singlet oxygen can be generated in any methods known in the art or otherwise contemplated herein. For example but not by way of limitation, singlet oxygen may be generated either directly from the sensitizer or indirectly by electromagnetic wave-absorbing materials coming into contact with their corresponding electromagnetic waves. When absorption of light (photon) by a sensitizer is utilized, any wavelength (UV, visible, near IR, ultrasound, radiowaves, ionizing radiation, etc.) can be used if the sensitizer observes the light and transfers the energy to oxygen (thereby yielding singlet oxygen). Optionally, light can be observed by a light harvesting material, which transfers the energy to oxygen generating singlet oxygen. Any light source known in the art or otherwise contemplated herein may be utilized; non-limiting examples include diode lasers, LED, broad band lamps with and without filters, chemo- or bio-luminescence materials, transducers (ultrasound), radioactive material or equipment (ionizing radiation), equipment for generating radio or magnetic waves, combinations thereof, and the like.

In one embodiment, the activator comprises irradiation with light in a range of from about 380 nm to about 1200 nm. Particular examples of ranges of light wavelength that may be utilized include a lower range limit of about 380 nm, about 400 nm, about 425 nm, about 450 nm, about 475 nm, about 500 nm, about 525 nm, about 550 nm, about 575 nm, about 600 nm, about 650 nm, about 675 nm, about 700 nm, about 725 nm, about 750 nm, about 775 nm, about 800 nm, about 825 nm, about 850 nm, and the like, and an upper range limit of about 1200 nm, about 1175 nm, about 1150 nm, about 1125 nm, about 1100 nm, about 1025 nm, about 1000 nm, about 975 nm, about 950 nm, about 925 nm, about 900 nm, about 875 nm, about 850 nm, about 825 nm, about 800 nm, about 775 nm, about 750 nm, and the like. In certain embodiments, short and mid-visible light, long visible light, and/or near IR light irradiation may be used as the activator.

The use of singlet oxygen in the methods of the presently disclosed and claimed inventive concept(s) provides advantages over the prior art light-triggered drug delivery methods; in particular, the prior art methods suffered from limited tissue penetration as well as cellular damage caused by exposure to non-biocompatible/toxic levels of light (i.e., high energy UV light), and it was difficult to control the initiation/activation of the functional moiety at the desired location. In contrast, the methods of producing singlet oxygen described herein are non-toxic/biocompatible and provide tissue penetration effective for cleaving the linker and activating the functional moiety of the composition at the desired location and time.

In a particular non-limiting embodiment of the methods of the presently disclosed and claimed inventive concept(s), irradiation with long visible and/or near IR light results in generation of singlet oxygen by the sensitizer of the composition, and the singlet oxygen generated in close proximity to the linker allows for cleavage of the linker and activation of the functional moiety.

EXAMPLES

Examples are provided hereinbelow. However, the present inventive concept(s) is to be understood to not be limited in its application to the specific experimentation, results, and laboratory procedures. Rather, the Examples are simply provided as one of various embodiments and are meant to be exemplary, not exhaustive. However, it is to be understood that the information contained therein is provided for the purpose of description, and the presently disclosed and claimed inventive concept(s) is not limited to such exemplary information contained therein. The inventive concept(s) is capable of other embodiments or of being practiced or carried out in various ways.

Example 1

Low Energy Light-Triggered Oxidative Cleavage of Olefins

Singlet oxygen is a toxic species in photodynamic therapy (PDT). PDT involves three main components: low energy (visible/near IR) light, oxygen, and a photosensitizer.[1] The energy of the light is transferred to triplet oxygen through a photosensitizer generating singlet oxygen. PDT has been clinically practiced in the treatment of various diseases such as cancers, the wet form of age-related macular degeneration, psoriasis, and acne.[2] Although PDT has been proved effective against such diseases, the mechanistic details of the reactions of singlet oxygen with bio-molecules have not been fully understood at the molecular level.

Applications of the 1,2-cycloaddition reaction of singlet oxygen have been proposed for the photo-triggerable drug delivery systems such as liposomes, cyclodextrin complexes, and prodrug (FIG. 1).[3-7] Free drugs can be released upon the irradiation of low energy light via the cleavage reaction of singlet oxygen following the 1,2-cycloaddition reaction with olefins (Scheme 1). This strategy provides two critical advantages over other drug delivery or prodrug systems. First, the release of free drugs can be more actively controlled than in the strategies using enzymes or specific pH conditions. Second, low energy light allows practical applications of this strategy at a tissue level. High energy UV has been used for releasing drugs or biologically important molecules by UV irradiation.[8] Although the UV light cannot penetrate deeper than 1 mm into tissues, the low energy light can reach much deeper tissue, ~1 cm.[9]

Scheme 1. Singlet oxygen generation and 1,2-cycloaddition reaction of olefin followed by cleavage of dioxetane

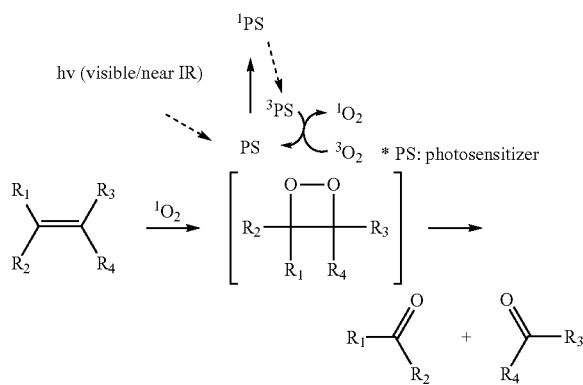

Ideally, an olefinic linker should be cleaved within a short period of time without any side reactions. Although there are several reports about the kinetic study of the reactions of singlet oxygen with olefins, the irradiation conditions were not described in detail such as intensity and/or wavelength of the light at target samples.[10-16] Since intensity and wavelength of light are important for drug delivery applications, various olefins were examined to find appropriate linkers for this drug delivery strategy and to examine effects of substituents at the olefins on the rate of oxidation. Herein, comparative yields of photo-oxidation of a series of substituted olefins after irradiation by visible light (400-800 nm) at 200 mW/cm$^2$ are reported.

Results and Discussion of Example 1

Figure 2:
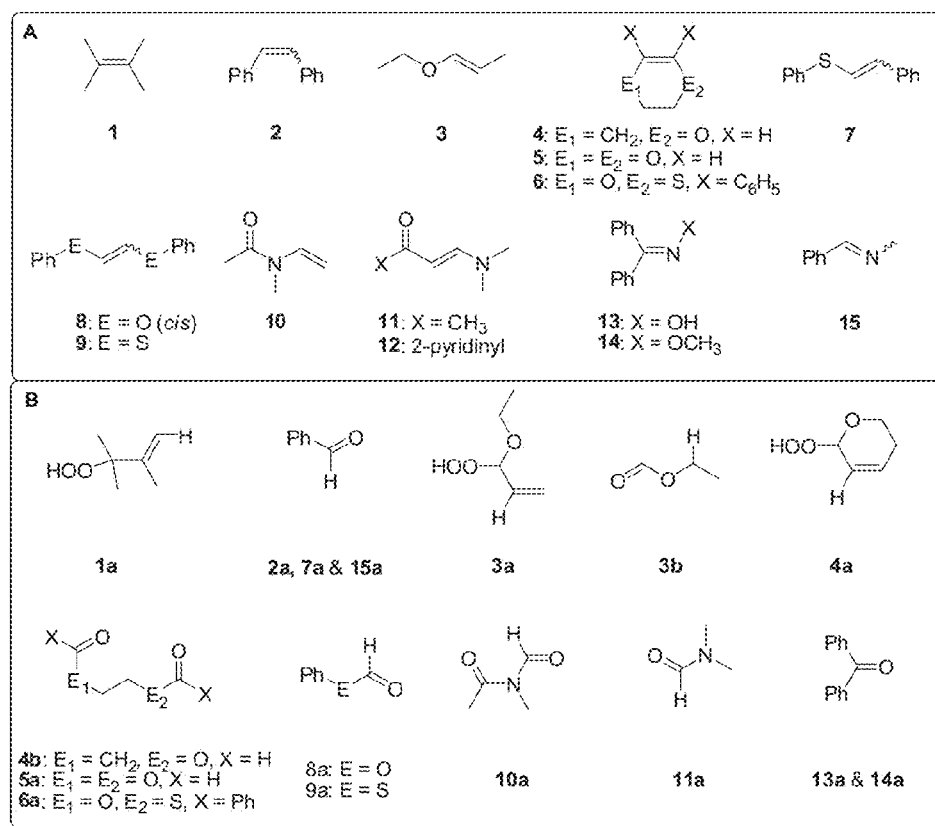
FIG. 2 schematically represents olefins studied for photo-oxidation (Panel A), and photo-oxidation products of the olefins 1-15 of Panel A with hydrogen used for the quantification by $^1$H-NMR (Panel B).

To evaluate oxidative cleavage of olefins, olefins 1-15 were irradiated in the presence of 5,10,15-triphenyl-20-(4-hydroxyphenyl)-21H,23H-porphyrin (TPP-OH) as a photosensitizer (FIG. 2). To maintain the significance of this research for biological applications, low intensity light (200 mW/cm$^2$) with a wavelength range of 400-800 nm was used. At the standard condition, the reaction solution was irradiated for 1 h. Experimental conditions are described in the Supplementary Information section below. The olefins were first irradiated without TPP-OH to observe their stability in the absence of singlet oxygen generation (Table 1). All the substrates showed negligible reactivity (<1%) with atmospheric oxygen and the irradiation without TPP-OH, except for benzophenone oxime 13, which was oxidized to benzophenone with 7% conversion. It was previously demonstrated that benzophenone oxime was slowly converted to a mixture of benzophenone and nitric acid in the presence of oxygen and moisture.

TABLE 1

Conversion of the photo-oxidation products

| Olefin | Products |
| --- | --- |
| 1 | 1a (99%)$^a$ |
| 2 | 2a (11%) |
| 3 | 3a (23%) & 3b (18%) |
| 4 | 4a (34%) & 4b (65%) |
| 5 | 5a (77%) |
| 6 | 6a (99%) |
| 7 | 7a (22%) |
| 8$^b$ | 8a (80%) |
| 9$^b$ | 9a (14%) |
| 10 | 10a (30%) |
| 11 | 11a (64%) |
| 12$^c$ | — |
| 13 | 13a (18%) |
| 14 | 14a (1%) |
| 15 | 15a (16%) |

$^a$Conversion determined by NMR integration from photo mixture, except substrates 6, 13 and 14 determined by HPLC.
$^b$Substrates irradiated only for 15 min.
$^c$Olefin peaks completely consumed but no aldehyde peak was observed on $^1$H NMR.

The photo-oxidation of 2,3-dimethyl-2-butene 1 resulted in the formation of 3-hydroperoxy-2,3-dimethyl-1-butene 1a to 99% yield by ene reaction.[17,18] The higher reactivity of 1 with singlet oxygen, as compared to other substrates, can be attributed to its electron-rich double bond.[19] Substrate 2 was studied to observe 1,2-cycloaddition reaction with singlet oxygen yielding the dicarbonyl compounds as oxidative cleavage products. It also seemed interesting to study the effect of aryl groups as substituents on the olefin. As previously reported, singlet oxygen reaction with aryl-substituted olefins does not tend to be an accelerated process.[20] Benzaldehyde 2a was formed as the only product in a low conversion.

Substrates 3-6 are vinyl ethers and diethers. Substrate 3 afforded the ene reaction product 3a due to the presence of three hydrogens at the allylic position. The hydroperoxide 3a was formed in competition with carbonyl compounds as oxidative cleavage products via the 1,2-cycloaddition reaction. For the carbonyl compounds, ethyl formate 3b was only detected in the reaction mixture by $^1$H NMR. The other product, acetaldehyde, seemed to evaporate due to its low boiling point, 21° C. Dihydropyran 4 also exhibited a similar reactivity to substrate 3. The 1,2-cycloaddition reaction product 4b was formed two times more than the ene reaction product 4a, which was consistent with previous reports.[21] However, for substrate 3, the ene reaction product 3a was formed slightly more than the 1,2-cycloaddition reaction product 3b. Both substrates 5 and 6 on photo-oxidation gave high yields of the product esters 5a and 6a, respectively. The strong electron donating effects of disubstituted hetero atoms O & S enhanced the reactivity with singlet oxygen.

Figure 3:
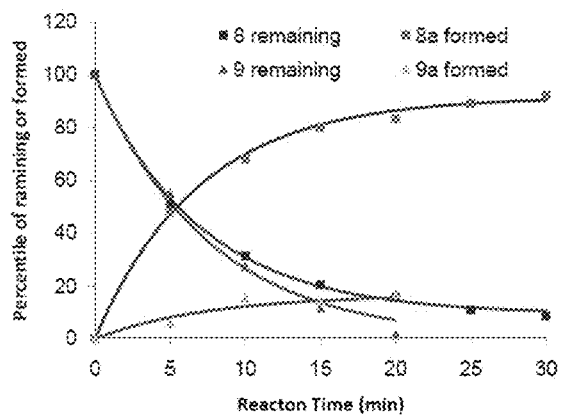
FIG. 3 graphically represents a comparison of reaction kinetics of substrates 8 and 9 shown in FIG. 2, Panel A.

Substrate 7 is sulfur activated olefin and exhibited a comparatively lower reactivity than vinyl ethers 3 & 4. Substrates 8 & 9 were chosen to compare the reactivities of dioxygen vs. disulfur substituted olefins. Substrate 8 was synthesized by the previous method.[22] Initially, 8 & 9 disappeared completely after the 1-hr irradiation with TPP-OH. Hence, a time dependent study was conducted to determine the reaction kinetics of 8 & 9. They were irradiated for every 5 minutes with TPP-OH and monitored by $^1$H NMR each time. The formation of product 8a was directly proportional to the decrease of substrate 8 (FIG. 3). However, the conversion of substrate 9 did not show a corresponding increase of product 9a. Product 9a was formed in much lower yield although the starting material was consumed to a much greater extent, 88% after 15 min. There might be other oxidation products as side products which cannot be detected by $^1$H NMR. Substrate 8 seemed to be a better linker for the singlet oxygen-cleavable drug delivery systems with respect to its reaction kinetics and side reactions. However, if the formyl group of the cleaved product (i.e., a formylated drug) is stable, it might attenuate the activity of a drug. To address this concern, the kinetics of regeneration of a phenol from the formate (8a) by biological nucleophiles such as amines and thiols is under investigation.

N-Methyl-N-vinyl acetamide 10 showed a reasonable reactivity with singlet oxygen as compared to vinyl ethers (Table 1). This is probably due to the keto-amine resonance which can decrease the electron density of the π bond, thereby retarding the 1,2-cycloaddition reaction. Substrate 11 showed a higher reactivity with singlet oxygen possibly due to the availability of the lone pair electrons of nitrogen for enriching the double bond. Substrate 12 on irradiation showed complete disappearance of the starting material without any formation of the aldehyde product. However some unrecognizable products in $^1$H NMR were obtained in the reaction mixture.

Substrates 13-15 are examples of the reactivity of a π bond between carbon and nitrogen other than olefins. Substrate 13 was more reactive than 14. On the contrary, 13 showed lower reactivity with singlet oxygen than 14 under a saturated oxygen condition and in methanol.[23] Oxidation of imine 15 gave benzaldehyde in a 16% conversion. Interestingly, 15 showed a similar reactivity to 13.

In summary, heteroatom activated olefins, 5, 6, 8, and 9 showed a promising reactivity with singlet oxygen>75% conversion within 1 h. Olefins 8 and 9 were cleaved more than 80% by the irradiation of light of 400-800 nm at 200 mW/cm$^2$ within 15 min without oxygen saturation. 1,2-Dioxy olefin 8 seemed more advantageous because the cleavage reaction did not generate any side products. Recently, another group showed the potential of dioxy olefin as a linker for the site-specific prodrug release.[7] The low energy light-induced C=C bond cleavage reaction is practical, fast, and clean providing a new tool for drug delivery strategies.

Supplementary Information for Example 1
Experimental Section:
Chemicals and solvents were of analytical grade and used as received unless otherwise stated. Olefins 1-15 (see FIG. 2) except 8 were purchased from Sigma-Aldrich Co. or Acros Organics, and used without purification. TPP-OH was prepared according to the reported method.[24] Nuclear magnetic resonance spectra were recorded in CDCl$_3$ on a Bruker AM-400 spectrometer. Chemical shifts are given in parts per million relative to Me$_4$Si or CHCl$_3$ for $^1$H NMR. HPLC analysis was carried out on an Agilent 1100 series using a RP C18 column (0.46×15 cm). The mobile phase used was 0.1% TFA in MeCN and H$_2$O. The UV absorbance was recorded at 254 and 440 nm.

Preparation of 5,10,15-triphenyl-20-(4-hydroxyphenyl)-21H,23H-porphyrin (TPP-OH): BBr$_3$ (0.68 mL, 7.19 mmol) was added to a stirred solution of the porphyrin (TPP-OMe, 230 mg, 0.36 mmol) in CH$_2$Cl$_2$ (50 mL) kept under nitrogen at 0° C. The mixture was stirred at 0° C. for 1 h and then at room temperature for 18 h. The reaction mixture was then diluted with 100 mL of CH$_2$Cl$_2$ and neutralized with the desired amount of saturated Na$_2$CO$_3$ solution until the green colored mixture turned dark red. The layers were separated, and the dark red organic layer was thoroughly washed with water, dried with sodium sulfate, filtered, and concentrated under vacuum. The crude product was purified by column chromatography on a silica gel column starting with a solvent system of CH$_2$Cl$_2$:MeOH (99:1) to elute the unreacted porphyrin (TPP-OMe) and then with CH$_2$Cl$_2$:MeOH (95:5) to yield 180 mg (74%) of the pure porphyrin (TPP-OH).

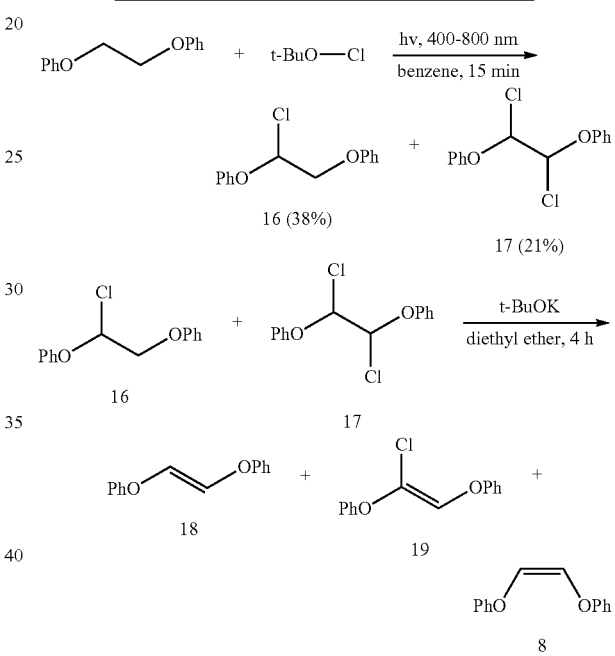

SCHEME 2. Synthetic scheme for the preparation of 8

Preparation of 1,2-cis-diphenoxyethylene (8): Compound 8 was prepared based on Sales et al. (1979)[22], but the details of reaction conditions were not described in the reference. To a solution of 1,2-diphenoxy ethane (2.14 g, 10 mmol) in benzene (30 mL) was added tert-butoxy chloride (2.26 mL, 20 mmol) dropwise. The solution was stirred at room temperature and irradiated using a wavelength of 400-800 nm for 15 min. The reaction mixture was reduced under vacuum, and the crude product was purified on a silica gel column using hexanes:ethyl acetate (99:1). An inseparable mixture of 1-chloro-1,2-diphenoxy ethane (16, 0.96 g, 38%) and 1,2-dichlorodiphenoxy ethane (17, 0.60 g, 21%) was obtained. This mixture was then used for the next step.

To a stirred solution of potassium tert-butoxide (677 mg, 6.3 mmol) in anhydrous ether at 0° C. was added a solution of the mixture of 16 and 17 (500 mg) in anhydrous ether dropwise. The reaction mixture was then stirred at room temperature for 4 h. The progress of the reaction was monitored by TLC. The starting material had completely disappeared with two close moving product spots. The reaction was stopped at this stage. The reaction mixture was diluted with ether and washed with water. The organic layer was separated and dried under vacuum. The crude product was purified on a silica gel column using hexanes:ethyl acetate (99:1). The second fraction could not be completely separated. A part of the second fraction was however obtained 3 mg as a pure compound 8 showing identical $^1$H NMR data as in Yang et al. (1999).[25] Based on $^1$H NMR spectra the first fraction was a mixture of products 18, 19 and 8 identified by their vinylic proton peaks as trans-diphenoxy ethylene (6.91 ppm), 1-chloro-1,2-diphenoxy ethylene (6.60 ppm) and cis-diphenoxy ethylene (6.18 ppm), respectively.

General Photooxidation Procedure.

In a NMR tube, an olefin (0.0048 mmol) was dissolved in $CDCl_3$ (0.5 mL). The porphyrin (TPP-OH) (3 mg, 0.0048 mmol) was dissolved in this solution, and the reaction mixture was irradiated for 1 h using a filtered mercury xenon lamp (300 W). The filtered light intensity used was 200 mW/cm$^2$ at the target NMR tube, and the whole sample solution was irradiated. Wavelength of the light was 400-800 nm after passing through two glass filters (FSQ-GG400 and FSQ-KG1, Newport Corporation) and a water filter to remove heat. The NMR tube was closed with a cap during the experiment to avoid solvent evaporation. The photooxidized mixture was analyzed by $^1$H NMR or HPLC. Similarly a control experiment (without the porphyrin) was also carried out for all the substrates, under exactly the same reaction conditions.

Example 2

Synthesis and Singlet Oxygen Reactivity of 1,2-Diaryloxyethenes and Selected Sulfur and Nitrogen Analogs Electron-rich olefins can be used as reagents in organic synthesis. Among other things vinyl ethers are reagents for cycloadditions[26,27,] cyclopropanations[28], and polymer syntheses.[29] Vinyl amines are also used in the preparation of polymer dyes, catalysis and ion-exchange resins. Singlet oxygen being an electrophilic reagent can react with electron-rich olefins with electron-rich olefins via ene reactions and 1,2-cycloadditions, and with conjugated dienes via 1,4-cycloadditions. 1,2-Cycloaddition reactions of singlet oxygen to olefinic bonds form dioxetanes that spontaneously fragment to generate two carbonyl products (Scheme 4).[18,30-34] The 1,2-cycloaddition reaction of singlet oxygen has been proposed for photo-triggerable drug delivery systems in the forms of liposomes, cyclodextrin complexes and prodrugs.[3-5] Screening of various 1,2-substituted olefins resulted in the choice of 1,2-dioxy, 1,2-dithioxy, 1-oxy and 1-thioxy olefins (vinyl groups activated by heteroatoms) for the singlet oxygen-cleavable linkers.[35] In particular, 1,2-diaryloxyethene was proposed for site specific prodrug release and its singlet oxygen-mediated cleavage in solutions was demonstrated.[7]

While considerable efforts have recently been made in the development of synthetic methods for mono-substituted olefins[36], there have been a number of publications for the syntheses of 1,2-diheteroatom-substituted olefins.[22,25,37] With the exception of (2-aryloxyvinyl)phenyl sulfanes which were synthesized by the reaction of benzenesulfenyl chloride with vinylaryl ethers[38-41], all the synthetic processes are limited only for symmetric molecules and to procedures that lead to low yield or non-stereospecificity (mixture of Z and E isomers)[22,25,37]. Lengthy multiple steps are also required and some of the processes required harsh reaction conditions. For example, 1,2-diphenoxyethene has been synthesized from ethylene chlorohydrins in 7-step sequence involving high pressure and high temperature.[42] The other method for the same compound involved chlorination and dehydrochlorination of 1,2-diphenoxyethane.[22] This method is limited for the synthesis of symmetric molecules and yields a mixture of E and Z-products in low yields. The most recent method for the preparation of 1,2-diphenoxyethene and derivatives involved bromination followed by stereospecific debromination to give either E- or Z-product.[25] This method is also limited to symmetric 1,2-diaryloxyethenes using harsh conditions and providing low yields.

Recently, light-controlled drug release has attracted much attention for new drug delivery systems.[5,7,43,44] However, the limited synthetic methods for 1,2-diheteroatom-substituted olefins have been one of the major hurdles. Thus, versatile, efficient, and stereospecific synthetic routes should be developed for these applications. Here, the first facile synthetic approach for E-1,2-diheteroatom-substituted olefins [R—O(H)C=CX(H)—R': X=O, N, or S, Scheme 3] is described. It is a versatile, efficient and stereospecific method in as few as four steps from starting materials. Here, it has been demonstrated that the chemistry can be used for preparation of both symmetrically (R—O(H)C=C(H)O—R) and asymmetrically diheteroatom-substituted (R—O(H)C=C(H)O—R', R—O(H)C=C(H)S—R'; R—O(H)C=CHN—R') olefins from a variety of common functional groups such as —OH, —NH and SH. The photooxidation of those olefins previously unreported are also reported.

Scheme 3. Synthetic route for vinyl diether and its analogues

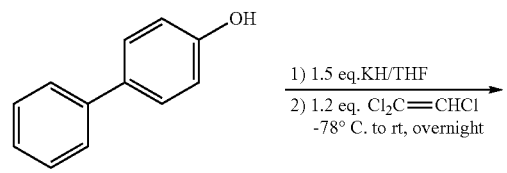

1) 1.5 eq. KH/THF
2) 1.2 eq. $Cl_2C=CHCl$
   −78° C. to rt, overnight

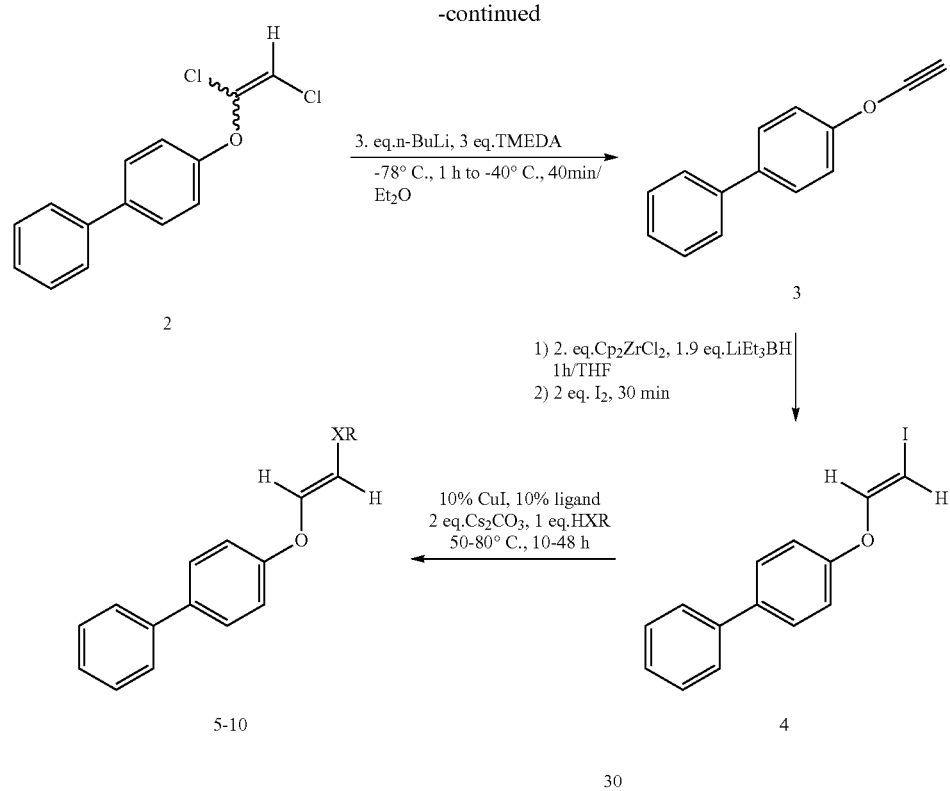
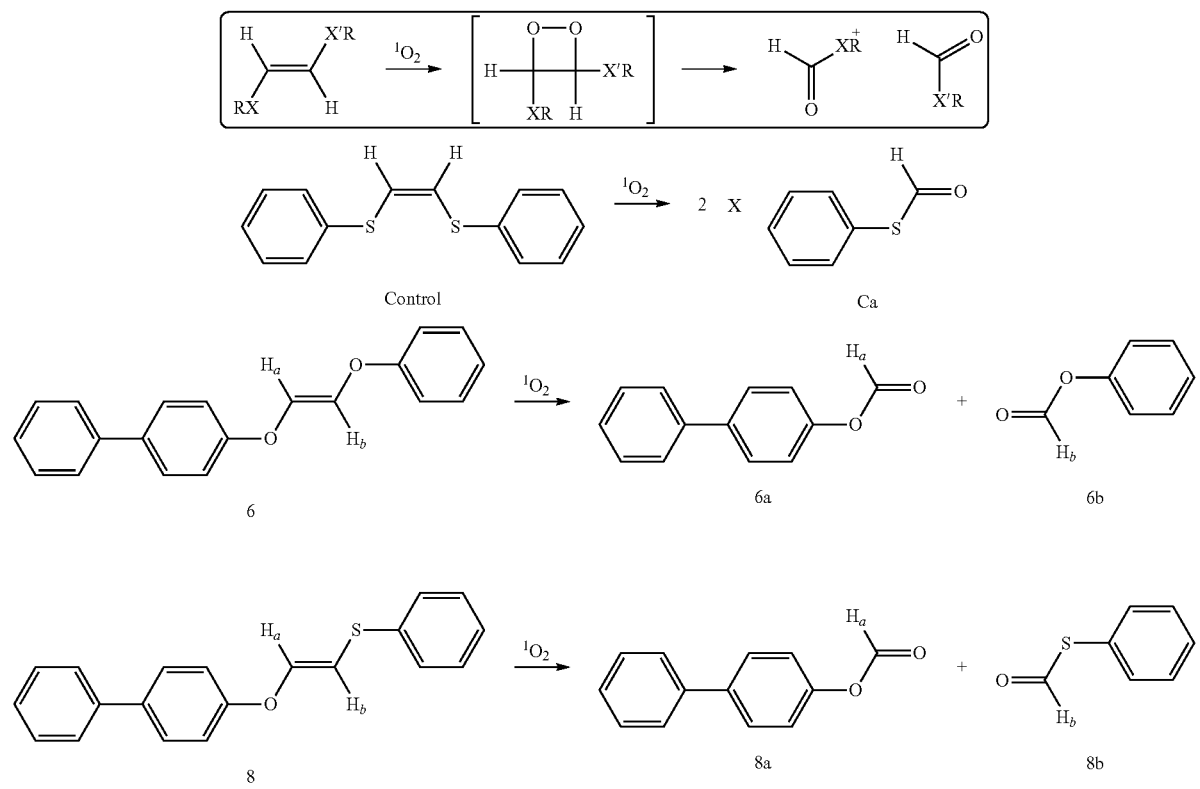
Scheme 4. Possible [2+2] addition reaction of electron-rich olefins with singlet oxygen and expected products of control, 6, 8, and 10.

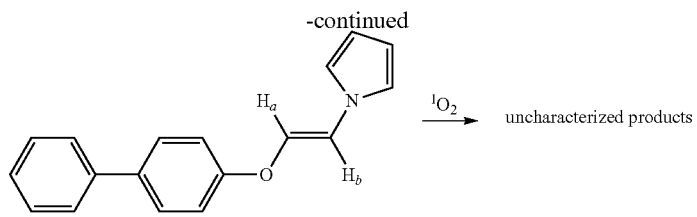

Materials and Methods for Example 2

All solvents and reagents were used as obtained from Sigma Aldrich and Thermo Fisher Scientific unless otherwise stated. All reactions were monitored by TLC using 5-17 μm silica gel plates with fluorescent indicators from Sigma-Aldrich. All column chromatography was done using 40-63 μm silica gel from Sorbent Technologies. NMR spectra were recorded at 25° C. using a 300 or 400 MHz Spectrometer. NMR solvents with residual solvent signals were used as internal standards. ESI mass spectrometry was collected at facilities at South Dakota State University, University of Oklahoma, or University of Buffalo. IR spectra were recorded on a BioRad FT-155FT-IR spectrometer (using dichloromthane as solvent). Melting points were determined by using a MEL-TEMP® Electrothermal instrument. Elemental analyses were performed at Atlantic Microlab, Inc. HPLC analysis was performed with HP Agilent 1100 [Column: Thermo Fisher Scientific, Hypersil, BDS 5 μm, C18 column, 5 μm particle size, 250 mm length×4.6 mm inner diameter; Mobile phase: 90/10 (acetonitrile/water); Flow rate: 1 mL/min; Detection: 254 nm]. Photooxidation of olefins were performed using 690 nm diode laser (model #: MRL-690(FC), Changchun New Industries).

4-((1,2-Dichlorovinyl)oxy)-1,1'-biphenyl (2)

To a two-necked, round bottom flask (250 mL) equipped with a magnetic stirrer, pressure equalizing funnel and rubber septum was suspended oil free potassium hydride (2.23 g, 55 mmol, 1.5 eq) in tetrahydrofuran (THF, 25 mL). 4-Phenylphenol (6.30 g, 37 mmol, 1 eq) in THF (50 mL) was then added drop-wise with stirring for over 20 min via the funnel. After the evolution of hydrogen was complete, the orange-yellow slurry was cooled to −78° C., and then treated with drop-wise solution of trichloroethylene (5.8 g, 44 mmol, 1.2 eq) in THF (25 mL) for over 10 min. The cooling bath was removed and the reaction mixture was allowed to warm to room temperature (rt) and then maintained for overnight (12 h). To the dark brown mixture was carefully added water (10 mL) using a syringe and then partitioned between water (200 mL) and ethyl acetate (200 mL). The organic phase was then washed with brine (200 mL). Extraction of the combined aqueous layers was done using ethyl acetate (150 mL×3). The combined organic phases were dried over anhydrous magnesium sulfate, filtered and concentrated using the rotary evaporator to give yellowish brown oil. Silica gel (200 g) column chromatography was done using hexane as eluent to afford 2 (10.5 g, 85%) as colorless oil that later crystallized to white crystals: mp 52-55° C. $^1$H NMR (300 MHz, CDCl$_3$): 7.62-7.54 (m, 4H, HAr), 7.48-7.41 (m, 2H, HAr), 7.39-7.32 (m, 1H, HAr), 7.18-7.12 (m, 2H, HAr), 6.00 (s, 1H, HC(Cl)=C(O)) ppm; $^{13}$C NMR (75 MHz, CDCl$_3$): 153.3, 140.2, 137.8, 128.8, 128.5, 127.3, 127.0, 117.4, 103.9 ppm; IR (cm$^{-1}$): 3105, 3031, 1898, 1658, 1630, 1603, 1585, 1543, 1310, 1203, 1184, 1107, 1074, 1008, 996, 915, 863, 840, 641, 547, 511; HRMS (ESI) Calculated for C$_{14}$H$_{10}$Cl$_2$O [M−H]$^-$ 263.0031. Found 263.0030. Elemental analysis Calculated. for C$_{14}$H$_{20}$Cl$_2$O.0.02H$_2$O: C, 63.33; H, 3.81. found: C, 63.34; H, 3.79.

4-(Ethynyloxy)-1,1'-biphenyl (3)

To a two-necked, round-bottomed flask (100 mL) equipped with a nitrogen inlet adapter and rubber septum was added the vinyl ether 2 (2.0 g, 7.6 mmol, 1 eq), anhydrous diethyl ether (30 mL), and TMEDA (23 mmol, 3.3 mL, 3 eq), and then cooled at −78° C. 2.5 M n-Butyllithium (9.0 mL, 23 mmol, 3 eq) was then added drop-wise to the reaction mixture for over 5 min. The reaction mixture was then maintained at −78 C for 1 h and at −40° C. for 40 min, and then cooled to −78° C. while 10% ethanol in pentane (10 mL) was added drop-wise. After 10 min, the reaction mixture was then diluted with n-pentane (20 mL) and the washed with saturated solution of ammonium chloride (25 mL). The organic phase was later washed twice with water (20 mL) and then finally with brine (20 mL), dried over anhydrous sodium sulfate, filtered and concentrated to give brown oil. The oil was purified by column chromatography with hexane as the eluent to yield 3 as dark brown oil (0.84 g, 70%) that later crystallized out as brown amorphous solid: mp 48-49° C. The compound was placed in a round bottom flask and was flushed with nitrogen and kept at −78° C. to avoid the decomposition if it was not to be used immediately. $^1$H NMR (300 MHz, CDCl$_3$): 7.64-7.52 (m, 4H, HAr), 7.48-7.41 (m, 2H, HAr), 7.40-7.34 (m, 3H, HAr), 2.13 (s, 1H, ≡—H) ppm; $^{13}$C NMR (75 MHz, CDCl$_3$): 155.0, 140.1, 138.0, 128.9, 128.4, 127.4, 127.0, 115.4, 84.5, 33.5 ppm; IR (cm$^{-1}$): 3317 (≡C—H), 3029, 2927, 2174 (C≡C), 1606, 1512, 1484, 1208, 1166, 1062, 1008, 941, 838, 641, 548, 450; HRMS (ESI) Calculated for C$_{14}$H$_{10}$O [M−H]$^-$ 193.0654. Found 193.0651. Elemental analysis Calculated. for C$_{14}$H$_{10}$O.0.13H$_2$O: C, 85.54; H, 5.26. found: C, 85.54; H, 5.38.

(E)-4-((2-Iodovinyl)oxy)-1,1'-biphenyl (4)

To an oven dried, two-necked flask (250 mL) under nitrogen and protected from light was added Cp$_2$ZrCl$_2$ (5.2 g, 20.3 mmol, 2 eq), dry THF (30 mL), and 1M lithium triethylborohydride (Super Hydride) in THF (20 mL, 20 mmol, 1.9 eq). The mixture was stirred for 1 h where the alkyne 3 (1.97 g, 10.2 mmol, 1 eq) was added. After 30 min, iodine (2.57 g, 20.3 mmol, 2 eq) was added and the reaction mixture was stirred for 30-40 min while protected from light. The reaction was quenched by diluting with ethyl acetate/hexane (1:1, 50 mL). The diluted mixture was then washed twice with saturated solution of sodium bicarbonate (150 mL) and the combined aqueous layers were extracted with ethyl acetate/hexane mixture (1:1). 10% aqueous sodium thiosulphate (100 mL) was used to wash the combined organic phases followed by brine (100 mL), dried over sodium sulfate, filtered, concentrated to yellowish slurry which was purified by silica gel column chromatography using 100% hexane as eluent (silica gel was pretreated with 2.5% v/v triethylamine) to afford 4 as white amorphous crystals (1.80 g, 55%): mp 64-66° C. $^1$H NMR (300 MHz, CDCl$_3$): 7.64-7.52 (m, 4H, HAr), 7.49-7.41 (m, 2H), 7.38-7.32 (m, 1H, HAr), 7.13-7.01 (m, 3H, HAr), 5.74 (s, 1H, CH=CH, J=12.2 Hz) ppm; $^{13}$C NMR (75 MHz, CDCl$_3$): 155.5, 150.3, 140.3, 137.0, 128.9, 128.4, 127.2, 126.9, 117.5, 57.9 ppm; IR (cm$^{-1}$): 3316, 3077, 3034, 2960, 2924, 2874, 2174, 1643, 1623, 1601, 1515, 1485, 1330, 1307, 1226, 1186, 1173, 1093, 1008, 919, 854, 837, 697, 579, 549.

General procedure for coupling reactions using 2-pyridin-2yl-1H-benzoimidazole (L2): (E)-4-((2-(Phenoxy) vinyl) oxy)-1,1'-biphenyl (5): An oven dried, three-necked, round-bottomed flask (50 mL) equipped with a nitrogen inlet, reflux condenser, rubber septum was repeatedly evacuated and back-filled with dry and pure nitrogen, and was then charged with CuI (0.074 g, 0.39 mmol, 0.5 eq), L2 (0.076 g, 0.39 mmol, 0.5 eq) and Cs$_2$CO$_3$ (0.63 g, 2.0 mmol, 2.5 eq), followed by addition of DMF (2 mL). The solution was stirred for 10 min at rt until reaction turn light green color. The appropriate substrate phenol (0.073 g, 0.78 mmol, 1 eq) was added to the reaction mixture and then stirred for addition 5 min at rt. Compound 4 (0.25 g, 0.78 mmol, 1 eq) was dissolved in minimum amount of solvent and then added into the reaction mixture. The reaction mixture was then heated from rt to between 50-75° C. for 12-36 h depending on the substrate. The reaction mixture was cooled and then through pad of silica gel using ethyl acetate and hexane mixture (20:80, 100 mL) and then washed three times with the same solvent mixture (100 mL). Filtrate was washed with water (100 mL×3) followed with brine (200 mL), dried using anhydrous sodium sulfate and concentrated in vacuo to yield brown oil. The crude oil was then purified by silica gel column chromatography using 100% hexane to afford 5 as white crystals. (0.18 g, 70%): mp 60-63° C. $^1$H NMR (300 MHz, CDCl$_3$): 7.59-7.54 (m, 4H, HAr), 7.47-7.40 (m, 2H, HAr), 7.37-7.31 (m, 1H, HAr), 7.16-7.03 (m, 7H), 6.92 (s, 2H, HC=CH); $^{13}$C NMR (75 MHz, CDCl$_3$): 157.6, 157.2, 140.4, 135.8, 134.9, 134.6, 129.7, 128.8, 128.4, 127.0, 126.9, 122.7, 116.0, 115.8; IR (cm$^{-1}$): 3061, 2962, 2870, 1606, 1510, 1485,1419, 1365, 1230, 1183, 1174, 1124, 1105, 1006, 896, 836, 728; HRMS (ESI), Calculated for C$_{20}$H$_{16}$O$_2$ [M–H]$^-$ 287.1072. Found 287.1053; HPLC analysis: 91% purity.

General procedure for coupling reactions using trans-N-(2-pyridylmethylene)aniline (L1): (E)-4-((2-(4-(Tert-butyl) phenoxy)vinyl)oxy)-1,1'-biphenyl (6): An oven dried, three-necked, round-bottomed flask (50 mL) equipped with a nitrogen inlet, reflux condenser, rubber septum was repeatedly evacuated and back-filled with dry and pure nitrogen, and was then charged with CuI (0.095 g, 0.5 mmol), L1 (0.09 g, 0.5 mmol), tert-butyl phenol (0.18 g 1.2 mmol), and Cs$_2$CO$_3$ (0.81 g, 2.5 mmol), followed by the addition of anhydrous and degassed acetonitrile (1.2 mL). The flask was evacuated and back-filled with nitrogen and compound 4 (0.32 g, 1 mmol) added at rt. The reaction mixture was stirred and heated to the required temperature of 80° C. for the 48 h. After cooling to rt, the mixture was diluted with dichloromethane (20 mL) and filtered through a plug of celite, with the filter cake being further washed with dichloromethane (10 mL). The filtrate was washed with saturated NH$_4$Cl (15 mL), and twice with water (10 mL). The collected aqueous phases were extracted twice with dichloromethane (10 mL). The organic layers were collected, dried over MgSO$_4$, filtered, and concentrated in vacuo to yield brown solid. The crude product was fixed with 6 g silica gel and then purified by silica gel chromatography (100% hexane) to afford 6 a white solid (0.20 g 65%): mp 59-62° C. $^1$H NMR (300 MHz, CDCl$_3$) 7.59-7.52 (m, 4H, HAr), 7.46-7.40 (m, 2H, HAr), 7.38-7.33 (m, 3H, HAr), 7.15-7.09 (d, 2H, J=8.5 Hz, HAr), 7.02-6.97 (d, 2H, J=8.6 Hz), 6.91 (s, 2H, CH=CH), 1.32 (s, 9H, 3× —CH$_3$) ppm; $^{13}$C NMR (75 MHz, CDCl$_3$) 157.2, 155.3, 145.6, 140.6, 135.7, 135.3, 134.2, 128.8, 128.4, 127.0, 126.8, 126.5, 116.0, 115.3, 34.3, 31.5 ppm; IR (cm$^{-1}$): 3052, 2961, 2931, 2867, 1607, 1512, 1487, 1367, 1298, 1229, 1187, 1127, 1105, 1079, 1006, 839, 723; HRMS(ESI), Calculated for C$_{24}$H$_{24}$O$_2$ [M+H]$^+$ 345.1854. Found 345.1849. Elemental analysis Calculated. for C$_{24}$H$_{24}$O$_2$·1.25H$_2$O: C, 78.55; H, 7.01. found: C, 78.55; H, 7.27.

(E)-4-[2-(4-Methoxyphenoxy)vinyloxy]biphenyl (7)

Compound 7 was prepared according to the general method described for compound 6 above, employing 4 (0.2 g, 0.62 mmol, 1 eq) and 4-methoxyphenol (0.077 g, 0.62 mmol, 1 eq), Cs$_2$CO$_3$ (0.50 g, 1.6 mmol, 2.5 eq), CuI (0.59 g, 0.31 mmol, 0.5 eq) and L1 (0.057 g, 0.31 mmol, 0.5 eq) heating the reaction mixture at 80° C. for 48 h to furnish the crude product which was purified by column chromatography using hexane as the eluent to afford 7 as white crystals (40 mg, 40%): mp 112-115° C. $^1$H NMR (300 MHz, CDCl$_3$): 7.61-7.52 (m, 4H, HAr), 7.47-7.40 (m, 2H, HAr), 7.36-7.30 (m, 1H, HAr), 7.10 (d, 2H, J=8.6 Hz), 7.00 (d, 2H, J=9.0 Hz), 6.91-6.84 (m, 4H, HAr and HC(O)=C(O)H), 3.80 (s, 3H, —CH$_3$) ppm. $^{13}$C NMR (75 MHz, CDCl$_3$): 156.3, 154.3, 150.5, 139.5, 135.6, 135.1, 132.7, 131.4, 129.0, 127.8, 127.3, 125.8, 116.1, 115.0, 113.8, 54.7 ppm; IR (cm$^{-1}$): 3059, 1658, 1605, 1517, 1485,1420, 1319, 1264, 1226, 1173, 1122, 896, 838, 737, 639; HRMS(ESI), Calculated for C$_{21}$H$_{18}$O$_3$ [M–H]$^-$ 317.1178. Found 317.1158; HPLC analysis: 92% purity.

(E)-(2-([1,1'-Biphenyl]-4-yloxy)vinyl)(phenyl)sulfane (8)

The compound 8 was prepared according to the general procedure described for the compound 6 above employing 4 (0.15 g, 0.47 mmol, 1 eq) and thiophenol (0.051 g, 0.05 mL, 0.47 mmol, 1 eq), Cs$_2$CO$_3$ (0.38 g, 1.2 mmol, 2.6 eq), CuI (0.044 g, 0.23 mmol, 0.49 eq) and L1 (0.042 g, 0.23 mmol, 0.49 eq) heating the reaction mixture at 60° C. for 10 h to give crude product, which was purified by silica gel column chromatography (100% hexane) to give compound 8, as white crystals (0.12 g, 90%). [When a mixture of Z and E-4 (1:9) was used as the starting material under same conditions at a temperature above 100° C. afforded a mixture of Z and E-8 (1:9). They were distinguished from each other by their coupling constants. J$_{cis}$=5.7 Hz while J$_{trans}$=12 Hz ($^1$H-NMR data of these mixtures are found below).] The characterization data below is that of 8 obtained from the reaction 4 with thiophenol: mp 92-96° C. $^1$H NMR (300 MHz, CD$_2$Cl$_2$): 7.66-7.54 (m, 4H, HAr), 7.48-7.40 (m, 2H, HAr), 7.37-7.28 (br s, 6H, HAr), 7.20-7.09 (m, 3H, HAr), 6.09-6.10 (d, 2H CH=CH, J=12.0 Hz) ppm; $^{13}$C NMR (300 MHz, CDCl$_3$): 155.9, 150.6, 140.3, 137.5, 137.1, 128.9, 128.8, 128.5, 127.2, 127.0, 126.9, 125.7, 117.4, 102.1; IR (cm$^{-1}$): 3054, 2985, 1659, 1624, 1599, 1515, 1485, 1265, 1233, 1185, 1174, 1112, 1086, 1025, 1007, 924, 839, 739, 407; HRMS (ESI) Calculated for $C_{20}H_{16}OS$ [M+H]$^+$ 305.1000. Found 305.0998; Elemental analysis Calculated for $C_{20}H_{16}OS0.11H_2O$: C, 78.40; H, 5.34. found: C, 78.40; H, 5.29.

(E)-1-(2-([1,1'-Biphenyl]-4-yloxy)vinyl)-1H-indole (9)

The compound 9 was prepared following the procedure described for 5 with 4 (0.32 g, 1 mmol, 1 eq), indole (0.14 g, 1.2 mmol, 1.2 eq), $Cs_2CO_3$ (0.81 g, 2.5 mmol, 2.5 eq), CuI (0.095 g, 0.5 mmol, 0.5 eq) and L2 (0.097 g, 0.5 mmol, 0.5 eq) at 70° C. for 12 h to give crude product which were purified by silica gel column chromatography using ethyl acetate-hexane (9:95) to afford compound 9 as white crystals (0.27 g, 87%): mp 140-142° C. $^1$H NMR (300 MHz, CDCl$_3$): 7.58-7.46 (m, 6H, HAr), 7.40-7.32 (m, 3H, HAr), 7.25-7.21 (m, 1H, HAr), 7.20-7.14 (m, 2H, HAr), 7.12-7.02 (m, 4H, HAr and H(O)C=(N)CH), 6.55 (d, H, J=3.1 Hz, HAr). $^{13}$C NMR (75 MHz, CDCl$_3$): 156.8, 140.4, 136.5, 136.4, 128.9, 128.8, 128.5, 127.1, 126.9, 125.7, 125.6, 121.2, 120.5, 116.5, 115.2, 109.8, 104.0 ppm; IR (cm$^{-1}$): 3034, 2358, 2338, 1682, 1606, 1515, 1485, 1475, 1462, 1358, 1333, 1322, 1301, 1232, 1202, 1186, 1174, 1134, 1115, 1088, 1031, 1007, 907, 865, 834; HRMS (ESI), Calculated for $C_{22}H_{17}NO$ [M+H]$^+$ 312.1388; Found 312.1381. Elemental analysis Calculated for $C_{22}H_{17}NO.0.25H_2O$: C, 83.65; H, 5.58; N, 4.43. found: C, 83.61; H, 5.65; N, 4.01.

(E)-1-[2-(Biphenyl-4-yloxyl)vinyl]-1H pyrrole (10)

The compound 10 was prepared following the procedure described for 5 with 4 (0.2 g, 0.62 mmol, 1 eq), pyrrole (0.062 g, 0.93 mmol, 1.5 eq), $Cs_2CO_3$ (0.40 g, 1.2 mmol, 2.5 eq), CuI (0.059 g, 0.31 mmol, 0.5 eq) and L2 (0.060 g, 0.31 mmol, 0.5 eq) at 70° C. for 12 h to give crude product which were purified by silica gel column chromatography using ethyl acetate-hexane (9:95) to afford compound 10 as white crystals (0.14 g, 85%): mp 102-105° C. Olefinic protons coupling on the named compound gave an AB-system with a typical roof effect with peaks centered at 7.04 and 6.99 ppm. $^1$H NMR (300 MHz, CDCl$_3$): 7.62-7.53 (m, 4H, HAr), 7.48-7.40 (m, 2H, HAr), 7.38-7.31 (m, 1H, HAr), 7.17-7.09 (m, 2H, HAr), 7.04 (distorted d, 1H, J=11.1 Hz, (O)—CH=CH(N)), 6.99 (distorted d, 1H, J=11.1 Hz, (O)—CH=CH(N)), 6.82 (dd, 2H, J$_1$=4.2 Hz, J$_2$=2.2 Hz, CH=CH of pyrrole), 6.28 (dd, 2H, J$_1$=4.2 Hz, J$_2$=2.2 Hz, CH=CH); $^{13}$C NMR (75 MHz, CDCl$_3$): 156.8, 140.4, 136.3, 135.0, 128.8, 128.4, 127.1, 126.9, 119.6, 118.3, 116.5, 110.0 ppm; IR (cm$^{-1}$): 3086, 3034, 2715, 2682, 1659, 1607, 1587, 1517, 1485, 1360, 1326, 1300, 1239, 1229, 1185, 1173, 1119, 1094, 1072, 1056, 1007, 975, 907, 857, 838, 614; HRMS (ESI) Calculated for $C_{18}H_{15}NO$ [M+H]$^+$ 262.1232. Found 262.1233. Elemental analysis calculated for $C_{18}H_{15}NO.0.17H_2O$: C, 81.77; H, 5.85; N, 5.29. found: C, 81.76; H, 5.91; N, 5.03.

General Photooxidation Procedure:

In a NMR tube, an olefin (0.0048 mmol) was dissolved in CDCl$_3$ (0.5 mL). The photosensitizer [5-(4-methoxyphenyl)-10,15,20-triphenyl-21-23-dithiaporphyrin, CMP-OMe, 3 mg, 0.0048 mmol] was added to this solution. Then, the reaction mixture was irradiated for 15 min using a diode laser (690 nm, 200 mW/cm$^2$). The reaction of olefins with singlet oxygen was monitored by the decrease of olefinic peaks in $^1$H-NMR spectra. The formation of the photooxidation products were also determined by appearance of the formate (or thioformate) peaks in $^1$H-NMR spectra.

Results and Discussion of Example 2

For the synthesis of the 1,2-diheteroatom-substituted olefins (See Scheme 3), four-step scheme was developed where 4-phenylphenol 1 was used in one side. First, 4-phenylphenol was vinylated using 1,1,2-trichloroethylene[45] to give the corresponding 4-((1,2-dichlorovinyl)oxy)-1,1'-biphenyl 2 with yield of more than 85%.[46,47] Then, 4-(ethynyloxy)-1,1'-biphenyl 3 was prepared by elimination reaction using n-BuLi in 70% yield.[46,47] Although 1 was used in this paper, other types of alcohols and phenols can also be converted to the alkyne form.[46] Hydrozirconation and iodinolysis of 3 led to 2-iodoenol ether 4 in 55% yield.[48,49] Using the copper-catalyzed coupling reaction, 4 were linked with various substrates bearing the different functional groups.[36,50,51]

The reaction with thiophenol gave the best yield (8: 90%) and short reaction time followed by reactions with aromatic amines (9: 87%, 10: 85%) and least yield by the reaction with phenols (compounds 5, 6, and 7). The trend could be explained by the relative nucleophilicity of the substrates (—SH>—NH>—OH) (Table 2). Two coupling conditions were used; either trans-N-(2-pyridylmethylene)aniline as ligand in acetonitrile as solvent[36,52] or 2-pyridin-2-yl-benzoimidazole as ligand in DMF as solvent.[51] For the compound 5, slightly better yields were obtained using the latter coupling condition and the reaction time was reduced to 16 hr compared to the former condition (36 h). To test the robustness the method, some selected analogues of the phenolic and azole derivatives were synthesized. Phenolic derivatives required high temperatures of 70-80° C. for 16-48 h of reaction time and yields were poor-good (40-70%). Further optimization of reaction conditions for these low yielding coupling reactions will be pursued. Reaction with the azole derivatives required low temperatures between 50-75° C. and shorter reaction time, 12 h. The yields for 9 and 10 were very good (87 and 85% respectively). The methodology encountered, however, a limitation in the case of aniline. Coupling using aniline substrate gave an extremely low yield that the product could not be isolated. In all of these reactions the products gave single isomers (E-1,2-diheteroatom-substituted olefins) since only the 4 was used for the coupling.[51] This is well-known Ullmann-type coupling reaction which proceed in stereo-specific fashion.[50,51] The stereospecificity of the reaction was also supported by the fact that a mixture of E/Z-4 (9:1) at >100° C. gave a mixture of E/Z-8 at the same ratio of 9:1 (NMR data in SI).

Unlike typical coupling constants of 12-18 Hz for protons at E-olefins and 6-12 Hz at Z-counterparts, the coupling constants of the hydrogen atoms on 1,2-diheteroatom-substituted olefins were found to be reduced and in some cases even to zero. Only a peak was observed from 1,2-diaryloxy-alkenes (5, 6, and 7) where the two olefinic protons are in very similar environment. On the other hand, while 8 showed doublet peaks, 10 showed distorted doublet peaks (AB system): E-8 (J=12 Hz), Z-8 (J=5.3 Hz), E-10 (J=11.1 Hz). Such unusual small coupling constants of olefins were also observed in monohetereoatom-substituted olefins, especially the oxygen-substituted olefins.[36,50,51]

To examine the oxidation rate of these electron-rich alkenes with singlet oxygen (Scheme 4), compounds 6, 8, and 10 were irradiated in the presence of 5-(4-methoxyphenyl)-10,15,20-triphenyl-21,23-dithiaporphyrin as a photosensitizer.[53] All experiments were performed following the standard procedure previously set with a slight modification by using a 690 nm diode laser source (200 mW/cm$^2$).[35] In the experiments, the amount of sensitizer used was not catalytic. Here, the ratio of olefin and photosensitizer used was 1:1 to mimic the situation of prodrug where the olefinic linker could be used for connecting one drug molecule to one photosensitizer molecule.[7,35] The reaction solutions were irradiated for 15 min and monitored every 5 min using olefinic peaks in $^1$H-NMR each time to monitor the progress of the reactions. Upon the oxidation by singlet oxygen, the olefinic peaks decreased.

TABLE 2

Copper-catalyzed vinylation of nucleophiles.

| Product | Substrate (HXR) | Ligand [rx. temp (° C.), time (h)] | Yield (%) |
|---|---|---|---|
| 5 | phenol (PhOH) | L1 [a] (75, 36) / L2 [b] (75, 16) | 65 / 70 |
| 6 | 4-tert-butylphenol | L1 (80, 48) | 65 |
| 7 | 4-methoxyphenol | L1 (80, 48) | 40 |
| 8 | thiophenol (PhSH) | L1 (60, 10) | 90 |
| 9 | indole | L2 (70, 12) | 87 |
| 10 | pyrrole | L2 (65, 12) | 85 |

[a] L1 = trans-N-(2-pyridylmethylene)aniline
[b] L2 = 2-pyridin-2-yl-benzoimidazole

TABLE 3

Time-dependent decrease of the olefins and formation of photoproducts.

| Time (min) | Remaining olefins (%) | | | | Observed product (%) | | | |
|---|---|---|---|---|---|---|---|---|
| | control | 6 | 8 | 10 | Ca | (6a + 6b)/2* | 8a | 8b |
| 0 | 100 | 100 | 100 | 100 | 0 | 0 | 0 | 0 |
| 5 | 38 | 26 | 29 | 27 | 0 | 53 | 67 | 32 |
| 10 | 11 | 2 | 0 | 0 | 1 | 87 | 99 | 48 |
| 15 | 0 | 0 | 0 | 0 | 2 | 92 | 99 | 48 |

In $^1$H-NMR, the formate peaks of expected products of 6 (6a and 6b) were too close to be distinguished. Thus, two peaks were integrated together and divided by 2.

Figure 4:
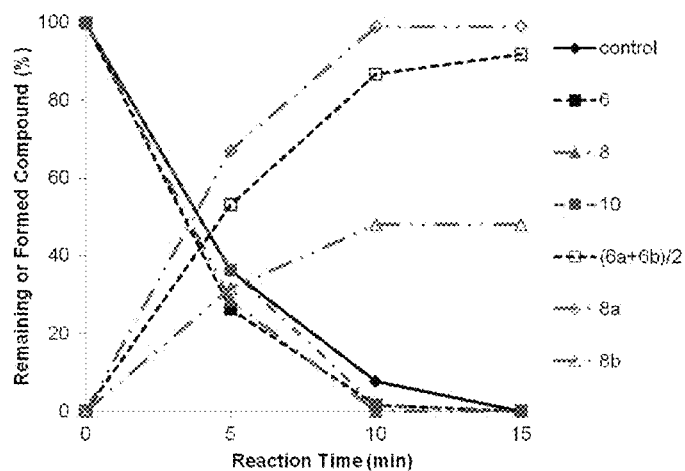
FIG. 4 graphically depicts the photooxidation of olefins (6, 8, and 10 of Scheme 4) by the irradiation of 690 nm diode laser at 200 mW/cm$^2$ with a photosensitizer (CMP-OMe) in chloroform-d.

(Z)-1,2-Bis(phenylthio)ethylene was used as a control against which the reaction rates were compared. Analysis of the data indicated that not much difference exists amongst these linkers with respect to their rate of reaction with singlet oxygen (FIG. 4 and Table 3). Double bond peaks of all the four substrates disappeared within 15 min of the irradiation. The fast reaction of 6 (1,2-diaryloxyalkene) and 8 (1-aryloxy-2-arylthio-alkene) is consistent with that previously reported.[35] The cleaved formate products 6a, 6b, and 8a were formed consistent with the decrease of the olefins 6 and 8 (Table 3). On the other hand, cleaved thioformate product 8b was formed much less (about half) than oxidized olefin 8 presumably due in part to the oxidation of sulfur atom[14,54] and/or cleavage of carbon-sulfur bond.[55] In the case of control, diphenyl disulfide were also detected after the photooxidation. The fast reaction of 10 (1-aryloxy-2-amino-alkene) with singlet oxygen was also observed. The olefinic peaks of 10 completely disappeared in 10 min. In addition, it was also observed the decrease of the peaks of protons at the pyrrole ring at a little bit slower rate: 73% (olefinic proton) vs. 60% (protons at the pyrrole ring) reduction after 5 min. One notable observation is that the formate product was not detected in the $^1$H-NMR from the oxidation of 10. Photooxidation of pyrrole ring of 10 could produce many possible photoproducts.[56] Further investigation is needed to reveal the detailed mechanism of oxidation of 10.

In summary, a facile and versatile synthesis of E-1,2-diheteroatom-substituted electron-rich alkenes was established. Not only symmetric vinyl diethers but also unsymmetrically heteroatom-substituted olefins could be prepared using phenols, thiols, and N-heterocycles with high stereospecificity. In addition to 1,2-diaryloxyalkene and 1-aryloxy-2-arylthio-alkene, 1-aryloxy-2-amino-alkene also react with singlet oxygen.

Example 3

Click and Photo-Unclick Chemistry of Aminoacrylate for Visible Light-Triggered Drug Release The use of light as an external signal is a very appealing tool for the spatio-temporal release of bio-active molecules. However, applications have been limited mostly to the cellular level due to the use of high energy UV light causing cellular damage and limited tissue penetration (<1 mm).[57] To apply this exciting tool in living animals, new strategies should be invented where active compounds can be released by the tissue penetrable low energy light (preferably, >650 nm).[58] Unfortunately, the energy of longer wavelength light is too low to directly initiate cleavage of most covalent bonds.

Figure 5:
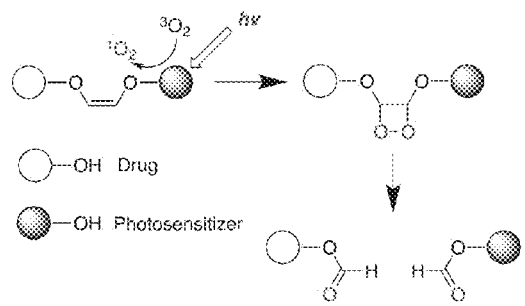
FIG. 5 schematically represents a [2+2] oxidation of vinyl diether by singlet oxygen, and subsequent cleavage of dioxetane for the release of drug.

One clever approach has been proposed by taking advantage of the unique reaction of singlet oxygen that can be generated by the combination of photosensitizer and low energy light. Spontaneous cleavage of dioxetanes following 2+2 cycloaddition reactions of singlet oxygen with olefins has been explored for the site-specific release of bioactive molecules (FIG. 5). Electron rich heteroatom-substituted olefins, such as vinyl dithioethers, vinyl diethers and vinyl monoethers were incorporated in liposomes,[3] cyclodextrin dimers,[6] and prodrugs.[7] However, vinyl mono-ethers might not be the optimum choice for this application due to competition with the ene reaction.[35] On the other hand, the synthetic methods for vinyl diethers and dithioethers are very scarce and the available reaction conditions are not practical due to the low yield and non-stereospecficity.[22,25,59] Another concern of vinyl diether linkers is regeneration of the parent drug. Formyl groups at the cleaved products might attenuate the activity of the drug (e.g., Drug-O—CHO). Here, it is propose aminoacrylates (β-enamino esters) as a new linker for the "click and photo-unclick chemistry" for low energy light-controlled release of active compounds. Adducts can be easily synthesized, cleaved rapidly by visible light, and stable in aqueous media.

Due to the limitations of the previously investigated linkers, a search for new linkers was initiated and attention was turned to β-enamino ketones. In a previous screening, these linkers showed relatively fast photo-oxidation by singlet oxygen (64%, in 60 min).[35] Inspired by the oxidation rate of β-enamino ketone, an analogous of β-enamino esters (compounds 2 and 3, FIG. 6) was designed as new linker candidates that could readily be prepared through high yield reactions (esterification and thiol-yne type reaction).[60,61] The esterification of 4-phenylphenol with propynoic acid was performed by the Steglich esterification with DCC and DMAP at 0° C. (to RT) to give biphenyl propiolate (1).[62] The thiol-yne type reaction of 1 with diethylamine or piperidine gave 2 and 3 in 89% and 80% yields respectively at RT in 10-15 min.

Figure 6:
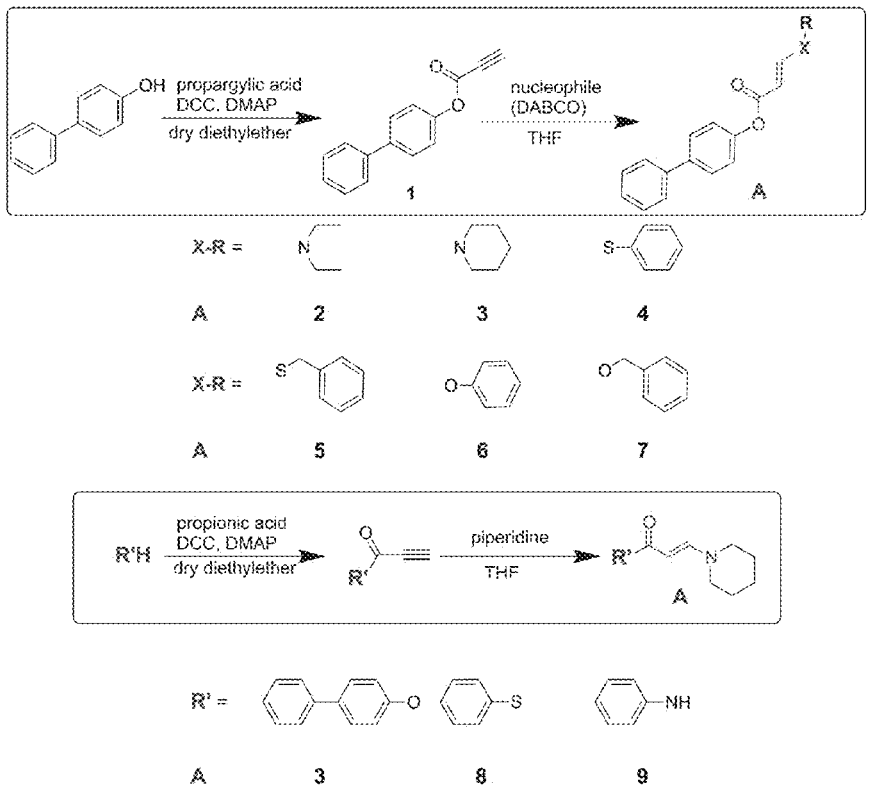
FIG. 6 schematically represents a reaction sequence and prepared substrates for heteroatomacrylate, aminoacrylthioate, and aminoacrylamide. (R'H: 4-phenylphenol, thiophenol, or aniline).

To examine the scope of the preparation and photo-oxidation, analogues were prepared by replacing the nitrogen with sulfur or oxygen [thio-acrylate (4,5) and oxy-acrylate (6,7), or the oxygen with nitrogen or sulfur [aminoacrylthioate (8) and aminoacrylamide (9)] (FIG. 6). These compounds were rapidly prepared under mild reaction conditions (RT, air, 15-20 min), giving excellent yields for all substrates (80-95%). All the products from the click reaction step gave E isomers based on the coupling constant of the two olefinic protons, J=12-15 Hz.

Figure 11:
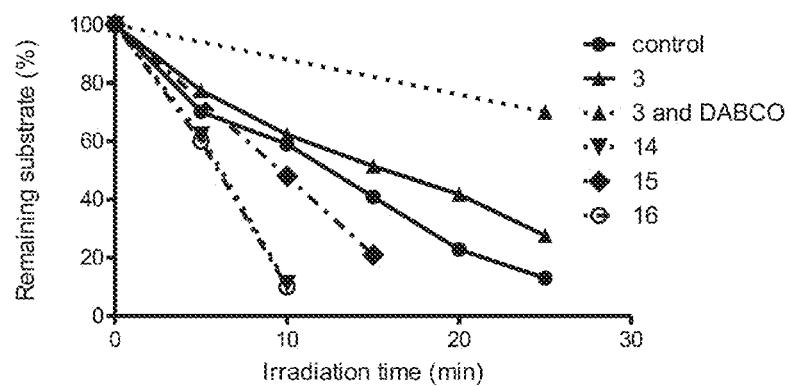
FIG. 11 graphically depicts time-dependent photo-oxidation of model compounds [control=(Z)-1,2-Bis(phenylthio)ethylene].

To evaluate the rate of oxidation by singlet oxygen, the model compounds 2-7 were irradiated by a diode laser (690 nm, 200 mW/cm2, 25 min) in the presence of the photosensitizer 5-(4-methoxyphenyl)-10,15,20-tetraphenyl-21,23-dithiaporphyrin (FIG. 11 and Table 5). The reaction of olefins with singlet oxygen was monitored by the decrease of olefinic proton peaks in the $^1$H-NMR spectra. (Z)-1,2-Bis(phenylthio)ethylene was used as positive control. While 4-7 did not show any reactivity (0%), compounds 2 and 3 showed significant decrease of the olefinic proton peaks (62 and 72%) in 25 min of irradiation. Oxidation of only the nitrogen analogues is probably due to electron donation from the nitrogen to the carbonyl group making the olefinic bond electron rich for attack by singlet oxygen.

The aminoacrylthioate (8) and aminoacrylamide (9) were evaluated under the same oxidation conditions. Interestingly, both 8 and 9 also showed fast reaction with singlet oxygen, 60 and 100%, respectively. Among aminoacrylate (3), aminoacrylthioate (8), and aminoacrylamide (9), compound 9 showed the fastest reaction rate, 100% disappearance of olefinic protons in 25 mins.

From the GC-MS analysis of the cleaved mixture of compound 8, apart from the expected product, thiophenol, diphenyl disulfide was also detected with a number of minor side products. Diphenyl disulfide seemed to be formed during the GC-MS experimental procedure since it was also observed in GC-MS data of thiophenol standard sample (supporting information (SI) below). This conclusion was also supported by the fact that the doublet peak at 7.5 ppm from diphenyl disulfide was not observed in the $^1$H-NMR of the cleaved mixture of 8. Even though 9 showed the fastest reaction with singlet oxygen, it gave even more side products in GC-MS than 8 (SI). However, aminoacrylate linker system (3) was selected for further investigation because it gave the clean product, 4-phenylphenol.

TABLE 5

Percentile of Remaining Compounds 2-16 at Different Time Points During Irradiation (690 nm diode laser, 200 mW/cm$^2$; *not determined)

|  | 0 min | 5 min | 10 min | 15 min | 20 min | 25 min |
|---|---|---|---|---|---|---|
| control | 100 | 70 | 59 | 41 | 23 | 13 |
| 2 | 100 | 83 | 69 | 58 | 51 | 38 |
| 3 | 100 | 77 | 62 | 51 | 42 | 28 |
| 4 | 100 | —* | — | — | — | 100 |
| 5 | 100 | — | — | — | — | 100 |
| 6 | 100 | — | — | — | — | 100 |
| 7 | 100 | — | — | — | — | 100 |
| 8 | 100 | — | — | — | — | 40 |
| 9 | 100 | — | — | — | — | 0 |
| 10 | 100 | — | — | — | — | 60 |
| 11 | 100 | — | — | — | — | 38 |
| 12 | 100 | — | — | — | — | 41 |
| 13 | 100 | — | — | — | — | 50 |
| 14 | 100 | 62 | 11 | — | — | — |
| 15 | 100 | — | 48 | 21 | — | — |
| 16 | 100 | 60 | 10 | — | — | — |

To examine if the cleavage was mediated by singlet oxygen, compound 3 was tested with a singlet oxygen quencher (1,4-diazabicyclo[2.2.2]octane, DABCO) (3 and DABCO, FIG. 11). It was observed that oxidation of the vinylic bond was greatly reduced (72%→31%) suggesting the role of singlet oxygen.

One key requirement for delivery systems is re-generation of the active form of parent molecules after release. However, in the oxidative cleavage of vinyl diether linkers, two formyl products were produced which do not spontaneously decompose to give alcohol products (FIG. 5).[43,44] Interestingly, from the model compound 3, 4-phenylphenol was recovered after the irradiation in addition to one amide product, 1-formyl piperidine. The two products were confirmed by GC-MS analysis (SI).

Since the aminoacrylates 2 and 3 showed fast reaction with singlet oxygen (62 and 72%) at comparable rate with the control (vinyl dithioether), a model for systems 10-13 was further designed with a spacer to accommodate two alcoholic model compounds (e.g., 4-phenylphenol and phenol). All were prepared using high yield click reaction (84-90%). Compounds 11, 12, and 13 showed faster reaction than 10, presumably due to weaker electron withdrawing effect of the ester bond to enamino group in 11 and 12 (Table 5). Using the spacers of 12 and 13, prototypes were prepared (compounds 14 and 15) having both the linker and a photosensitizer (PS) in one molecule. Prototype 14 and 15 were successfully prepared but 15 gave a lower isolated yield (65%) due to the loss in the purification step. Indeed, both showed much faster oxidation reaction (89% in 10 min for 14; and 79% in 15 min for 15) than 12 and 13 even faster than the control (87% in 25 min).

As an example of aminoacrylate linker with a biologically relevant molecule, the model prodrug (compound 16) was prepared from Estrone. It showed a photo-oxidation of 90% in 10 minutes similar to compound 14. The compound 16 successfully released Estrone after irradiation (SI).

Figure 7:
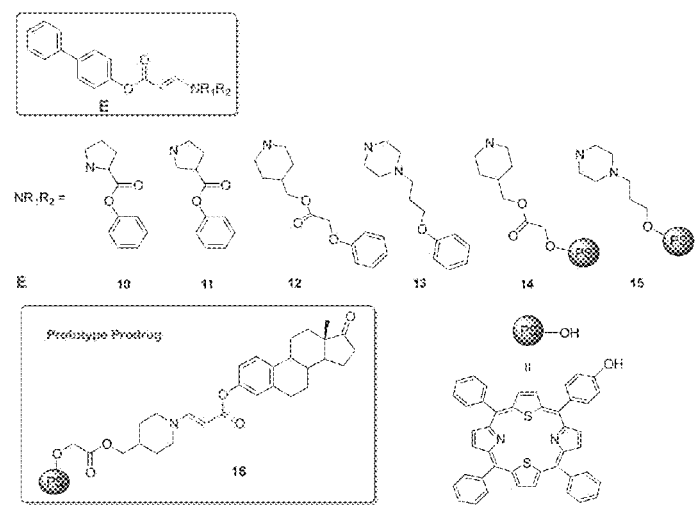
FIG. 7 illustrates prepared model substrates and prototype prodrug of Example 3.
Figure 8:
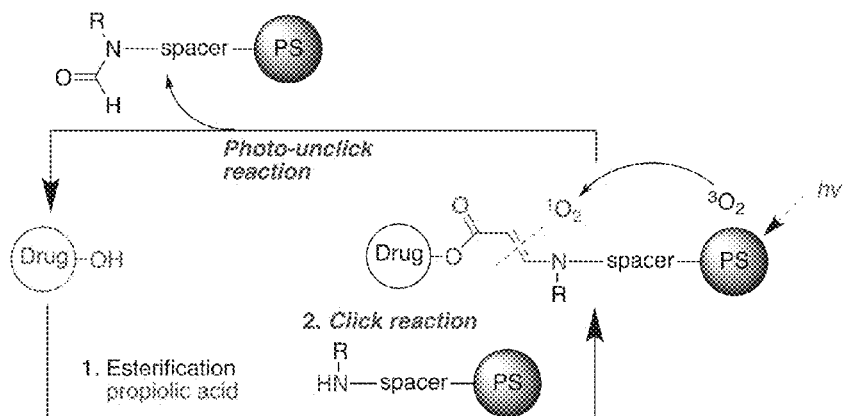
FIG. 8 schematically represents facile synthesis and cleavage of aminoacrylate, and release of a parent drug after its oxidative cleavage.
Figure 9:
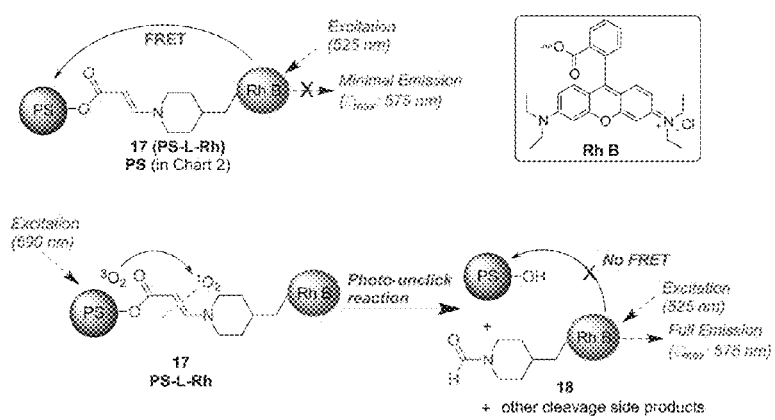
FIG. 9 schematically represents a model compound, PS-L-Rh, for monitoring the cleavage of a linker using FRET.

To examine photo-cleavage and stability of the linker in an aqueous solution (Dulbecco's Modified Eagle Medium with 5% fetal bovine serum) using FRET (fluorescence resonance energy transfer), compound 17 (PS-L-Rh) was designed and prepared by conjugating two dyes [hydroxyl-dithiaporphyrin (PS, FIG. 7) and rhodamine B (Rh B)] with the aminoacrylate linker (FIG. 9).[63] In PS-L-Rh, Rh B is a donor and PS (dithiaporphyrin) is an acceptor of the FRET. Fluorescence ($\lambda_{em}$: 575 nm, excitation at 525 nm) of the Rh group is quenched by the PS group when they are close via the linker. However, once the two dyes are apart after the cleavage of the linker, the fluorescence intensity of Rh group increases dramatically since the FRET is not possible.

Figure 10:
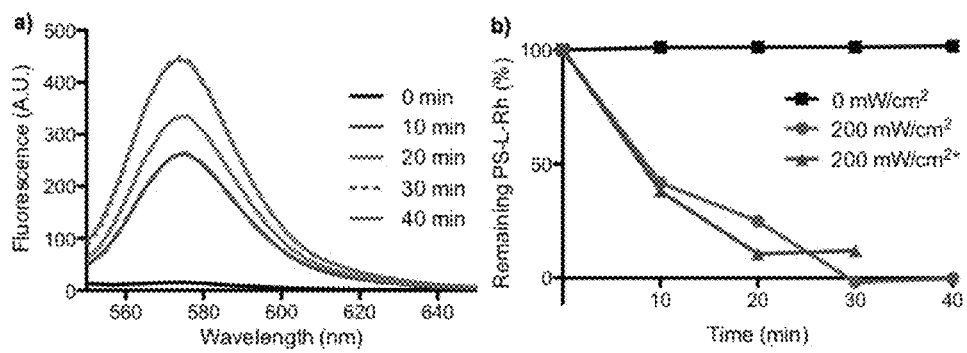
FIG. 10 graphically depicts photocleavage of 17 (from FIG. 9) in media. A: Fluorescence intensity (excitation at 525 nm) after irradiation. B: Photocleavage of 17 with or without irradiation in media. *17 kept 7 days in media under dark before the experiment.

Time-dependent increase of Rh emission upon irradiation (690 nm diode laser at 200 mW/cm2) was first confirmed with PS-L-Rh in CHCl3. Complete (~100%) cleavage was achieved in 10 min, giving about 8-fold increase in Rh fluorescence intensity. This rate is consistent with the cleavage data of 16 (in CDCl3, 90% cleavage in 10 min) monitored by NMR (FIG. 11 and Table 5). The compound 17 successfully released hydroxyl dithiaporphyrin, after irradiation (SI). The conversion yield from 17 to hydroxyl-dithiaporphyrin by photo-unclick reaction seemed high (estimated by TLC, >80%). Then, PS-L-Rh in media was irradiated using the same irradiation conditions. It showed ~100% cleavage in 30 min (FIG. 10). The slower cleavage in medium may be, in part, due to the lower concentration of oxygen (0.27 mM in media vs. 2.4 mM in CHCl3 at atmospheric pressure)[64] and the shorter lifetime of singlet oxygen (2 µs in media vs. 60 µs in CHCl3).[65]

The stability of the aminoacrylate linker of PS-L-Rh in media and CHCl3 was investigated by monitoring the fluorescence emission (575 nm) of Rh group excitation at 525 nm. Up to 7 days, no increase of the Rh emission was observed (<±12%). To ensure the intactness of the linker, the PS-L-Rh kept under dark 7 days was irradiated (690 nm diode laser at 200 mW/cm2), and the fluorescence was determined. It showed similar kinetic data with those of fresh sample (FIG. 10b), indicating that the aminoacrylate was stable in medium at least up to 7 days in the dark.

In conclusion, the concept of "click and photo-unclick chemistry" using nucleophile-yne type reaction and photo-oxidative cleavage of electron-rich olefins using singlet oxygen was proposed and proved. Among aminoacrylate, aminoacrylamide, and amioacrylthioate, aminoacrylate seemed to be best suited for applications for the release of active compounds due to its fast photo-oxidation without unnecessary oxidation products. In addition, it was proven that the aminoacrylate linker was cleaved rapidly by the irradiation of long wavelength visible light (690 nm) and stable under dark in the biological medium. This combination of click and photo-unclick chemistry would find important applications in the spatio-temporal release of not only drugs but also other bioactive molecules. Since the release can be triggered by tissue penetrable low energy light, this simple but unique chemistry will be applicable in the visible light-controlled release of biologically important molecules at the tissue level.

Supplementary Information for Example 3
Synthesis

All solvents and reagents were used as obtained from Sigma Aldrich and Thermo Fisher Scientific unless otherwise stated. All reactions were monitored by GC-MS and/or TLC using 5-17 µm silica gel plates with fluorescent indicators from Sigma-Aldrich. All column chromatography was done using 40-63 µm silica gel from Sorbent Technologies. NMR spectra were recorded at 25° C. using a 400 or 300 MHz Spectrometer. NMR solvents with residual solvent signals were used as internal standards. ESI mass spectral data were collected at facilities at South Dakota State University, University of Oklahoma, or University of Buffalo. GC-MS analyses were performed with HP/agilent 6890A gas chromatograph with an HP/agilent 5973C MSD with EI ion source at the Mass Spectrometry Facility at the University of Oklahoma. UV-Vis and fluorescence data were obtained using Perkin Elmer LAMBDA 25 and LS45 Fluorescence Spectrometer, respectively. Scheme 5 illustrates the synthetic routes of the reagents corresponding to FIGS. 6 and 7, which are selectively described in further detail.

Scheme 5. Synthetic routes of the substrates

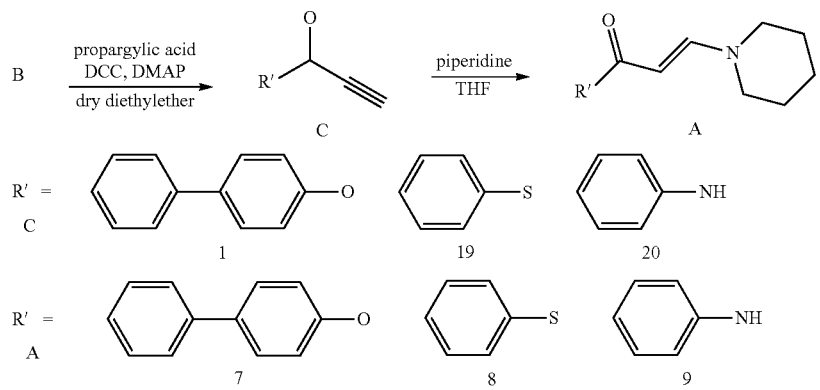

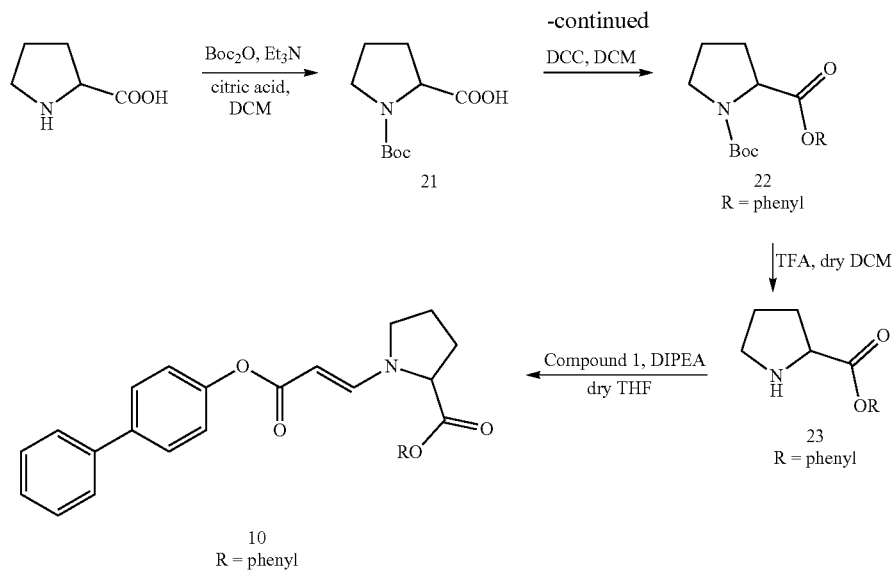
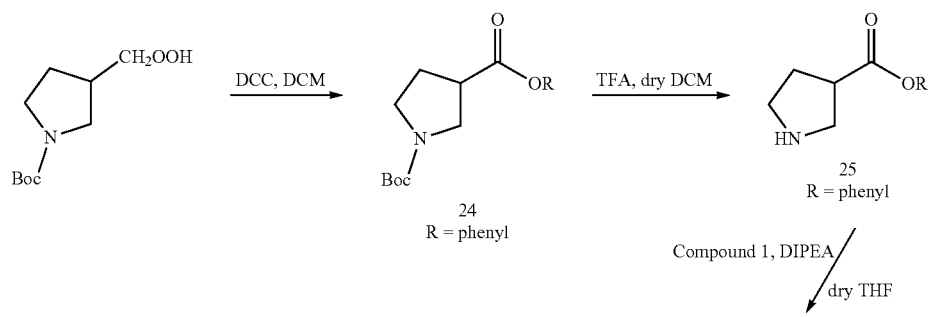
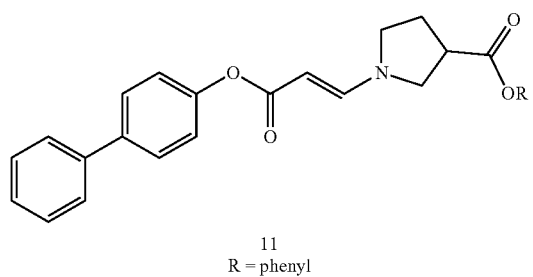
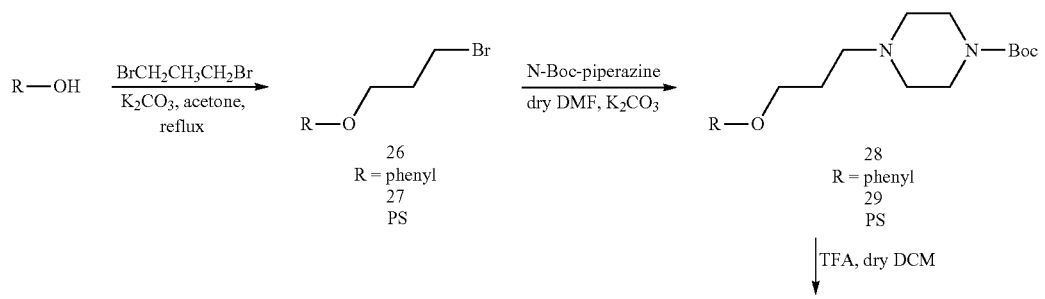

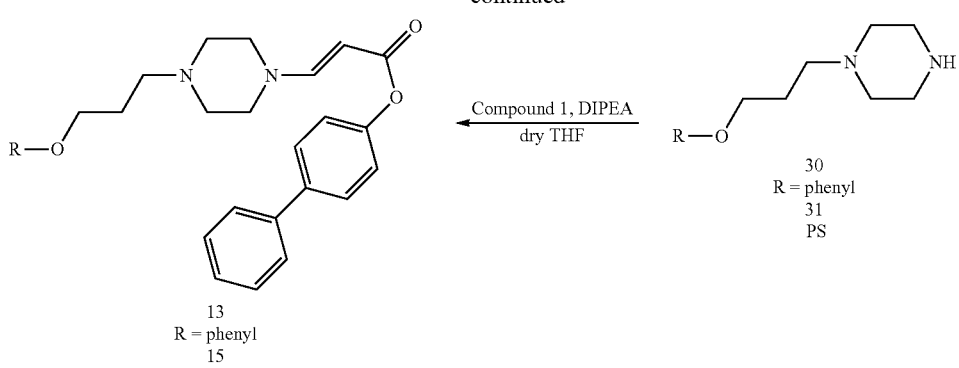
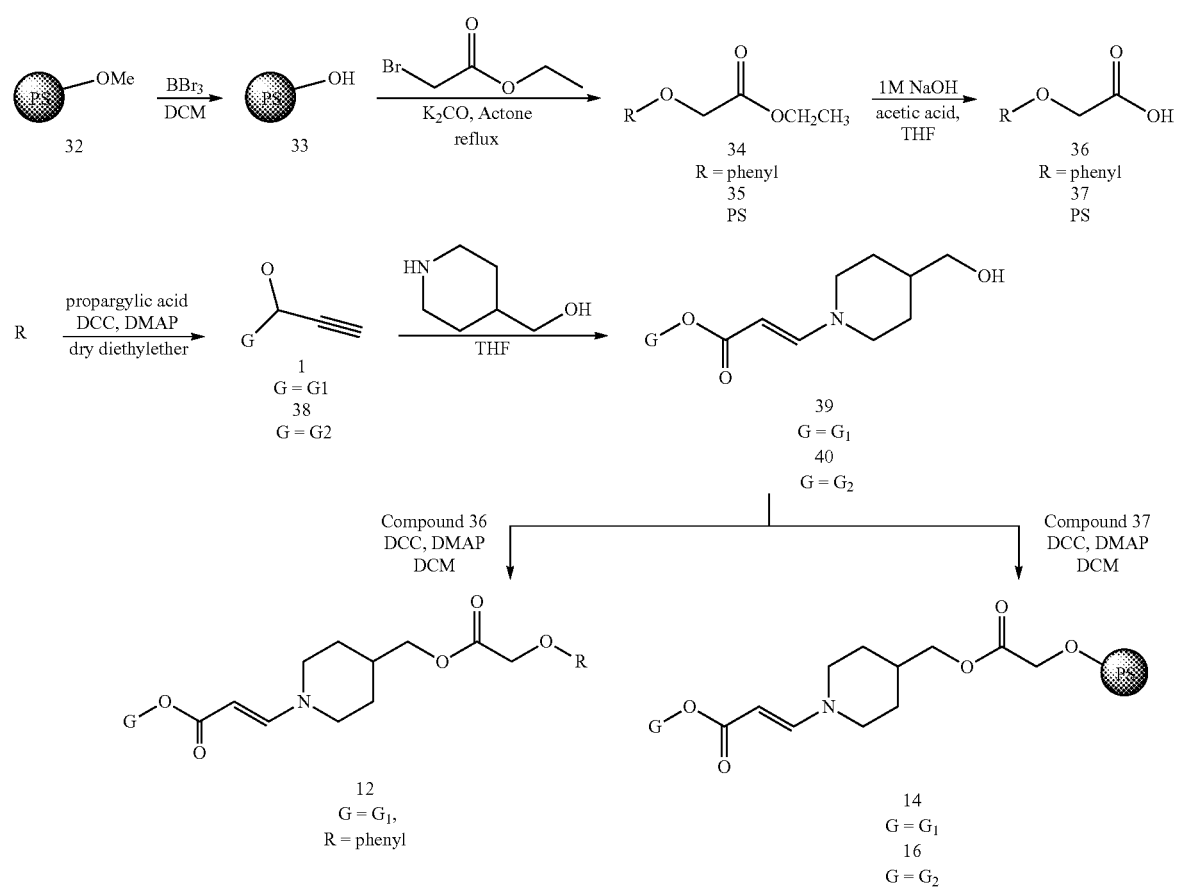
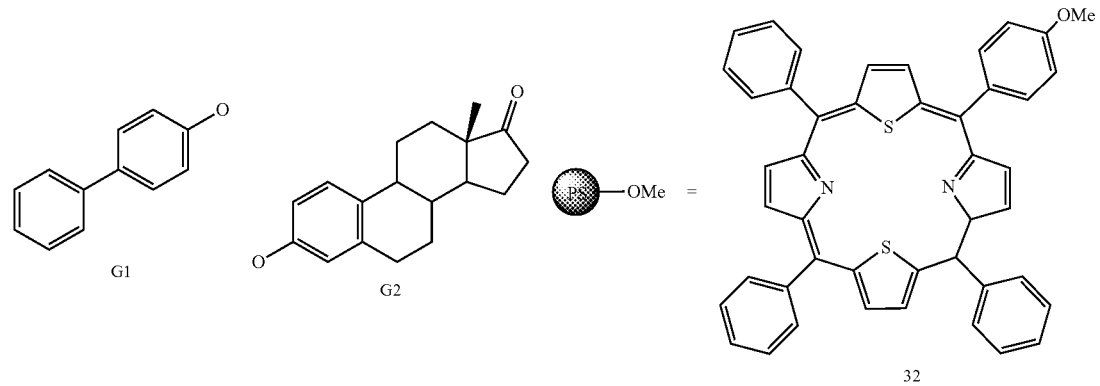

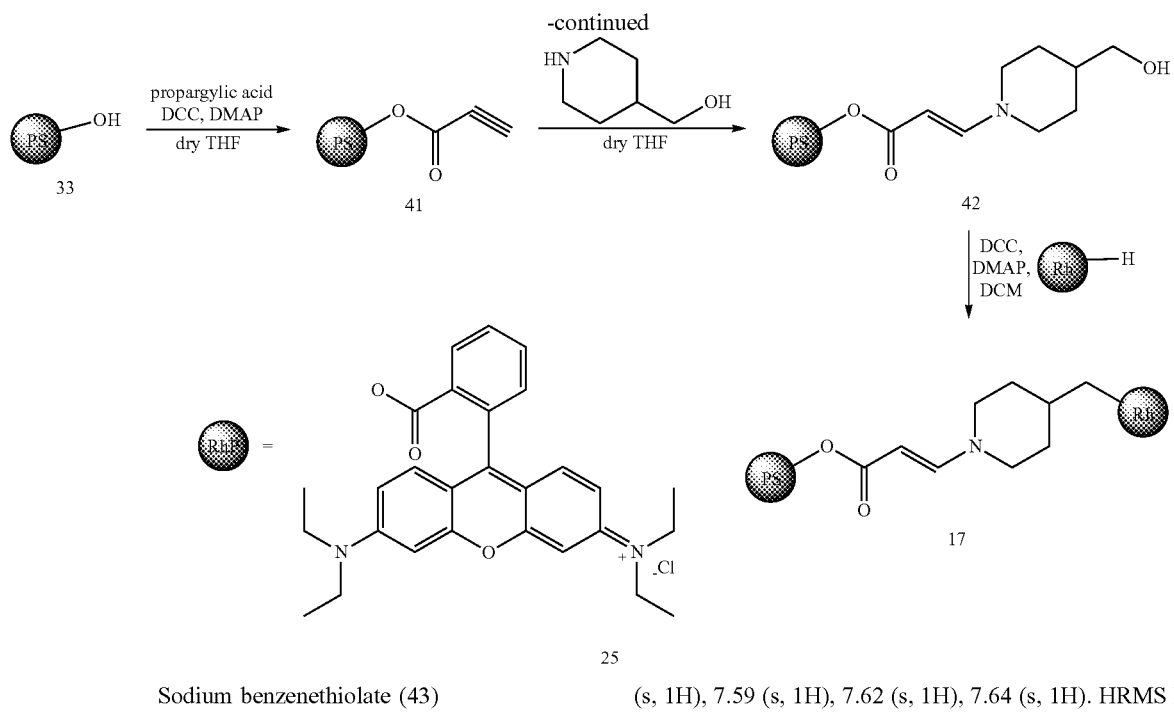

Sodium benzenethiolate (43)

A solution of thiophenol (4.3 g, 39 mmol) in 5 mL of dry diethyl ether was added to a stirring suspension of sodium (0.45 g, 19.5 mmol) in 20 mL of diethyl ether. Stirring was continued until sodium could no longer be seen. The white solid product was filtered and washed with hexane to remove thiophenol and air dried in a desiccator to give compound 43 (2.31 g, 90%).

(Z)-1,2-Bis(phenylthio) ethene (Control)

A solution of (Z)-1,2-dichloroethene (0.49 g, 5.04 mmol) and compound 43 (2.0 g, 15.15 mmol) in HMPA (10 mL) was stirred under nitrogen for 1 h. The solvent was removed under reduced pressure to give the crude product that was then purified by column chromatography using 100% hexane as a solvent to give control (1.04 g, 85%). $^1$H NMR (400 MHz, CDCl$_3$) δ 6.55 (s, 2H), 7.29 (m, 2H), 7.35 (t, J=7.7 Hz, 4H), 7.43 (s, 2H), 7.44 (m, 2H). HRMS ESI (m/z): Calculated for $C_{14}H_{12}S_2$ [M]$^+$: 244.0380. found: 244.0377.

Biphenyl-4-yl propiolate (1)

To an ice cooled and stirred solution of propargylic acid (285 mg, 4.01 mmol) and 4-phenylphenol (693 mg, 4.07 mmol) in dry diethyl ether was added dropwise a solution of N,N'-dicyclohexylcarbodiimide (DCC, 840 mg, 4.07 mmol) and 4-dimethylaminopyridine (DMAP, 3.2 mg, 0.03 mmol) in dry diethyl ether (10 mL) during 2 h under nitrogen atmosphere. Reaction mixture was then stirred at room temperature for 10 h, filtered and the solid was washed with diethyl ether. Then, the combined filtrate was washed with 1 N HCl solution followed by washing with brine and dried with anhydrous Na$_2$SO$_4$. The solvent was removed under reduced pressure to give the crude product that was then purified by column chromatography using ethyl acetate:hexane (1:9) as an eluant to give compound 1 (0.81 mg, 90%). $^1$H NMR (400 MHz, CDCl$_3$): δ 3.12 (s, 1H), 7.24 (s, 1H), 7.26 (s, 1H), 7.38 (s, 1H), 7.47 (t, J=7.8 Hz, 2H), 7.57 (s, 1H), 7.59 (s, 1H), 7.62 (s, 1H), 7.64 (s, 1H). HRMS ESI (m/z): Calculated for $C_{15}H_{10}O_2$ ([M+H]$^+$): 223.0681. found: 223.0734.

Biphenyl-4-yl 3-(diethylamino)acrylate (2)

Diethylamine (66 mg, 0.89 mmol) and compound 1 (200 mg, 0.89 mmol) were dissolved in dry THF (20 mL), and the solution was stirred at RT for 15 min. The solvent was removed under reduced pressure to give the crude product which was then purified by column chromatography using ethyl acetate:hexane (7:3) to give compound 2 (237 mg, 89%). $^1$H NMR (400 MHz, CDCl$_3$) δ 1.24 (t, J=7.0 Hz, 6H), 3.28 (br. s, 4H), 4.79 (d, J=13.0 Hz, 1H), 7.20 (d, J=8.6 Hz, 2H), 7.36 (t, J=7.4 Hz, 1H), 7.44 (t, J=7.8 Hz, 2H), 7.62 (m, 4H), 7.63 (d, J=13.0 Hz, 1H). HRMS ESI (m/z): Calculated for $C_{19}H_{21}NO_2$ ([M+H]$^+$): 296.1572. found: 296.1647.

Biphenyl-4-yl 3-(piperidin-1-yl)acrylate (3)

The compound 3 was prepared according to the method described for compound 2 employing piperidine (77 mg, 0.89 mmol) and compound 1 (200 mg, 0.89 mmol) to give white solid compound 3 (221 mg, 80%). $^1$H NMR (400 MHz, CDCl$_3$) δ 1.67 (br s, 6H), 3.30 (s (b), 4H), 4.83 (d, J=13.1 Hz, 1H), 7.19 (d, J=8.6 Hz, 2H), 7.34 (t, J=7.2 Hz, 1H), 7.44 (t, J=7.8 Hz, 2H), 7.59 (m, 5H). HRMS ESI (m/z): Calculated for $C_{20}H_{21}NO_2$ ([M−H]$^+$): 308.1572. found: 308.1646.

Biphenyl-4-yl 3-(phenylthio)acrylate (4)

To a stirred solution of 1,4-diazabicyclo[2.2.2]octane (DABCO, 10 mg, 0.89 mmol) and thiophenol (99 mg, 0.89 mmol) in dry THF (20 mL) at RT was added compound 1 (200 mg, 0.89) dissolved in dry THF (2 mL) through a syringe over 12 min. The reaction mixture was further stirred for 20 min. 10% NaOH$_{(aq)}$ was added. The combined organic layer was washed with brine, dried over anhydrous Na$_2$SO$_4$, filtered and the solvent was removed by evaporation. The crude product was purified by column chromatography using ethyl acetate:hexane (2:8) as an eluent to give compound 4 (254 mg, 85%). $^1$H NMR (400 MHz, CDCl$_3$) δ 5.84 (d, J=15.0 Hz, 1H), 7.18 (d, J=8.6 Hz, 2H), 7.46 (m, 6H), 7.58 (m, 6H), 8.05 (d, J=15.0 Hz, 1H). HRMS ESI (m/z): Calculated for C$_{21}$H$_{16}$O$_2$S ([M+H]$^+$): 333.0871. found: 333.0852.

Biphenyl-4-yl 3-(benzylthio)acrylate (5)

The compound 5 was prepared according to the method described for compound 4 employing compound 1 (200 mg, 0.89 mmol) and benzylthiol (112 mg, 0.89 mmol) to give white solid compound 5 (284 mg, 91%). $^1$H NMR (300 MHz, CDCl$_3$) δ 4.10 (s, 2H), 6.02 (d, J=15.1 Hz, 1H), 7.18 (d, J=8.3 Hz, 2H), 7.39 (m, 8H), 7.57 (t, J=5.9 Hz, 4H), 7.94 (d, J=15.1 Hz, 1H). HRMS ESI (m/z): Calculated for C$_{22}$H$_{18}$O$_2$S ([M+H]$^+$): 347.1028. found: 347.1101.

Biphenyl-4-yl 3-phenoxyacrylate (6)

The compound 6 was prepared according to the method described for compound 4 employing compound 1 (435 mg, 2.15 mmol) and phenol (223 mg, 2.36 mmol) to give white solid compound 6 (510 mg, 80%). $^1$H NMR (300 MHz, CDCl$_3$) δ 5.67 (d, J=12.2 Hz, 1H), 7.40 (d, J=8.9 Hz, 2H), 7.11 (d, J=8.5 Hz, 2H), 7.33 (q, J=7.9 Hz, 5H), 7.49 (t, J=7.0 Hz, 5H), 7.92 (d, J=12.2 Hz, 1H). HRMS ESI (m/z): Calculated for C$_{21}$H$_{16}$O$_3$ ([M+H]$^+$): 317.1099. found: 317.1175.

Biphenyl-4-yl 3-(benzyloxy)acrylate (7)

The compound 7 was prepared according to the method described for compound 4 employing compound 1 (300 mg, 1.34 mmol) and benzylalcohol (161 mg, 1.48 mmol) to give white solid compound 7 (419 mg, 94%). $^1$H NMR (400 MHz, CDCl$_3$) δ 5.00 (s, 2H), 5.53 (d, J=12.5 Hz, 1H), 7.18 (d, J=8.2 Hz, 2H), 7.39 (m, 8H), 7.57 (t, J=4.8 Hz, 4H), 7.88 (d, J=12.5 Hz, 1H). HRMS ESI (m/z): Calculated for C$_{22}$H$_{18}$O$_3$ ([M+H]$^+$): 331.1256. found: 331.133.

(E)-S-Phenyl 3-(piperidin-1-yl)prop-2-enethioate (8)

The compound 8 was prepared according to the method described for compound 3 employing piperidine (184 mg, 2.18 mmol) and compound 19 (350 mg, 2.18 mmol) to give pale red solid compound 8 (507 mg, 95%). $^1$H NMR (300 MHz, CD$_2$Cl$_2$) δ 1.64 (s, 6H), 3.27 (s, 4H), 5.11 (d, J=12.6 Hz, 1H), 7.38 (s, 3H), 7.45 (d, J=5.2 Hz, 1H), 7.48 (d, J=12.6 Hz, 1H). HRMS ESI (m/z): Calculated for C$_{14}$N$_{17}$NOS ([M+H]$^+$): 248.1031. found: 248.1125.

(E)-N-Phenyl-3-(piperidin-1-yl)acrylamide (9)

The compound 9 was prepared according to the method described for compound 3 employing piperidine (211 mg, 2.48 mmol) and compound 20 (360 mg, 2.48 mmol) to give brown solid compound 9 (497 mg, 87%). $^1$H NMR (300 MHz, CD$_2$Cl$_2$) δ 1.62 (s, 6H), 3.20 (s, 4H), 4.73 (d, J=12.6 Hz, 1H), 6.89 (s, 1H), 7.00 (t, J=6.2 Hz, 2H), 7.27 (t, J=6.9 Hz, 2H), 7.43 (d, J=12.6 Hz, 1H), 7.51 (d, J=6.9 Hz, 2H). HRMS ESI (m/z): Calculated for C$_{14}$H$_{18}$N$_2$O ([M+H]$^+$): 231.1419. found: 231.1512.

Phenyl 1-(3-(biphenyl-4-yloxy)-3-oxoprop-1-enyl) pyrrolidine-2-carboxylate (10)

The compound 10 was prepared according to the method described for compound 13 employing compound 23 (112 mg, 0.36 mmol), compound 1 (82 mg, 0.36 mmol) and 0.06 ml of N, N-diisopropylethylamine to give solid compound 10 (129 mg, 85%). $^1$H NMR (400 MHz, CDCl$_3$) δ 2.17 (m, 2H, pro), 2.38 (br. s, 2H, pro), 3.28-3.83 (m, 2H, pro) 4.49 (br. s, 1H, pro), 4.87 (d, J=12.0 Hz, 1H), 7.12 (d, J=7.8 Hz, 2H), 7.18 (d, J=8.5 Hz, 2H), 7.31 (m, 2H), 7.41 (q, J=7.5 Hz, 4H), 7.58 (s, 2H), 7.64 (s, 2H), 7.86 (d, J=12.0 Hz, 1H). HRMS ESI (m/z): Calculated for C$_{26}$H$_{23}$NO$_4$ ([M+H]$^+$): 414.1627. found: 414.1697.

Phenyl 1-(3-(biphenyl-4-yloxy)-3-oxoprop-1-enyl) pyrrolidine-3-carboxylate (11)

The compound 11 was prepared following all the steps described for compound 10 (137 mg, 90%). $^1$H NMR (400 MHz, CDCl$_3$) δ 1.51-1.71 (m, 1H, pro), 2.45 (br. s, 2H, pro), 3.40-3.95 (m, 4H, pro), 4.78 (d, J=13.0 Hz, 1H), 7.11 (d, J=7.7 Hz, 2H), 7.20 (d, J=8.6 Hz, 2H), 7.35 (s, 1H), 7.44 (q, J=7.6 Hz, 4H), 7.58 (s, 2H), 7.60 (s, 2H), 7.83 (d, J=13.0 Hz, 1H). HRMS ESI (m/z): Calculated for C$_{26}$H$_{23}$NO$_4$ ([M+H]$^+$): 414.1627. found: 414.1700.

(E)-Biphenyl-4-yl 3-(4-((2-phenoxyacetoxy)methyl) piperidin-1-yl)acrylate (12)

To a stirred solution of compound 36 (75 mg, 0.49 mmol) and compound 39 (250 mg, 0.74 mmol) in dry dichloromethane (DCM) was added drop wise a solution of DCC (407 mg, 1.98 mmol) and DMAP (60 mg, 0.49 mmol) in dry DCM (15 mL). Reaction mixture was then stirred at room temperature for 24 h. The solvent was removed under reduced pressure to give the crude product that was then purified by column chromatography using ethyl acetate: hexane (6:4) as an eluant to give a white solid compound 12 (279 mg, 80%). $^1$H NMR (300 MHz, CD$_2$Cl$_2$) δ 1.11 (m, 1H), 1.33 (m, 2H), 1.72 (t, J=12.9 Hz, 2H), 1.90 (d, J=9.9 Hz, 1H), 3.05 (br s, 1H), 3.58 (m, 2H), 4.09 (d, J=5.9 Hz, 2H), 4.68 (s, 2H), 4.83 (d, J=13.0 Hz, 1H), 6.91 (d, J=7.9 Hz, 2H), 7.02 (t, J=7.2, 1H), 7.15 (d, J=8.3 Hz, 2H), 7.33 (m, 2H), 7.45 (t, J=7.50, 2H), 7.59 (br s, 5H). HRMS ESI (m/z): Calculated for C$_{29}$H$_{29}$NO$_5$ ([M+H]$^+$): 472.2046. found: 472.2118.

Biphenyl-4-yl 3-(4-(3-phenoxypropyl)piperazin-1-yl)acrylate (13)

Compound 30 (150 mg, 0.45 mmol) was dissolved in dry THF (20 mL) with stirring under nitrogen. N,N-diisopropylethylamine (0.08 mL) was added drop wise and then compound 1 (100 mg, 0.45 mmol) dissolved in dry THF (5 mL) was added. The reaction mixture was stirred at RT for 15 min. After the reaction was completed, solvent was removed under reduced pressure to give the crude product which was then purified by column chromatography using ethyl acetate:hexane (4:6) to give product 13 (173 mg, 87%). $^1$H NMR (300 MHz, CD$_2$Cl$_2$) δ 1.94 (m, 2H), 2.51 (m, 6H), 3.31 (s, 4H), 4.01 (t, J=6.1 Hz, 2H), 4.80 (d, J=13.0 Hz, 1H), 6.89 (m, 3), 7.12 (d, J=8.2 Hz, 2H), 7.26 (t, J=7.7 Hz, 2H) 7.32 (d, J=6.2 Hz, 1H), 7.42 (t, J=7.5 Hz, 2H), 7.51 (s, 1H), 7.56 (m, 4H). HRMS ESI (m/z): Calculated for C$_{28}$H$_{30}$N$_2$O$_3$ ([M+H]$^+$): 443.2256. found: 443.2333.

(E)-Biphenyl-4-yl 3-(4-((2-phenoxy-10,15,20-triphenyl-21,23-dithiaporphyrin acetoxy)methyl)piperidin-1-yl)acrylate (14)

The compound 14 was prepared according to the method described for compound 12 employing compound 37 (80 mg, 0.11 mmol), compound 39 (56 mg, 0.17 mmol), DCC (45 mg, 0.22 mmol) and DMAP (13 mg, 0.11 mmol) to give a solid red purple compound 14 (128 mg, 74%). $^1$H NMR (300 MHz, CD$_2$Cl$_2$) δ 1.01 (m, 2H), 1.24 (m, 2H), 1.60 (m, 2H), 1.80 (d, J=12.2 Hz, 2H), 3.34 (m, 1H), 3.97 (br s, 1H), 4.14 (d, J=5.9, 2H), 4.72 (d, J=12.9 Hz, 1H), 4.88 (s, 2H), 6.97 (d, J=8.6 Hz, 2H), 7.32 (m, 3H), 7.45 (m, 5H), 7.74 (br s, 9H), 8.16 (m, 8H), 8.62 (m, 4H), 9.64 (m, 4H). HRMS ESI (m/z): Calculated for C$_{67}$H$_{51}$N$_3$O$_5$S$_2$ ([M+H]$^+$): 1042.3270. found: 1042.3343.

Biphenyl-4-yl 3-(4-(3-(5-(4-phenoxy-10,15,20-triphenyl-21,23-dithiaporphyrin propyl)piperazin-1-yl)acrylate (15)

The compound 15 was prepared following all the steps described for compound 13 (39 mg, 65%). $^1$H NMR (300 MHz, CDCl$_3$) δ 2.08 (br. s, 2H), 2.52 (br. s, 4H), 2.66 (br. s, 2H), 3.33 (br. s, 2H), 4.15 (br. s, 4H), 4.80 (d, J=13.3 Hz, 1H), 7.11 (d, J=8.4 Hz, 2H), 7.17 (s, 1H), 7.26 (m, 1H), 7.35 (t, J=7.6 Hz, 2H), 7.49 (s, 2H), 7.52 (s, 2H), 7.72 (s, 11H) 8.08 (d, J=8.6 Hz, 2H), 8.17 (s, 6H), 8.61 (s, 4H), 9.61 (s, 4H). HRMS ESI (m/z): Calculated for C$_{66}$H$_{52}$N$_4$O$_3$S$_2$ ([M+H]$^+$): 1013.35. found: 1013.3565.

(E)-((13S)-13-Methyl-17-oxo-7,8,9,11,12,13,14,15,16,17-decahydro-6H cyclopenta[a] phenanthren-3-yl)3-(4-((2-phenoxy-10,15,20-triphenyl-21,23-dithiaporphyrinacetoxy)methyl) piperidin-1-yl)acrylate (16). The compound 16 was prepared according to the method described for compound 12 employing compound 37 (120 mg, 0.17 mmol), compound 40 (108 mg, 0.25 mmol), DCC (68 mg, 0.33 mmol) and DMAP (20 mg, 0.17 mmol) to give a solid red purple compound 16 (211 mg, 75%). $^1$H NMR (300 MHz, CD$_2$Cl$_2$) δ 0.77 (s, 3H), 1.95-1.08 (m, 3H), 1.18-1.39 (m, 7H), 1.55-1.64 (m, 2H), 1.75-1.80 (m, 2H) 1.88-2.08 (m, 2H), 2.18-2.41 (m, 1H), 2.72 (m, 2H), 3.00 (br s, 1H), 3.33 (m, 1H), 3.53 (m, 2H), 3.96 (m, 1H), 4.13 (d, J=6.1 Hz, 2H), 4.69 (d, J=13.3 Hz, 1H), 4.87 (s, 2H), 6.62 (s, 2H), 7.07 (d, J=8.6, 1H), 7.29 (d, J=8.6 Hz, 2H), 7.43 (d, J=13.3 Hz, 1H), 7.74 (br s, 9H), 8.12 (d, J=8.6 Hz, 2H), 8.16 (m, 6H), 8.63 (m, 4H), 9.64 (m, 4H). HRMS ESI (m/z): Calculated for C$_{73}$H$_{63}$N$_3$O$_6$S$_2$ ([M+H]$^+$): 1142.4158. found: 1142.4233.

PS-L-Rh (17)

The compound 17 was prepared according to the method described for compound 12 employing compound 42 (100 mg, 0.12 mmol), Rhodamine B (58 mg, 0.12 mmol), DCC (99 mg, 0.48 mmol) and DMAP (13 mg, 0.01 mmol) to give a solid red purple compound 17 (101 mg, 65%). $^1$H NMR (300 MHz, CD$_2$Cl$_2$) δ 1.14 (m, 6H), 1.36 (m, 3H), 1.65 (m, 3H), 1.89 (m, 2H), 2.13 (s, 1H) 2.83 (s, 2H), 2.91 (s, 2H), 3.18 (s, 1H), 3.22 (s, 1H), 3.44 (m, 4H), 3.56 (m, 1H), 3.65 (s, 1H), 4.07 (s, 4H), 4.99 (d, J=13.0 Hz, 1H), 6.65 (s, 4H), 7.13 (d, J=9.1 Hz, 1H), 7.58 (d, J=8.1 Hz, 2H), 7.74 (d, J=13.0 Hz, 1H), 7.84 (s, 10H), 7.97 (s, 1H), 8.13 (d, J=6.6 Hz, 1H), 8.27 (m, 9H), 8.52 (d, J=8.2 Hz, 1H) 8.71 (s, 3H), 8.76 (s, 1H), 9.73 (s, 3H), 9.79 (s, 1H). HRMS ESI (m/z): Calculated for C$_{81}$H$_{70}$ClN$_5$O$_5$S$_2$ ([M+H]$^+$—Cl): 1256.998. found: 1256.4790.

S-Phenyl prop-2-ynethioate (19)

The compound 19 was prepared according to the method described for compound 1 employing thiophenol (1 g, 9.07 mmol), propargylic acid (0.64 g, 9.07 mmol), DCC (1.87 g, 9.07 mmol) and DMAP (7.3 mg, 0.06 mmol) to give brownish liquid compound 19 (1.24 g, 84%). $^1$H NMR (300 MHz, CD$_2$Cl$_2$) δ 3.40 (s, 1H), 7.46 (s, 5H).

N-Phenylpropiolamide (20)

The compound 20 was prepared according to the method described for compound 1 employing aniline (1 g, 0.01 mol), propargylic acid (0.76 g, 0.01 mol), DCC (2.2 g, 0.01) and DMAP (8.6 mg, 0.07 mmol) to give brown solid compound 20 (1.35 g, 87%). $^1$H NMR (300 MHz, CD$_2$Cl$_2$) δ 2.93 (s, 1H), 7.15 (t, J=6.9 Hz, 1H), 7.33 (t, J=7.5 Hz, 2H), 7.52 (t, J=7.4 Hz, 2H), 7.79 (br s, 1H).

1-(tert-Butoxycarbonyl)pyrrolidine-2-carboxylic acid (21)

(S)-Proline (2.3 g, 20 mmol) was dissolved in 40 mL of DCM. To the solution, triethylamine (3.73 mL, 26 mmol) and di-tert-butyl dicarbonate (6.3 g, 28.9 mmol) dissolved in DCM (5 mL) were added. The mixture was stirred at RT for 2.5 h. Then, the reaction was quenched with saturated aqueous citric acid solution (15 mL), washed with brine (30 mL) and water (20 mL). The organic layer was dried over anhydrous Na$_2$SO$_4$, filtered and the solvent removed by evaporation. The white crystallized solid formed was washed with hexane to obtain compound 21 (3.85 g, 90%). $^1$H NMR (400 MHz, CDCl$_3$) δ 1.42 (s, 2H), 1.75-2.39 (m, 4H), 3.22-3.54 (m, 2H), 4.21-4.39 (m, 1H).

1-tert-Butyl 2-phenyl pyrrolidine-1,2-dicarboxylate (22)

Compound 21 (500 mg, 2.32 mmol) and DCC (523 mg, 2.53 mmol) in DCM (12 mL) were stirred at 0° C. for 30 min under argon atmosphere. To the solution, phenol (199 mg, 2.12 mmol) was added and stirred at RT for 24 h. The reaction mixture was diluted with ethyl acetate (30 mL) and filtered. The combined organic layer was dried over anhydrous sodium sulfate, filtered and the solvent removed by evaporation. The crude product was purified by column chromatography using ethyl acetate-hexane (4:6) to give compound 22 as a white solid (492 mg, 80%). $^1$H NMR (400 MHz, CDCl$_3$) δ 1.46 (s, 9H), 1.89-2.43 (m, 4H), 3.40-3.66 (m, 2H), 4.41-4.55 (m, 1H), 7.09 (m, 2H), 7.22 (m, 1H), 7.37 (m, 2H).

Phenyl pyrrolidine-2-carboxylate (23)

Compound 22 (500 mg, 1.71 mmol) was dissolved in dry DCM (6 mL). Trifluoroacetic acid (0.66 mL, 8.58 mmol) was then added to the solution at 0° C. and stirred under nitrogen for 1 h. The reaction mixture was then concentrated under vacuum and used directly in the next step without further purification.

1-tert-Butyl 3-phenyl pyrrolidine-1,3-dicarboxylate (24)

The compound 24 was prepared according to the method described for compound 22 employing 1-(tert-butoxycarbonyl)pyrrolidine-3-carboxylic acid (500 mg, 2.32 mmol), phenol (198 mg, 2.12 mmol) and DCC (522 mg, 2.53) to give pale white solid compound 24 (510 mg, 83%). $^1$H NMR (400 MHz, CDCl$_3$) δ 1.40 (s, 9H), 1.84-1.57 (m, 1H), 2.21 (m, 2H), 3.17-3.70 (m, 4H), 7.00 (s, 1H), 7.02 (s, 1H), 7.17 (t, J=7.8 Hz, 1H), 7.32 (t, J=7.8 Hz, 2H).

Phenyl pyrrolidine-3-carboxylate (25)

The compound 25 was prepared according to the method described for compound 23 employing TFA (0.66 mL, 8.58 mmol) and compound 24 (500 mg, 1.71 mmol) to give white solid compound. The compound was used without further purification after solvent removal.

(3-Bromopropoxy)benzene (26)

Phenol (1.0 g, 10.6 mmol) was dissolved in acetone (20 mL). Anhydrous potassium carbonate (7.34 g, 53.1 mmol) and 1,3-dibromopropane (8.58 g, 42.5 mmol) was added to the solution. The reaction mixture was refluxed in an oil bath for 12 h. After the reaction, the potassium carbonate was removed by suction filtration and solvent was removed under reduced pressure to give the crude product which was then purified by column chromatography using ethyl acetate: hexane (3:7) to give product 26 (2.05 g, 90%). $^1$H NMR (400 MHz, CDCl$_3$) δ 2.24 (m, 2H), 3.54 (t, J=6.4 Hz, 2H), 4.03 (t, J=5.8 Hz, 2H), 6.86 (m, 3H), 7.21 (m, 2H).

5-(3-Bromopropoxy)phenyl-10,15,20-triphenyl-21,13-dithiaporphyrin (27)

Compound 27 was prepared according to the method described for compound 26 employing 5-(4-hydroxyphenyl)-10,15,20-triphenyl-21,23dithiaporphyrin (300 mg, 0.45 mmol), 1,3-dibromopropane (364 mg, 1.81 mmol) and potassium carbonate (311 mg, 2.26) to give pale red solid compound 27 (301 mg, 85%). $^1$H NMR (300 MHz, CDCl$_3$) δ 2.52 (m, 2H), 3.79 (t, J=6.3 Hz, 2H), 4.41 (t, J=5.6 Hz, 2H), 7.36 (d, J=8.3 Hz, 2H), 7.81 (s, 9H), 8.19 (d, J=8.3 Hz, 2H), 8.26 (d, J=3.6 Hz, 6H), 8.68 (s, 3H), 8.70 (s, 1H), 9.70 (s, 3H), 9.73 (s, 1H).

tert-Butyl 4-(3-phenoxypropyl)piperazine-1-carboxylate (28)

To a solution of n-Boc-piperazine (1.08 g, 5.80 mmol) in dry DMF (10 mL) were added anhydrous potassium carbonate (4.01 g, 29.04 mmol) and compound 26 (1.5 g, 6.97 mmol). The reaction mixture was stirred at RT for 8 h. The potassium carbonate was removed by suction filtration and the solvent was removed under reduced pressure. The residue was dissolved with water and extracted with ethyl acetate. The combined organic layers were dried over anhydrous sodium sulfate and the solvent was removed by evaporation. The crude product was purified by column chromatography using ethyl acetate:hexane (8:2) to give compound 28 (1.58 g, 85%). $^1$H NMR (400 MHz, CDCl$_3$) δ 1.39 (s, 9H), 1.92 (s, 2H), 2.36 (s, 4H), 2.48 (s, 2H), 3.39 (s, 4), 3.95 (m, 2), 6.83 (m, 2H), 7.19 (m, 3H).

tert-Butyl 4-(5-(3-phenyl-10,15,20-triphenyl-21,13-dithiaporphyrinoxypropyl) piperazine-1-carboxylate (29)

The compound 29 was prepared according to the method described for compound 28 employing compound 27 (150 mg, 0.19 mmol), n-Boc-piperazine (29 mg, 0.16 mmol) and potassium carbonate (110 mg, 0.80) to give pale red solid compound 29 (128 mg, 75%). $^1$H NMR (300 MHz, CDCl$_3$) δ 1.50 (s, 9H), 2.25 (br s, 2H), 2.60 (br s, 4H), 2.77 (br s, 2H), 3.59 (br s, 4H), 4.33 (br s, 2H), 7.33 (d, J=8.3 Hz, 2H), 7.80 (s, 9H), 8.16 (d, J=8.3 Hz, 2H), 8.24 (d, J=4.0, 6H), 8.68 (s, 4H), 9.68 (s, 4H).

1-(3-Phenoxypropyl)piperazine (30)

The compound 30 was prepared according to the method described for compound 23 employing TFA (6 mL) and compound 28 (550 mg, 1.72 mmol) to give white solid compound. The compound was used without further purification after solvent removal.

1-3(–(5-(4-Phenyl)-10,15,20-triphenyl-21,23dithiaporphyrin)oxypropylpiperazine (31)

Compound 29 (70 mg, 0.09 mmol) was dissolved in dry DCM (6 mL). After trifluoroacetic acid (0.03 mL) was added to the solution at 0° C., it was stirred under nitrogen for 1 h. The reaction mixture was then concentrated under vacuum and then used directly in the next step.

5-(4-Methoxyphenyl)-10,15,20-triphenyl-21-23-dithiaporphyrin(32)

Compound 32 was prepared following Meinhardt et al.[57] $_1$H NMR (400 MHz, CDCl$_3$) δ 4.11 (s, 3H), 7.36 (d, J=8.4 Hz, 2H), 7.81 (s, 9H), 8.12 (d, J=8.4 Hz, 2H), 8.16 (m, 6H), 8.63 (m, 4H), 9.64 (m, 4H). HRMS ESI (m/z): Calculated for C$_{45}$H$_{30}$N$_2$OS$_2$ ([M+H]$^+$): 679.1878. found: 679.186.

5-(4-Hydroxyphenyl)-10,15,20-triphenyl-21,23dithiaporphyrin (33)

Compound 33 was prepared following Meinhardt.[57] $^1$H NMR (400 MHz, CDCl$_3$) δ 7.11 (d, J=8.4 Hz, 2H), 7.63 (s, 9H), 8.10 (d, J=8.4 Hz, 2H), 8.16 (m, 6H), 8.63 (m, 4H), 9.64 (m, 4H). HRMS ESI (m/z): Calculated for C$_{44}$H$_{28}$N$_2$OS$_2$ ([M+H]$^+$): 665.1721. found: 665.1708.

Ethyl 2-phenoxyacetate (34)

The compound 34 was prepared according to the method described for compound 26 employing phenol (4.5 g, 0.05 mol), ethyl bromoacetate (31 g, 0.19 mol) and potassium carbonate (33 g, 0.24 mol) to give a colorless oily compound 34 (6.9 g, 81%). $^1$H NMR (300 MHz, CD$_2$Cl$_2$) δ 1.30 (t, J=7.0 Hz, 3H), 4.27 (q, J=7.0 Hz, 2H), 4.62 (s, 2H), 6.91 (d, J=7.9 Hz, 2H), 6.99 (t, J=7.0 Hz, 1H), 7.29 (t, J=7.6 Hz, 2H).

Ethyl 5,10,15-triphenyl-20-(4-carboxylatomethoxy)phenyl-21,23-dithiaporphyrin (35)

The compound 35 was prepared according to the method described for compound 26 employing compound 33 (0.25 g, 0.38 mol), ethyl bromoacetate (2.1 mL, 19 mmol) and potassium carbonate (2.6 g, 19 mmol) to give purple solid compound 35 (0.22 g, 78%). $^1$H NMR (300 MHz, CD$_2$Cl$_2$) δ 1.42 (t, J=7.0 Hz, 3H), 4.42 (q, J=7.0 Hz, 2H), 4.92 (s, 2H), 7.37 (d, J=8.2 Hz, 2H), 7.81 (br s, 9H), 8.19 (d, J=8.2 Hz, 2H), 8.26 (m, 6H), 8.69 (m, 4H), 9.70 (m, 4H). HRMS ESI (m/z): Calculated for C$_{48}$H$_{34}$N$_2$O$_3$S$_2$ ([M+H]$^+$): 751.2011. found: 751.2065.

2-Phenoxyacetic acid (36)

Compound 34 (2 g, 0.011 mol) was dissolved in 100 mL of THF, and 1 M NaOH (110 mL, 0.11 mol) was added. The reaction mixture was stirred at RT for 24 h. The solution was then acidified by the addition of 40 mL of acetic acid. The reaction mixture was diluted with 150 mL of H$_2$O and the product was extracted with ethyl acetate. The organic extracts were dried over magnesium sulfate and concentrated. The crude product was washed several times with hexane:ethylacetate (9:1) to give a pale white solid (1.58 g, 94%). $^1$H NMR (300 MHz, CD$_2$Cl$_2$) δ 4.69 (s, 2H), 6.92 (d, J=8.2 Hz, 2H), 7.03 (t, J=7.0 Hz, 1H), 7.32 (t, J=7.6 Hz, 2H).

5,10,15-Triphenyl-20-(4-carboxylatomethoxy)phenyl-21,23-dithiaporphyrin (37)

The compound 37 was prepared according to the method described for compound 36 employing compound 35 (0.18 g, 0.24 mmol), 1 M NaOH (20 mL, 20 mmol) and 8 mL of acetic acid to a purple solid compound 37 (0.16 g, 92%). $^1$H NMR (300 MHz, CD$_2$Cl$_2$) δ 5.00 (s, 2H), 7.42 (d, J=7.8, 2H), 7.80 (br s, 9H), 8.21 (br s, 8H), 8.67 (s, 4H), 9.70 (s, 4H).

(13S)-13-Methyl-17-oxo-7,8,9,11,12,13,14,15,16,17-decahydro-6H-cyclopenta[a]phenanthren-3-ylpropiolate (38)

The compound 38 was prepared according to the method described for compound 1 employing estrone (500 mg, 1.85 mmol), propargylic acid (262 mg, 3.69 mmol), DCC (763 mg, 3.69 mmol) and DMAP (2.98 mg, 0.03 mmol) and dry DMF (10 mL) to give white solid compound 38 (417 mg, 70%). $^1$H NMR (300 MHz, CD$_2$Cl$_2$) δ 0.84 (s, 3H), 1.52 (m, 5H), 1.85-2.51 (m, 8H), 2.84 (s, 2H), 2.99 (s, 1H), 6.81 (s, 1H), 6.84 (d, J=9.0 Hz, 1H), 7.24 (d, J=8.9 Hz, 1H). HRMS ESI (m/z): Calculated for C$_{21}$H$_{22}$O$_3$ ([M+H]$^+$): 323.1569. found: 323.1660.

(E)-Biphenyl-4-yl 3-(4-(hydroxymethyl)piperidin-1-yl)acrylate (39)

The compound 39 was prepared according to the method described for compound 2 employing piperidin-4-ylmethanol (900 mg, 4.05 mmol) and compound 1 (466 mg, 4.05 mmol) to give white solid compound 39 (1.15 g, 84%). $^1$H NMR (300 MHz, CD$_2$Cl$_2$) δ 1.29 (m, 1H), 1.80 (m, 2H), 3.08 (br s, 1H), 3.51 (s, 2H), 3.62 (d, J=9.9 Hz, 2H), 4.82 (d, J=13.0 Hz, 1H), 7.15 (d, J=8.2 Hz, 2H), 7.35 (m, 1H), 7.45 (t, J=7.0 Hz, 2H), 7.60 (br s, 5H). HRMS ESI (m/z): Calculated for C$_{21}$H$_{23}$NO$_3$ ([M+Na]$^+$): 338.1678. found: 338.1751.

(E)-((13S)-13-Methyl-17-oxo-7,8,9,11,12,13,14,15,16,17-decahydro-6H-cyclopenta[a]phenanthren-3-yl) 3-(4-(hydroxymethyl)piperidin-1-yl)acrylate (40). The compound 40 was prepared according to the method described for compound 2 employing piperidin-4-ylmethanol (61 mg, 0.53 mmol) and compound 38 (170 mg, 0.53 mmol) to give white solid compound 40 (212 mg, 92%). $^1$H NMR (300 MHz, CD$_2$Cl$_2$) δ 0.91 (s, 3H), 1.20-1.37 (m, 3H), 1.46 (s, 2H), 1.50 (s, 2H), 1.57-1.74 (m, 4H) 1.79 (s, 1H), 1.83 (s, 1H), 1.91 (d, J=11.4 Hz, 1H), 1.98-2.17 (m, 3H), 2.24-2.54 (m, 3H), 2.90 (m, 2H), 3.01 (s, 1H), 3.50 (s, 2H), 3.60 (d, J=11.1 Hz, 2H), 4.78 (d, J=12.9 Hz, 1H), 6.79 (s, 2H), 7.26 (d, J=8.1 Hz, 1H), 7.53 (d, J=12.9 Hz, 1H). HRMS ESI (m/z): Calculated for C$_{27}$H$_{35}$NO$_4$ ([M+Na]$^+$): 460.2566. found: 460.2452.

Compound 41.

The compound 41 was prepared according to the method described for compound 1 employing compound 33 (600 mg, 0.902 mmol), propargylic acid (320 mg, 4.51 mmol), DCC (930 mg, 0.4.51 mmol) and DMAP (11 mg, 0.09 mmol) and dry THF (10 mL) to give red purple solid compound 41 (400 mg, 70%). $^1$H NMR (400 MHz, CDCl$_3$) δ 3.1 (s, 1), 4.89 (d, J=12.8 Hz, 1H), 7.49 (d, J=8.4 Hz, 2H), 7.64 (d, J=12.8 Hz, 1H), 7.75 (m, 9H), 8.17 (m, 8H), 8.61 (m, 3H), 8.67 (d, J=4.5 Hz, 1H) 9.63 (m, 3H) 9.71 (d, J=4.5 Hz, 1H). HRMS ESI (m/z): Calculated for C$_{47}$H$_{28}$N$_2$O$_2$S$_2$ ([M+H]$^+$): 717.1592. found: 717.1591.

Compound 42.

The compound 42 was prepared according to the method described for compound 2 employing piperidin-4-ylmethanol (64 mg, 0.56 mmol) and compound 41 (400 mg, 0.56 mmol) to give red purple solid compound 42 (395 mg, 85%).$^1$H NMR (300 MHz, CD$_2$Cl$_2$) δ1.02 (m, 2H), 1.26 (m, 2H), 1.59 (m, 2H), 1.79 (m, 2H), 3.34 (m, 1H) 3.45 (m, 1H), 3.95 (s, 1), 4.89 (d, J=12.8 Hz, 1H), 7.49 (d, J=8.4 Hz, 2H), 7.64 (d, J=12.8 Hz, 1H), 7.75 (m, 9H), 8.17 (m, 8H), 8.61 (m, 3H), 8.67 (d, J=4.5 Hz, 1H) 9.63 (m, 3H) 9.71 (d, J=4.5 Hz, 1H). HRMS ESI (m/z): Calculated for C$_{53}$H$_{41}$N$_3$O$_3$S$_2$ ([M+H]$^+$): 832.2589. found: 832.2683.

General Photooxygenation Procedure.

In a NMR tube, an olefin (0.0048 mmol) was dissolved in CDCl$_3$ (0.5 mL). The photosensitizer compound (32), 3 mg, 0.0048 mmol] was added to this solution. Then, the reaction mixture was irradiated for 25 min using a diode laser (690 nm, 200 mW/cm$^2$). The reaction of olefins with singlet oxygen was monitored by the decrease of olefinic peaks in $^1$H-NMR spectra. In the case of compound 14, 15 and 16 no photosensitizer was added.

Procedure for monitoring the cleavage of the linker (PS-L-Rh) by fluorescence emission intensity affected by FRET.

Stock solutions of compound 17 (2 mM) were prepared in DMSO. 50 μl of stock solutions were then diluted with 950 μl either chloroform or Dulbecco's Modified Eagle Medium with 5% fetal bovine serum to give 100 μM solutions. The resulting solution was irradiated using a diode laser (690 nm, 200 mW/cm$^2$). 10 μl was taken every 10 min, and 990 μl of chloroform was added. The solutions were excited at 525 nm and the fluorescence measured from 550 nm to 750 nm.

Example 4

Visible Light Controlled Release of Anti-Cancer Drug Through Double Activation of ProDrug To improve therapeutic effects of drugs and to minimize side effects, prodrugs (PDs) can be designed to be activated by specific stimuli.[66-70] Light is a very attractive tool for activation of deactivated forms of drugs such as PDs and drugs entrapped in delivery vehicles,[71] and it acts as an external tool for more active control of spatio-temporal activation.[72,73] UV light has been used for spatio-temporal activation of PDs and caged compounds at a cellular level.[74,75] However, it was unable to be effectively applied to tissues due to limited tissue penetration, only up to 1 mm, and its toxicity.[71] While visible and near IR light can reach deeper tissue, about 1 cm,[72] its energy is too low to directly cleave protecting groups. To circumvent this problem, it was proposed to utilize a unique chemistry of singlet oxygen that can be generated by irradiation of visible and near IR light to photosensitizers (PSs) of PDs. Drugs are conjugated with singlet oxygen-labile olefinic linkers, after which the singlet oxygen cleaves the linkers via a spontaneous cleavage of a dioxetane formed by [2+2] cyclo-addition reaction of singlet oxygen with the olefins.[5,7,43] This mechanism had not been successfully demonstrated in the prior art for use in biological systems due to the limitations of available olefinic linkers and difficulties in their synthesis.

Figure 12:
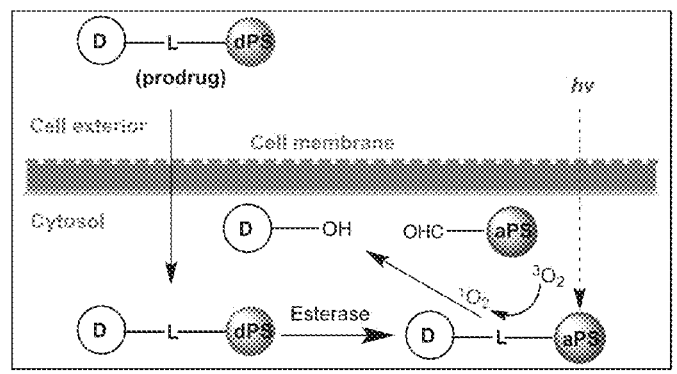
FIG. 12 schematically represents the mechanism involved in the prodrug double activation mechanism: hydrolysis and "photo-unclick chemistry". D, drug; L, linker; dPS, deactivated photosensitizer; aPS, activatable photo-sensitizer; hv, light.

Example 3 reported a photo-cleavable aminoacrylate linker that could be synthesized via click chemistry and then cleaved by singlet oxygen. Because singlet oxygen can be generated by the combination of visible/near IR light (400-800 nm) and a corresponding PS, aminoacrylate linkers can be cleaved by such low energy light via a singlet oxygen. In fact, the cleavage of aminoacrylate linkers by the combination of 690 nm and dithiaporphyrin PS was verified in Example 3. Based on the photo-unclick chemistry, it was successfully demonstrated that visible light-triggered PDs of anticancer compounds. A double activatable PD system was prepared to prove the concept of dPS which could be further engineered to improve specificity of activation.[76-78] A cellular esterase, by which only intracellular dPS was activated, was used as a model activation stimulus in vitro. Thus, the dPS of the PD was activated first by intracellular esterase and then the drug was released upon irradiation (FIG. 12). It was expected that dPS would make the conjugates less vulnerable to unwanted degradation under normal room light condition, which was a tedious problem the conjugates with non-dPSs.

To test the double activatable PD concept, two PDs 10 and 11 were prepared from two cytotoxic compounds (SN-38 and CA-4) as shown in Scheme 7. SN-38 is an active metabolite of irinotecan (CPT-11, topoisomerase I inhibitor) and it is at least 1000 times more active than irinotecan.[79] CA-4 is the active component of combretastatin A-4 phosphate, an antiangiogenic and anti-mitotic agent.[80] However, due to the highly toxic nature of these drugs (CA-4 and SN-38), detailed studies for the first activation (hydrolysis of dPS by esterase) and the second activation (release of free drug by irradiation) were hampered by cell death at the experimental concentration (10 µM). Thus, the prodrug 9 (see Scheme 7) from non-toxic coumarin was prepared for the quantitative studies of the two activation steps, avoiding the interference by the released drug (coumarin). The esterase-activatable PS 2 was prepared in two steps from 5(6)-carboxyfluorescein: tetra-iodination followed by di-acetylation (Scheme 6). Respectively, the hydroxyl group of drugs was esterified by Steglich esterification[81] with prolionic acid in presence of DCC and DMAP to yield 3-5 (Scheme 7). The intermediates 6-8 were then synthesized via a click (yne-amine) reaction with stirring compounds 3-5 and 4-piperidinemethanol. Finally, the esterification between hydroxyl group of intermediates 6-8 and the carboxyl group of 2 gave PDs 9-11 (Scheme 7). The PDs were prepared in three steps under mild conditions with high yields [Scheme 7 and Supporting Information herein below]. The purity of PDs 9-11 was verified above 95% by HPLC.

Scheme 6. Preparation of dPS (2)[a]

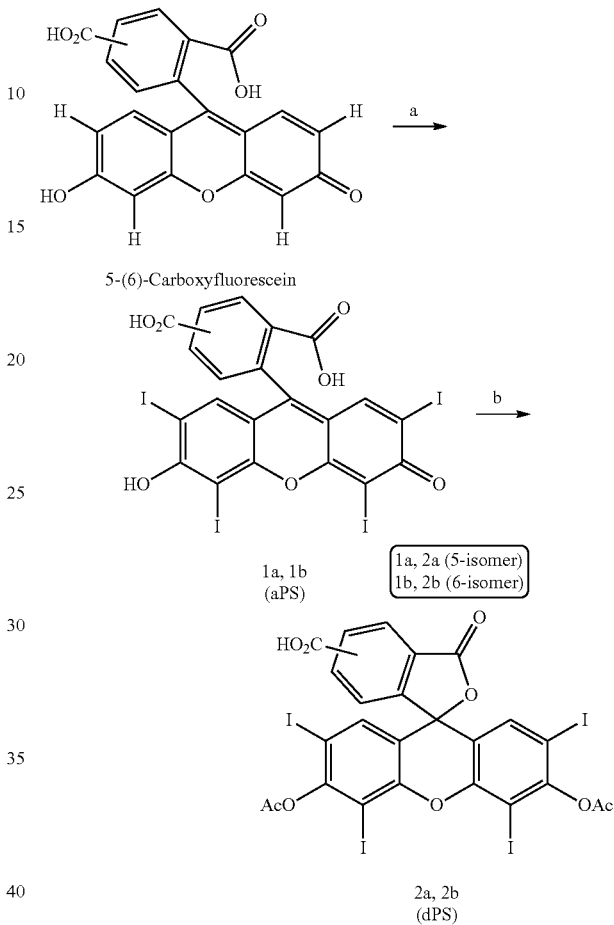

[a]Reagents: (a) Iodine, NaI, NaHCO₃; (b) Dry pyridine, anhydrous acetic anhydride.

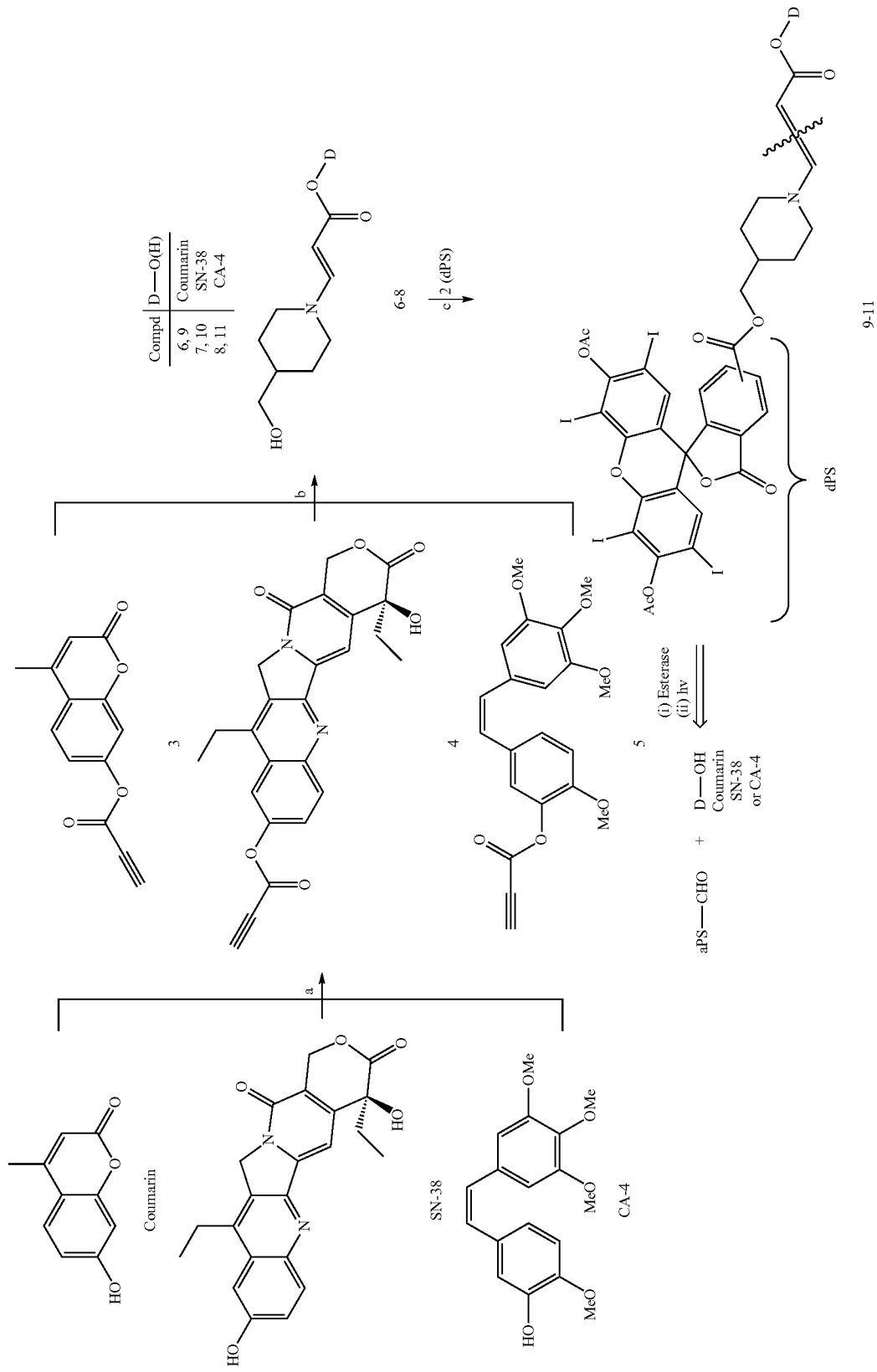
Scheme 7. Preparation of PDs (9-11)[a] and schematic representation of aminoacrylate linker cleavage.
[a]Reagents: (a) Propionic acid, DCC, DMAP; dry CH₂Cl₂/dry DMF (b) 4-Piperidinemethanol, THF; (c) 2, DCC, dry CH₂Cl₂.

Figure 13:
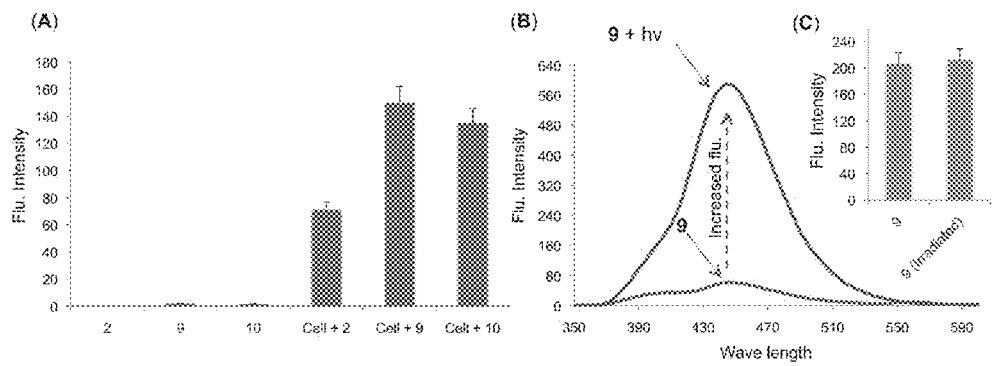
FIG. 13 represents various fluorescence emissions. Panel A of FIG. 13 graphically depicts fluorescence emission (570 nm) of 2, 9, and 10 from Schemes 6 and 7 (ext. 520 nm): Samples in DMSO (left three bars) and in cell lysate in DMSO (right three bars). Panel B of FIG. 13 graphically depicts increased coumarin fluorescence intensity of 9 from blue (before irradiated) to red spectrum (after irradiated at 320 nm). Panel C of FIG. 13 graphically depicts fluoresence emission (440 nm, ext. 320 nm) of 9 with or without irradiation in cell-free medium.
Figure 14:
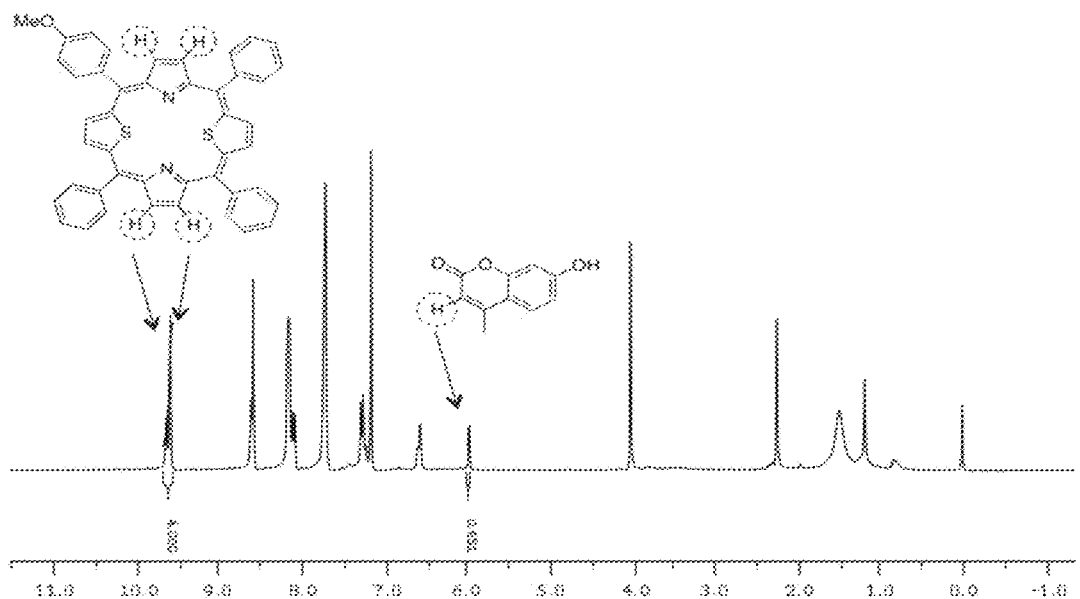
FIG. 14 graphically depicts the $^1$H-NMR spectrum (300 MHz) of the mixture of coumarin (0.85 mg) and CMP-OMe (3 mg) in CDCl$_3$ (0.5 mL) before the irradiation.

Both fluorescence spectroscopy and HPLC indicated the effective activation of dPS by cellular esterase. Since dPS 2 (see Scheme 6) has no fluorescence and the activatable PS (aPS) 1 (see Scheme 6) has a fluorescence quantum yield of 0.25 (Table 6), activation of dPS should result in large fluorescence emission. MCF-7 cells were incubated in presence of 10 µM of compound (2, 9, or 10 from Schemes 6 and 7) in 200 µL complete medium (DMEM+10% FBS+1% antibiotics) per well in a 96-well microplate. After 24 h incubation, the medium was removed and the cells were lysed with 100 µL DMSO. Then, fluorescence emission of the cell lysate was recorded (Panel A of FIG. 13). Larger emissions were detected from the cell lysates compared to the sample solutions in DMSO (10 µM), presumably, due to the activation of dPS in cells. However, dPS was not activated solely by the complete medium. When these compounds were added to the cell-free complete medium and incubated for 24 h, no significant increase in fluorescence intensity was observed. To quantify the activation of dPS of 9, 9 and the acetyl-hydrolyzed product of 9 were determined by HPLC, detected at 11 and 7 min, respectively (mobile phase: 100% acetonitrile and a flow-rate of 0.3 mL/min). Based on the standard curve of 9, it was estimated that 36% of 9 was recovered from incubated MCF-7 cells with 10 µM of 9. Accordingly, about 64% of 9 seemed to be activated.

TABLE 6

Photophysical Properties of Selected Compounds

| Compound | $\lambda_{max}^a$ (nm) | Extinction Coefficient ($M^{-1}cm^{-1}$) | $e_{max}^b$ (nm) | $FQY^c$ ($\phi$) |
|---|---|---|---|---|
| 5-(6) carboxy-fluorescein | 462 | $8.00 \times 10^4$ | 525 | 0.90 |
| 1 | 556 | $8.98 \times 10^4$ | 572 | 0.25 |
| 2 | 315 | $0.90 \times 10^4$ | — | ~0 |
| 7-hydroxy-4-methyl-coumarin | 325 | $1.58 \times 10^4$ | 378 | 0.14 |
| 9 | 323 | $2.36 \times 10^4$ | 377 | $0.03 \times 10^{-2}$ |

Experiments carried out in DMSO solution,
[a] absorption maximum,
[b] emission maximum, and
[c] fluorescence quantum yield.

Figure 15:
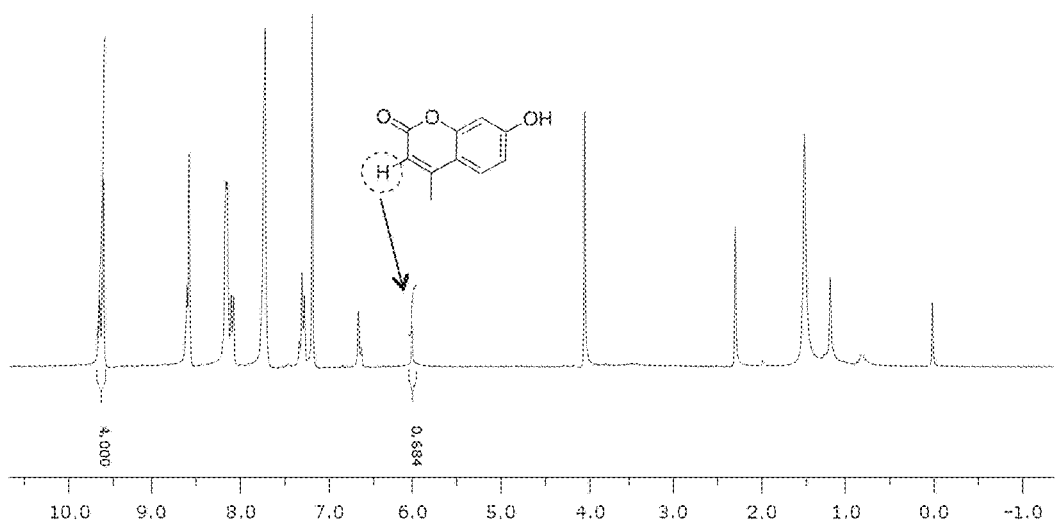
FIG. 15 graphically depicts the $^1$H-NMR spectrum (300 MHz) of the mixture of coumarin (0.9 mg) and CMP-OMe (3.0 mg) in CDCl$_3$ (0.5 mL) after the irradiation.
Figure 16:
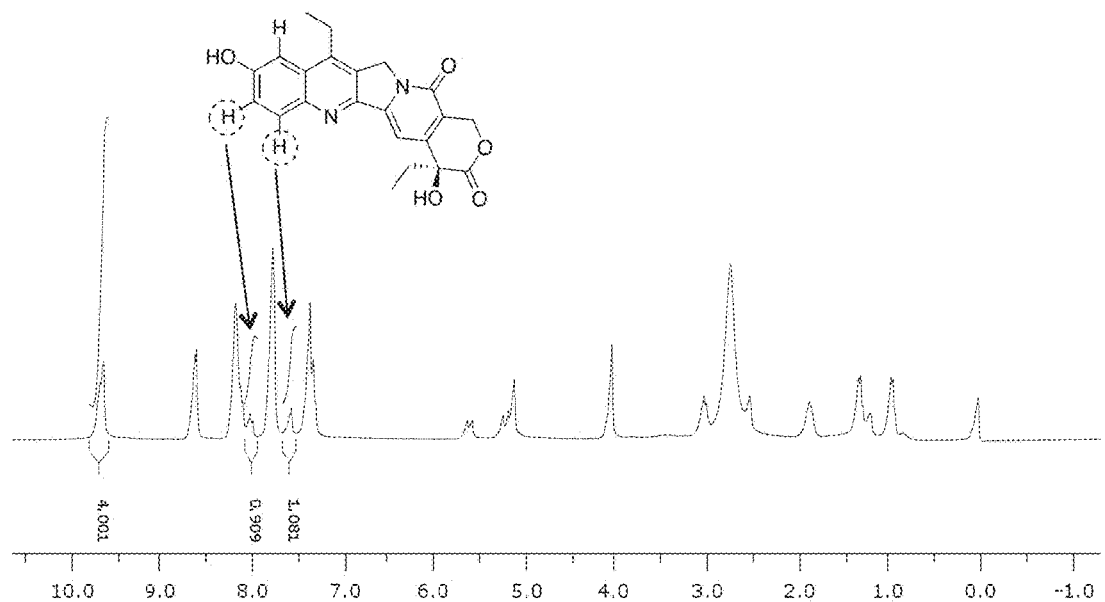
FIG. 16 graphically depicts the $^1$H-NMR spectrum (300 MHz) of the mixture of SN-38 (1.9 mg) and CMP-OMe (3.0 mg) in 0.5 mL of CDCl$_3$+DMSO-d$_6$ before the irradiation.
Figure 17:
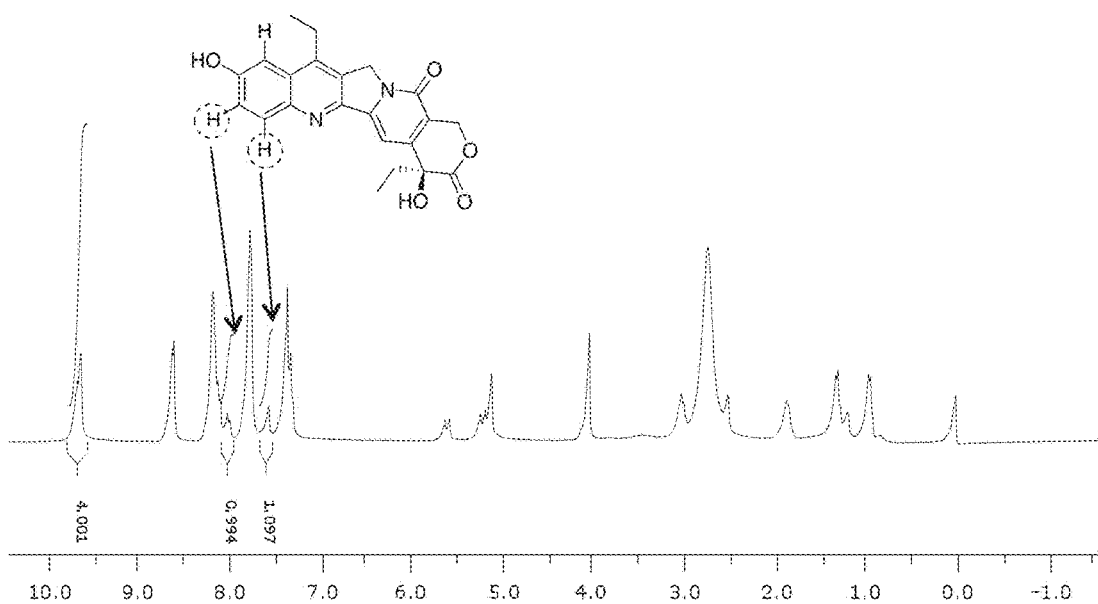
FIG. 17 graphically depicts the $^1$H-NMR spectrum (300 MHz) of the mixture of SN-38 (1.9 mg) and CMP-OMe (3.0 mg) in 0.5 mL of CDCl$_3$+DMSO-d$_6$ after the irradiation.
Figure 18:
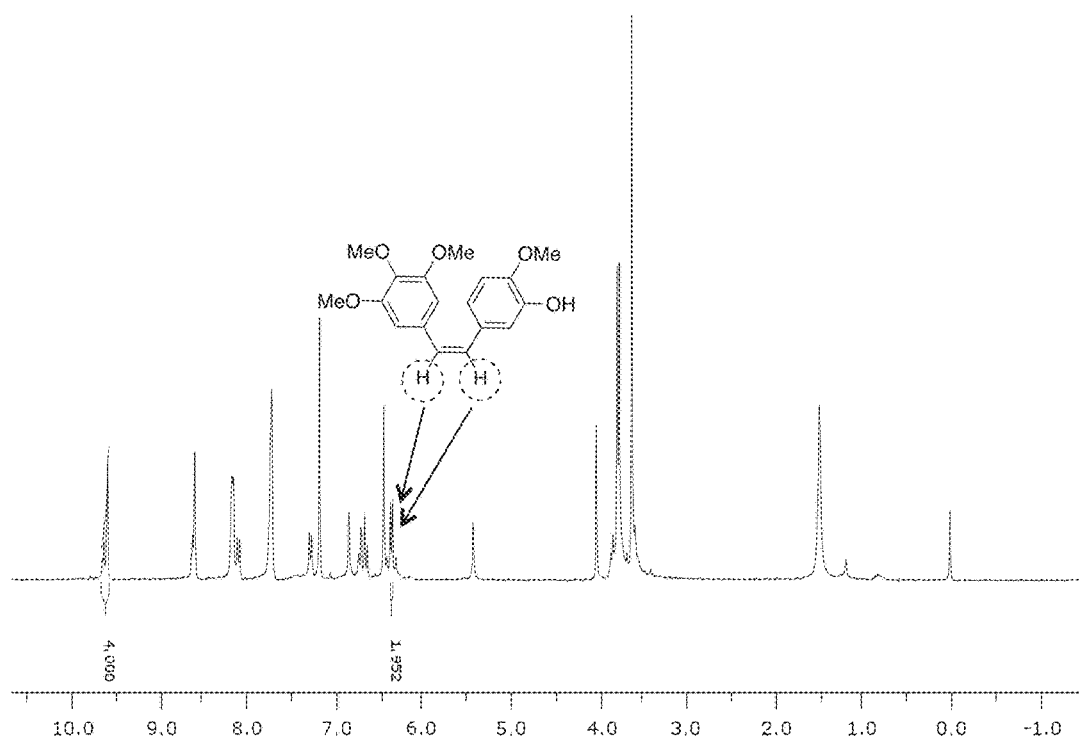
FIG. 18 graphically depicts the $^1$H-NMR spectrum (300 MHz) of the mixture of CA-4 (1.5 mg) and CMP-OMe (3.0 mg) in CDCl$_3$ (0.5 mL) before the irradiation.
Figure 19:
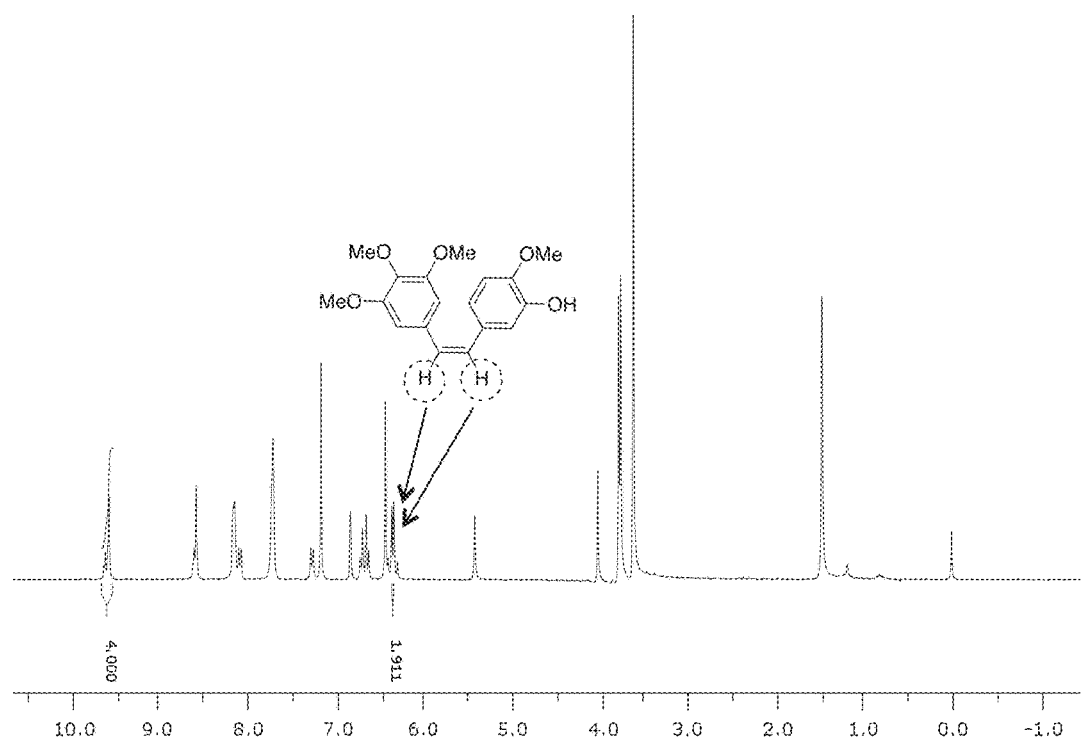
FIG. 19 graphically depicts the $^1$H-NMR spectrum (300 MHz) of the mixture of CA-4 (1.5 mg) and CMP-OMe (3.0 mg) in CDCl$_3$ (0.5 mL) after the irradiation.
Figure 20:
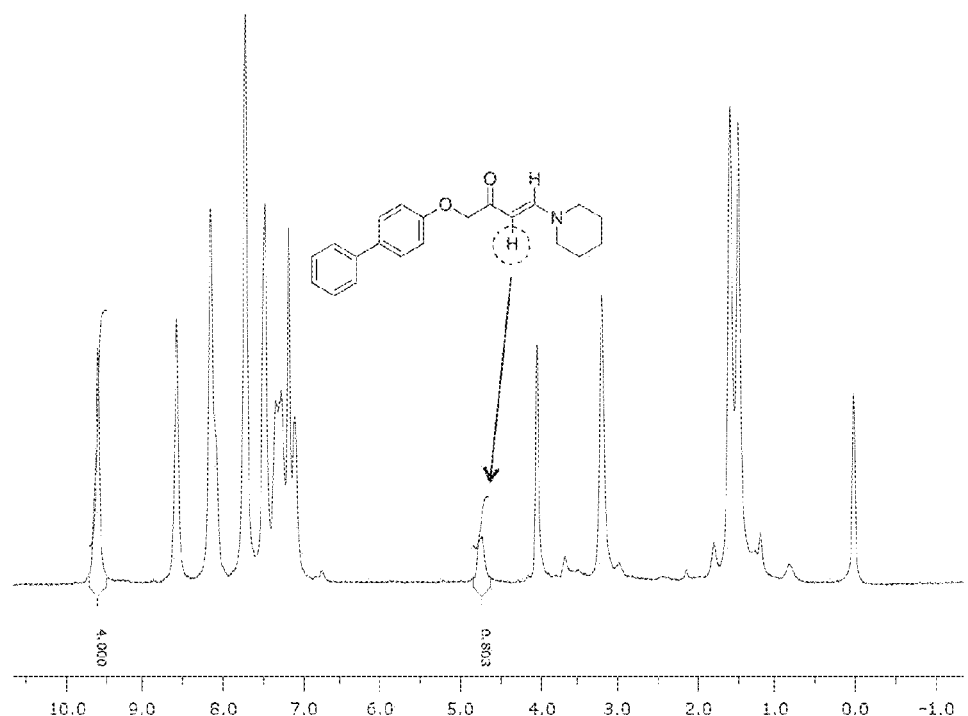
FIG. 20 graphically depicts the $^1$H-NMR spectrum (300 MHz) of the mixture of the model compound [(E)-N-phenyl-3-(piperidin-1-yl)acrylamide, 1.4 mg] and CMP-OMe (3.0 mg) in CDCl$_3$ (0.5 mL) before the irradiation.
Figure 21:
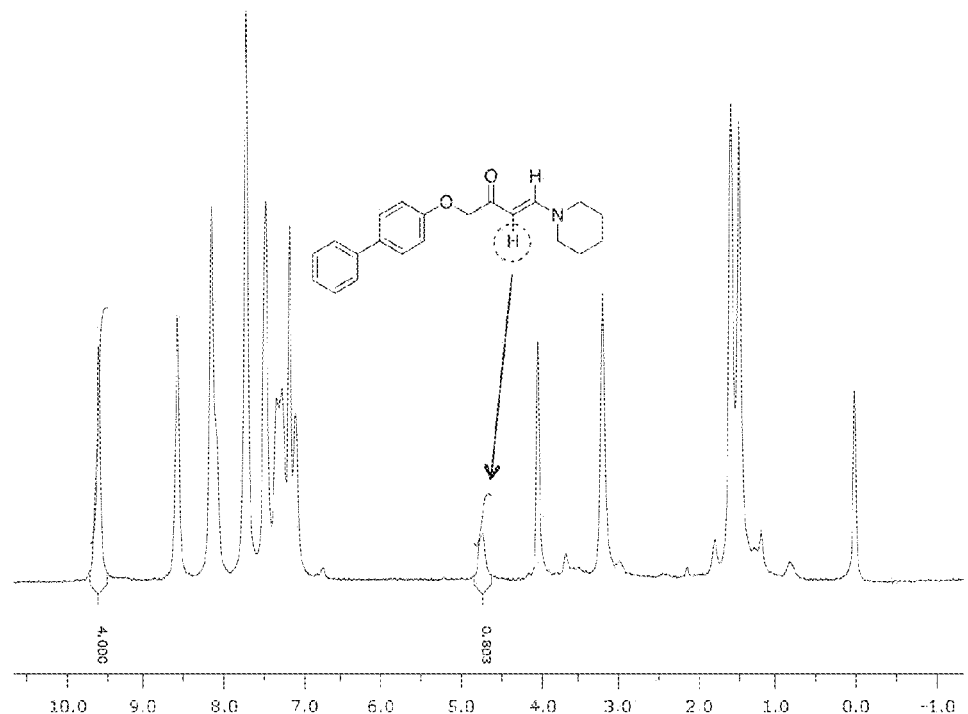
FIG. 21 graphically depicts the $^1$H-NMR spectrum (300 MHz) of the mixture of the model compound [(E)-N-phenyl-3-(piperidin-1-yl)acrylamide, 1.4 mg] and CMP-OMe (3.0 mg) in CDCl$_3$ (0.5 mL) after the irradiation.

The cleavage of aminoacrylate linkers after irradiation was supported by the increased coumarin fluorescence of 9 by irradiation (FIGS. 14-21). The unique peak of each compound was integrated against the peak of CMP-OMe (four protons of CMP-OMe at 9.7 ppm, FIG. 14), which was known to be inert to singlet oxygen oxidation. Interestingly, we did not see any change in the $^1$H-NMR data of three drugs after the irradiation (FIGS. 15, 17, and 19). However, we observed 77% decrease of the proton peak of the aminoacrylate linker after the irradiation (FIG. 21). Based on this data, it was concluded that the aminoacrylate linker reacted with singlet oxygen much faster than all the other compounds (coumarin, CA-4, and SN-38) and that these compounds were not oxidized at all under this oxidation condition. PD 9 had negligible coumarin emission compared to that of free coumarin at the equimolar concentration. In the presence of 10 µM of 9, MCF-7 cells were incubated for 24 h to activate dPS. Then, the samples were irradiated by visible light (540±10 nm, 8 mW/cm², 30 min). The irradiated sample showed 10× increased coumarin fluorescence emission compared to the sample before irradiation, presumably due to the release of coumarin (Panel B of FIG. 13). In contrast, when 9 was irradiated in the cell-free medium, it did not show any significant increase of the fluorescence (Panel C of FIG. 13). The released free coumarin was also detected and quantified by HPLC based on the standard curve of free coumarin. As such, almost 99% of 9 released coumarin while only 64% of dPS of 9 were activated when irradiated. These results suggest that the singlet oxygen in aPS of 9 cleaved not only the linker of itself but also linkers in other PD molecules. These results further indicate that the activation of dPS by intracellular esterase and the release of coumarin from 9 upon irradiation with light.

The rapid reaction of aminoacrylate linker with singlet oxygen was further demonstrated by a comprehensive photooxygenation kinetics study and experimental analysis, which is summarized as follows.

Fluorescence emission was used to monitor the disappearance of 1,3-diphenylisobenzofuran (DPBF) which was recorded on a LS 50 B luminescence spectrometer (Perkin Elmer, USA). DPBF ($5 \times 10^{-2}$ M) and Rose Bengal ($0.5 \times 10^{-5}$ M) stock solution in dry acetone was prepared. In addition, varying known concentrations of 2,3-dimethylbutene, (E)-N-phenyl-3-(piperidin-1-yl)acrylamide (a model compound with aminoacrylate linker) and Combretastatin A-4 (CA-4) were freshly prepared. Using a tungsten-halogen light source filtered at 540±10 nm (Lumacare), the appropriate solution of DPBF-Rose Bengal with or without a substrate placed in a fluorescence cuvette and held in a thermostated cell at 15° C. with stirring was irradiated with 0.1 mW/cm² light intensity at 30 sec interval. The fluorescence intensity of DPBF at 455 nm as a function of time provided the rate of photooxygenation of DPBF. The singlet oxygen could be consumed by two substrates (A and F) and a solvent in the solution of two substracts. As such, the reaction kinetics could be determined in light of the following analysis.

The steady-state approximation for singlet oxygen resulted in equation 1.

$$\frac{-d[F]}{dt} = K \frac{k_f[F]}{k_f[F] + (k_r + k_q)[A] + k_d} \quad (1)$$

Because [F]<<[A], equation 2 is:

$$\frac{-d[F]}{dt} = K \frac{k_f[K]}{(k_r + k_q)[A] + k_d} \quad (2)$$

Integrating equation 2, yields equation 3:

$$\ln([F_0]/[F_t]) = K \frac{k_f[F]}{(k_r + k_q)[A] + k_d} t \quad (3)$$

In the absence of an acceptor, equation 3 becomes:

$$\ln([F_0]/[F_t]) = K \frac{k_f}{k_d} t \quad (4)$$

Based on the typical Stern-Volmer analysis, division of the slopes of the first order plots of equation (4) by equation (3) affords equation (5), wherein $S_o$ is the slope of equation (4) and $S_x$ is the slope of equation (3):

$$(1)\frac{S_o}{S_x} = 1 + \frac{(k_r + k_q)[A]}{k_d} \quad (5)$$

Figure 22:
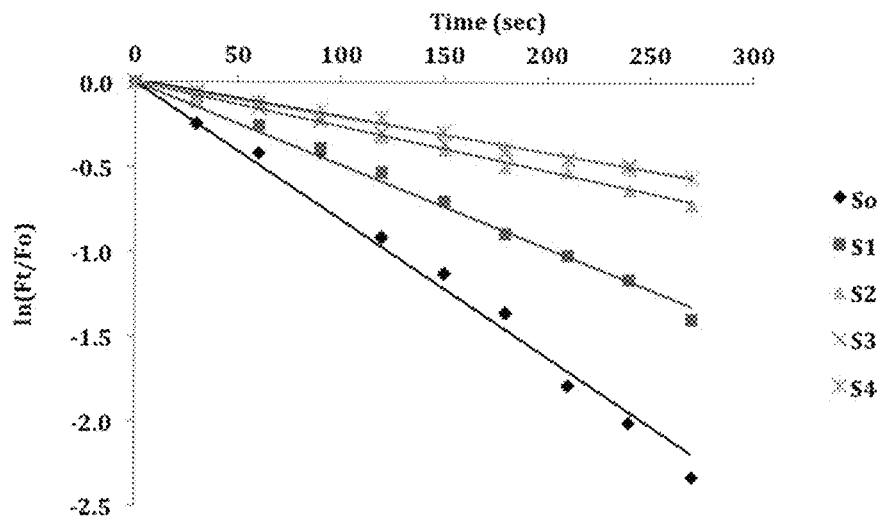
FIG. 22 depicts plots for the determination of the $S_0$ and $S_x$ values of 2,3-dimethyl-2-butene.
Figure 23:
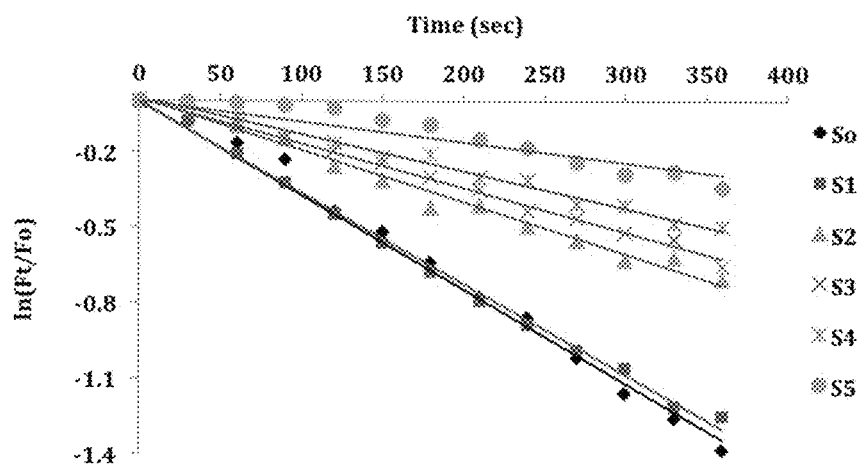
FIG. 23 depicts plots for the determination of the $S_0$ and $S_x$ value of aminoacrylate linker, (E)-N-phenyl-3-(piperidin-1-yl)acrylamide.
Figure 24:
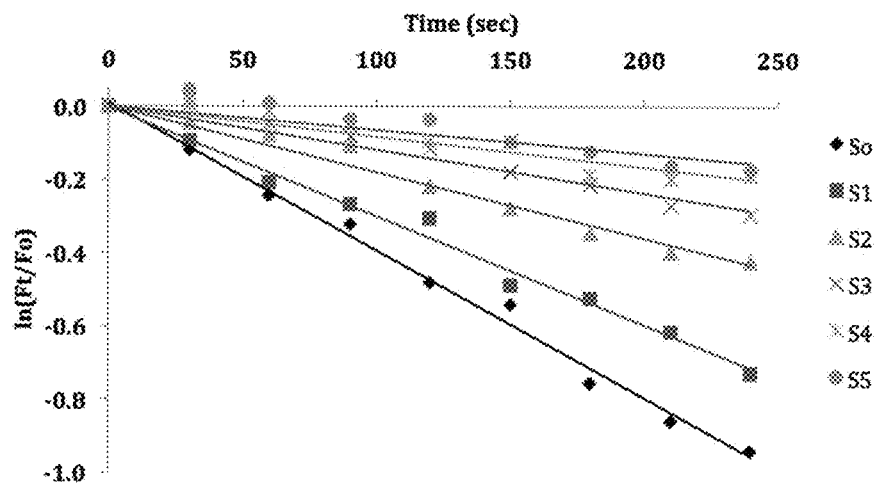
FIG. 24 depicts plots for the determination of the $S_0$ and $S_x$ values of combretastatin A-4.

Using the above kinetic analysis and equation (5), the second order rate constant (k) of the aminoacrylate linker was experimentally determined to be $2.5 \times 10^7$ $M^{-1}s^{-1}$, wherein $k = k_r + k_q$ The second order rate constants (k) were determined experimentally by first determining, $S_0$ and $S_x$, which were obtained from the plots of $\ln([F_t]/[F_0])$ vs. Time as shown in FIGS. 22, 23, 24, where the slope of the plot is –S. [F] was determined by the fluorescence of F (DPBF). Then, β value was calculated from the plot of $S_0/S_x$ vs. [A]. The slope is $1/\beta = (k_r+k_q)/k_d$ (β value is $k_d/(k_r+k_q)$ and an index of reactivity of A with singlet oxygen). From the kd value of the solvent (kd of acetone=38,400 $s^{-1}$), β value of A was calculated. The second order rate constant (k) of A was calculated from β value, where k is the sum of the rate constants of chemical reaction and singlet oxygen quenching: $k=k_r+k_q$.

The oxidation by singlet oxygen, not by superoxide radical, was also suggested by kinetic study with specific ROS quenchers. To determine the effect of specific ROS quenchers on the oxidation of the aminoacrylate linker, the rate of oxidation of aminoacrylate linker was determined by $^1$H-NMR using the vinyl proton of the aminoacrylate linker (FIG. 20). A solution of (E)-N-phenyl-3-(piperidin-1-yl) acrylamide (9 mM), a photosensitizer (CMP-OMe, 9 mM), a ROS quencher (0 or 9 mM) was in a $CDCl_3$ solvent in a NMR tube was exposed to the irradiation (690 nm diode laser, 100 mW/cm$^2$) and $^1$H-NMR was taken every 5 min. The ROS quencher was either a singlet oxygen quencher (DABCO or β-Carotene) or a superoxide quencher (1,4-Benzoquinone) and the photosensitizer was CMP-OMe (5-(4-methoxyphenyl)-10,15,20-triphenyl-21,23-dithiaporphyrin).

Figure 25:
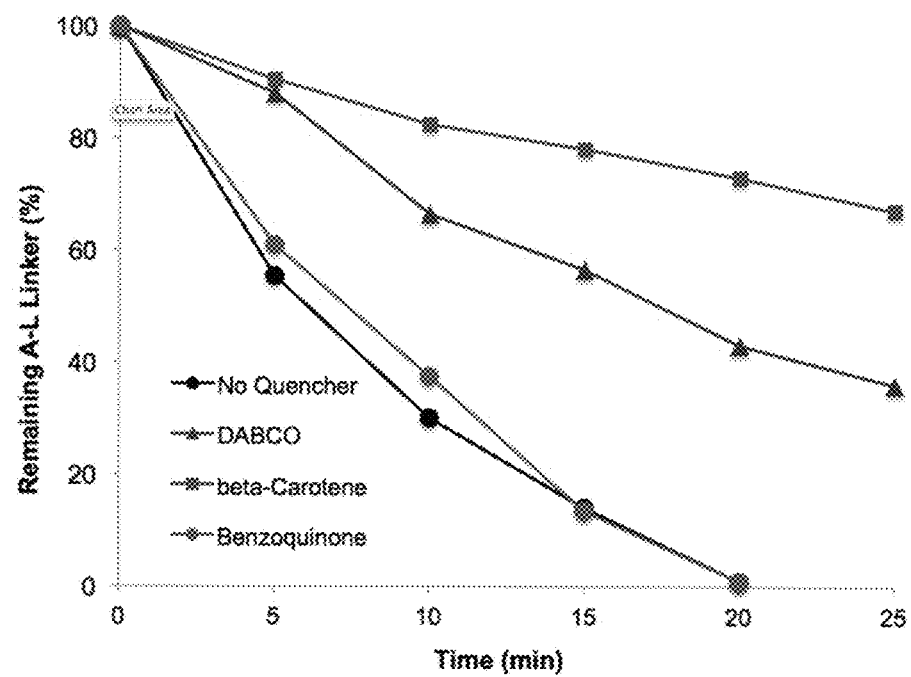
FIG. 25 depicts the kinetics of cleavage of A-L linker of the model compound ([(E)-N-phenyl-3-(piperidin-1-yl)acrylamide]) with or without a ROS quencher (DABCO, β-carotene, or 1,4-benzoquinone). Data points were an average of two independent trials.

The singlet oxygen quenchers (DABCO and β-carotene) effectively delayed the oxidation of the aminoacrylate linker but the superoxide radical quencher (1,4-benzoquinone) did not make any delay of the oxidation of the linker (FIG. 25). The more effective singlet oxygen quencher (β-carotene, $k=1.2\times10^{10}$ $M^{-1}s^{-1}$) had a larger delay than the less effective quencher (DABCO, $k=2.6\times10^8$ $M^{-1}s^{-1}$).[88]

The biological activity of PDs with or without irradiation was also evaluated to prove the concept of the double activatable PDs (Table 6). The addition of the bulky group the dPS-linker effectively reduced the dark toxicity of CA-4 and SN-38. PDs 10 and 11 were 4.8 and 14.5 times less toxic than parent drugs (SN-38 and CA-4) without irradiation. On the other hand, the irradiation restored the potent activity of SN-38 and CA-4 from the PDs. The $IC_{50}$ values of photo-toxicity of 10 and 11 were very close to those of dark-toxicity of CA-4 and SN-38. It was consistent with the above cleavage result of 9 where nearly 100% of 9 released the coumrain after irradiation. Therefore, it was estimated that [D-L-dPS] initial=[drug] after irradiation and thus, $IC_{50}$ of drug without irradiation≈$IC_{50}$ of PD with irradiation. The double activatable PDs performed very well.

TABLE 6

Toxicities of drugs SN-38, CA-4 (in dark) and the PDs 10, 11 (dark- and photo-toxicity)

| Compounds | Dark-toxicity, $IC_{50}$, nM (MCF-7) | Photo-toxicity, $IC_{50}$, nM (MCF-7) |
|---|---|---|
| SN-38 | 170 | nt |
| CA-4 | 8 | nt |
| 10 | 820 | 218 |
| 11 | 116 | 13 | nt, not tested;
$IC_{50}$, 50% inhibitory concentration

Figure 26:
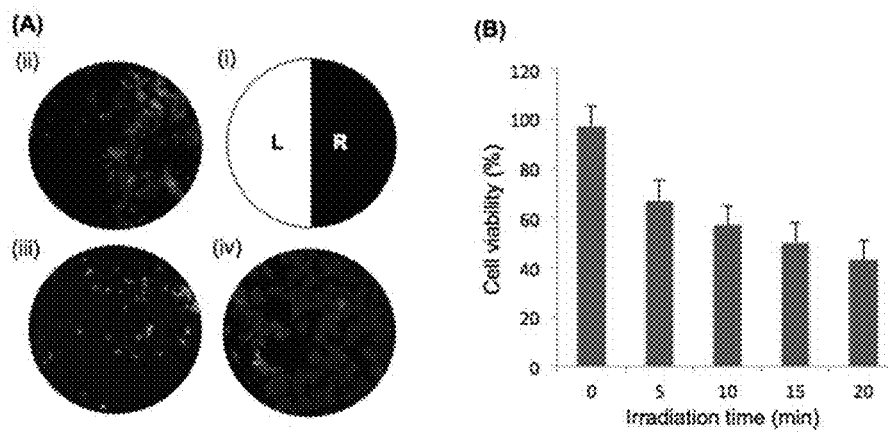
FIG. 26 contains fluorescence-microscopy images of live cells and light-dose dependent cell damage.

It was also determined that released drugs, not photodynamic effect (i.e., direct cell damage by singlet oxygen), were primarily responsible for the photo-toxicity of the PDs. Since singlet oxygen can also kill cells and the dPS of the PD are activated inside cells, a question remained as to whether the photo-toxicity of PDs came from the released drugs or from singlet oxygen. To examine it, the cells were treated with PD 11 in 96-well microplate but irradiated only half of each well for 30 min. The other half was protected from light using black tape. Fluorescence images of the live cells covering both half were taken after another 96 h of incubation (FIG. 26A). Since singlet oxygen has limited diffusion distance (~10-300 nm),[82-84] the singlet oxygen generated in the irradiated half of the wells could not damage cells in the un-irradiated half. However, the released drugs were stable and thus could damage entire wells by diffusion. Indeed, in wells treated with PS 2, the un-irradiated half looked healthy at the similar density to the control wells (FIG. 26A-ii). In stark contrast, the wells, treated with 11 (25 nM), showed only a few live cells in the un-irradiated half at a similar density to the irradiated area (FIG. 26A-iii). In addition, the control of 11 (25 nM) was monitored without irradiation (FIG. 26A-iv). The data clearly demonstrated that the released drugs, not singlet oxygen, killed the cells in the un-irradiated area. On the other hand, the irradiated cells seemed to be more damaged by PDT effects. The live cell density of the irradiated side was less than the un-irradiated area treated with 11 (FIG. 26A-iii).

Also tested was whether the light could control the drug dose, which is a major advantage of an external stimulus. Thus, light-dose dependent cell survival was determined (FIG. 23B). MCF-7 cells were treated with 11 (25 nM). After 24 hr of incubation, the cells were exposed to the visible light (540±10 nm, 8 mW/cm$^2$) for 0-20 min. The cell damage was dependent on light dose. The results suggested that the drug dose could be controlled by the light dose with a singlet oxygen-mediated release strategy.

Last, it was determined that the conjugate (11) with dPS was much more stable than a conjugate with non-dPS. Under low intensity fluorescent lamp (0.8 mW/cm$^2$), 96% of 11 was intact even after 48 h while only 5% of a conjugate with a non-dPS was intact after 3 h.

In conclusion, the Experimental results demonstrated a novel strategy of double activatable PDs in tissue culture model with several significant advancements. Almost 99% of the prodrug released parent drug in 30 min by the irradiation with very low intensity light. Un-modified cancer drugs were released by visible light irradiation via photo-unclick chemistry while modified drugs (e.g. formulated drugs) were released from previously tested linkers, vinyl diether or dithioether linkers. The dPS was used to make the double activatable PDs, which could provide more precisely controlled release of drugs in cells. The cell-kill effect of the released drugs was demonstrated, which could be controlled by light dose. In addition, dPS made the conjugate more stable than a conjugate with a non-dPS against the unwanted photo-degradation.

It is envisioned that the proposed singlet oxygen-mediated release strategy will be applicable for other drug delivery systems, where a new effective way of drug release control is a key need. The facile synthesis of aminoacrylate linker can be easily adopted for polymers, dendrimers, and other nano-carrier platforms. The proposed strategy can provide versatility in terms of drugs, PSs, and activation mechanisms of dPS. In particular, since the release was mediated by singlet oxygen, any combination of a PS and corresponding light can be used for release. Given the current availability of PSs, almost any wavelength between 400-800 nm can be used for the activation.

Supplementary Information for Example 4

Experimental Section:

High-resolution mass (HRMS) analyses were performed using an Agilent 6538 UHD Accurate Mass QTOF (Santa Clara, Calif.) equipped with an electrospray ionization source in positive and/or negative ion mode. NMR spectra were recorded at 25° C. on a VXR 300, 400, or 500 MHz spectrometer. $^1$H chemical shifts were expressed in parts per million (ppm) based on the residual solvent signal in $CDCl_3$ or DMSO-$d_6$. All solvents and reagents were used as obtained from Sigma Aldrich and Thermo Fisher Scientific unless otherwise stated. Purity was evaluated by analytical HPLC using waters HPLC system (waters-501 solvent delivery systems, waters 486 UV detector, a U6K-03696 auto-injector), coupled to a chromatography data system N2000. Mobile phase was pumped at a flow-rate of 0.3 mL/min. μBondapak $C_{18}$ (5 μM) column (250×4.6 mm I.D. 12109949TS) was used, which was preceded by a guard column containing $C_{18}$/Corasil Bondpak (particle size 37-50 μM). Detection was effected at 313, 310, or 370 nm and isocratic condition was used. Reaction progress was monitored by analytical TLC (silica gel matrix on aluminum plate, Sigma-Aldrich, cat # Z193291) and most products were visualized by UV light. Column chromatography was accomplished on silica gel (40-63 μm) from Sorbent Technologies. The reaction temperatures are indicated as the temperature of the sand bath.

Synthesis and Characterization of 2',4',5',7'-tetraiodo-5(6)-carboxyfluorescence (1a,b) (Scheme 6)

To a solution of 5(6)-carboxyfluorescein (0.38 g, 1 mmol) and iodine (4 mmol) dissolved in water (10 mL), a solution of NaI (0.15 g, 1 mmol) and $NaHCO_3$ (0.08 g, 1 mmol) dissolved in water (1 mL) were added while stirring for 10 min. The reaction mixture was then heated at 120° C. for 4 h. After cooled to room temperature, the solution was poured into cold water (15 mL) and neutralized with 0.1 M HCl. The chilled solution was then filtered, washed with saturated sodium thiosulphate solution to remove the excess of iodine. The obtained solid was washed again with cold water and then recrystallized from a mixed solvent ethyl alcohol:water (0.1:1) to g 1 (0.73 g, 83%) as red powder (1a:1b=1:1). HRMS (ESI, m/z) $[M+H]^+$, calculated for $C_{21}H_9I_4O_7$: 880.6449. found: 880.6499.

5-isomer (1a) (Scheme 6)

$^1$H-NMR ($CDCl_3$, 300 MHz): δ 7.33 (s, 2H, H-1', 8'), 7.56 (br d, J=12.9 Hz, 1H, H-7), 8.27 (br s, 1H, H-6), 8.68 (s, 1H, H-4), 10.18 (br s, 1H, Ph-OH, exchangeable with $D_2O$).

6-isomer (1b) (Scheme 6)

$^1$H-NMR (CDCl3, 300 MHz): δ 2.45 (s, 6H, 2 CH3), 7.20 and 7.22 (each s, 2H, H-1', 8'), 7.90 (s, 1H, H-7), 8.45 (dd, J=8.1 Hz, J=11.4 Hz, 2H, H-4, 5).

Synthesis of 3',6'-diacetyl-2',4',5',7'-tetraiodo-5(6)-carboxyfluorescein (2a,b) (Scheme 6)

One or two drops of dry-pyridine were added to the solution of compound 1 (0.44 g, 0.5 mmol) in acetic acid (1 mL) and then the solution was stirred for 3 h. After the reaction was completed, the solution was neutralized with 0.1 M HCl, and concentrated under reduced pressure at 30° C. The residue was purified by flash column chromatography using a mixture of EtOAc and n-hexane (1:4) as an eluting solvent to give 2 (0.39 g, 81%) as colorless powder (2a:2b=1:1). HRMS (ESI, m/z) $[M+H]^+$, calculated for $C_{25}H_{13}I_4O_9$: 964.6660. found: 964.6732.

5-isomer (2a) (Scheme 6)

$^1$H-NMR (CDCl3, 300 MHz): δ 2.45 (s, 6H, 2 CH3), 7.26 (br s, 2H, H-1', 8'), 7.35 (br s, 1H, H-7), 8.20 (d, J=8.1 Hz, 1H, H-6), 8.80 (s, 1H, H-4).

6-isomer (2b) (Scheme 6)

1H-NMR (CDCl3, 300 MHz): δ 2.45 (s, 6H, 2 CH3), 7.20 and 7.22 (each s, 2H, H-1', 8'), 7.90 (s, 1H, H-7), 8.45 (dd, J=8.1 Hz, J=11.4 Hz, 2H, H-4, 5).

Synthesis of compounds 3-5 (Scheme 7)

A mixture of 7-hydroxy-5-methyl-coumarin (0.18 g, 1 mmol) [SN-38 (0.39 g, 1 mmol) or CA-4 (0.32 g, 1 mmol)], 2-propynoic acid (0.18 mL, 3 mmol), N,N'-dicyclohexylcarbodiimide (DCC, 0.21 g, 1 mmol), and 4-dimethylaminopyridine (DMAP, 0.12 g, 1 mmol) was dissolved in anhydrous dichloromethane (10 mL) [or anhydrous DMF (10 mL) for SN-38 and CA-4].[85,86] The solution was stirred under nitrogen at −10° C. for 1 h and then at room temperature for 4-96 h, except for SN38 [SN38 solution was stirred under nitrogen at −10° C. for 4 h]. After the reaction was completed, white precipitate (dicyclohexylurea) was removed by filtration through a fritted Büchner funnel (G3). The filtrate was washed twice with 50 mL portions of 0.5 M aqueous citric acid and twice with 50 mL of 0.5 M aqueous sodium bicarbonate solution. [In the case of SN-38 the filtrate was washed with water instead of the 0.5 M sodium bicarbonate solution.] During this procedure, some additional dicyclohexylurea was precipitated, which was again removed by the filtration. The organic solution was then dried over anhydrous sodium sulfate and evaporated under reduced pressure at 30° C. The residue was purified by flash column chromatography using a mixture of EtOAc and n-hexane [1:0.25 (1:1.25 for 4 or 1:1 for 5)] as an eluting solvent to provide corresponding product 3 (4, or 5) as colorless needles.

Compound 3 (Scheme 7)

Yield, 0.17 g (74%), 1H-NMR (CDCl3, 300 MHz): δ 2.44 (s, 3H, CH3), 3.15 (s, 1H, CH), 6.30 (s. 1H, H-3), 7.14 (dd, J5,6=9.0 Hz, 4J5,8=2.1 Hz, 1H, H-5), 7.19 (d, 4J5,8=2.1 Hz, 1H, H-8), 7.64 (d, J5,6=9.0 Hz, 1H, H-6). HRMS (ESI, m/z) [M+H]+, calculated for C13H9O4: 229.0423. found: 229.0493.

Compound 4 (Scheme 7)

Yield, (0.26 g, 59%), 1H-NMR (CDCl3, 300 MHz): δ 0.87 (t, J=7.5 Hz, 3H), 1.28 (t, J=7.2 Hz, 3H), 1.86 (br s, 2H), 3.17 (br d, J=6.9 Hz, 2H), 4.93 (s, 1H, CH), 5.33 (s, 2H), 5.43 (s, 2H), 6.51 (s, 1H, exchangeable with D2O), 7.33 (s, 1H), 7.78 (d, J=9.0 Hz, 1H), 8.22 (d, J=4.5 Hz, 1H), 8.24 (d, J=9.0 Hz, 1H). HRMS (ESI, m/z) [M+H]+, calculated for C25H20N2O6: 444.1321. found: 444.1395.

Compound 5 (Scheme 7)

Yield, (0.25 g, 67%), 1H-NMR (CDCl3, 300 MHz): δ 3.03 (s, 1H), 3.70 (s, 6H), 3.83 (d, J=4.2 Hz, 6H), 6.47 (d, J=3.8 Hz, 4H), 6.87 (d, J=8.7 Hz, 1H), 7.05 (s, 1H), 7.15 (d, J=7.8 Hz, 1H). HRMS (ESI, m/z) [M+H]+, calculated for C21H21O6: 369.1260. found: 369.1335.

Synthesis of compounds 6-8 (Scheme 7)

4-Piperidinemethanol (0.06 g, 0.5 mmol) and compound 3 (0.11 g, 0.5 mmol) [4 (0.22 g, 0.5 mmol) or 5 (0.19 g, 0.5 mmol)] were dissolved in dry THF (5 mL), and the solution was stirred at room temperature for 30-45 min. The solvent was removed under reduced pressure at room temp to give the crude product which was then purified by column chromatography using ethyl acetate:hexane (7:3 or 8:3) to give compound 6 (7 or 8).

Compound 6 (Scheme 7)

Yield, 0.14 g (82%), 1H-NMR (DMSO-d6, 300 MHz): δ 1.25-1.38 (m, 3H), 1.77-1.88 (m, 3H), 2.39-2.45 (m, 3H), 3.09 (br s, 2H), 3.49-3.64 (m, 4H), 4.80 (br s, 1H, exchangeable with D20), 6.23 (s. 1H, H-3), 6.83 (br s, 1H, H-8), 7.11 (d, J5,6=8.1 Hz, 1H, H-5), 7.58 (br s, 2H, H-6, 1H). HRMS (ESI, m/z) [M+H]+, calculated for C19H22NO5: 344.1420. found: 344.1497.

Compound 7 (Scheme 7)

Yield, 0.21 g (75%), 1H-NMR (DMSO-d6, 300 MHz): δ 0.87 (t, J=7.5 Hz, 3H), 1.12-1.16 (m, 2H), 1.25-1.30 (m, 3H), 1.64-1.74 (m, 3H), 1.84-1.88 (br s, 2H), 3.27-3.31 (m, 6H), 3.71 (s, 2H, CH2), 4.53 (s, 1H, exchangeable with D20), 4.87 (d, Jtrans=13.2 Hz, 1H), 5.31 (s, 2H), 5.42 (s, 2H), 6.50 (s, 1H, exchangeable with D20), 7.31 (s, 1H), 7.60 (d, J=9.3 Hz, 1H), 7.64 (d, Jtrans=13.2 Hz, 1H), 7.88 (s, 1H), 8.14 (d, J=8.7 Hz, 1H). HRMS (TOF-MS ES+, m/z) [M+H]+, calculated for $C_{31}H_{33}N_3O_7$: 559.2. found: 559.3.

Compound 8 (Scheme 7)

Yield, 0.17 g (70%), 1H-NMR (DMSO-d6, 300 MHz): δ 1.08-1.16 (m, 2H), 1.59-1.70 (m, 5H), 3.26 (t, J=6.0 Hz, 1H), 3.30 (br s, 4H), 3.61 (s, 6H, 2×OCH3), 3.63 (s, 3H, OCH3), 3.70 (s, 3H, OCH3), 4.50 (dd, J=4.8 Hz, J=5.4 Hz, 1H, exchangeable with D20), 4.72 (d, Jtrans=12.9 Hz, 1H), 6.43 (d, Jtrans=12.3 Hz, 1H), 6.50 (d, Jtrans=12.3 Hz, 1H), 6.54 (s, 2H, 2", 6"-H), 6.89 (s, 1H, 2'-H), 7.08 and 7.00 (each d, each J=8.4 Hz, each 1H, 5', 6'-H), 7.43 (d, Jtrans=13.2 Hz, 1H). HRMS (ESI, m/z) [M+H]+, calculated for C27H34NO7: 484.2257. found: 483.2330.

Synthesis of compounds 9-11 (Scheme 7)

A mixture of coumarin 6 (0.09 g, 0.25 mmol) [7 (0.14 g, 0.25 mmol) or 8 (0.12 g, 0.25 mmol)], 2 (0.32 g, 0.33 mmol), and N,N"-dicyclohexylcarbodiimide (DCC, 0.11 g, 0.5 mmol) was added in anhydrous dichloromethane (10 mL) and the solution was stirred under nitrogen at −10° C. for 12-14 h. After the reaction was completed, white precipitate (dicyclohexylurea) was removed by filtration through a fritted Büchner funnel (G3), and the filtrate was washed twice with 50 mL portions of 0.5 M citric acid and twice with 50 mL of 0.5 M sodium bicarbonate solution. [In the case of 7 the filtrate was washed with water instead of 0.5 M sodiumbicarbonate solution.] During this procedure, some additional dicyclohexylurea was precipitated, which was removed by filtration. The organic solution was dried over anhydrous sodium sulfate and evaporated under reduced pressure at 30° C. The residue was purified by flash column chromatography using a mixture of EtOAc and n-hexane (0.5:4 or 1:3 or 1.25:5) as eluting solvent to give corresponding products 9 [10, or 11] as colorless needles.

Compound 9 (5- and 6-isomers 1:1, 9) (Scheme 7)

Yield, 0.18 g (56%). 1H-NMR (DMSO-d6, 400 MHz): δ 1.19-1.24 (m, 4H), 1.25 (br s, 4H), 2.03 (br s, 2H), 2.17 (s, 3H), 2.19 (br s, 6H), 2.39 (s, 3H), 2.45 (br s, 6H), 3.45-3.49 (m. 4H), 4.10-4.15 (m, 4H), 4.23 (d, J=5.2 Hz, 2H), 4.30 (d, J=5.2 Hz, 2H), 4.38 (br d, J=14.4 Hz, 2H), 6.13 (s. 2H), 6.82 (br s, 2H), 6.83 (s. 1H), 7.18 (br s, 4H), 7.46 (s, 1H), 7.48 (br s, 2H), 7.65 (br s, 1H), 7.66 (br s, 1H), 7.79 (br s, 2H), 8.17 (d, J=8.0 Hz, IH), 8.36-8.0 (dd, J=7.2 Hz, J=8.3 Hz, 2H), 8.71 (s, 1H). HPLC purity: tR 11.02 min (95.9%); HRMS (ESI, m/z) [M+H]+, calculated for C44H32I4NO13: 1289.7974. found: 1289.8035.

Compound 10 (5- and 6-isomers, 1:1, 10) (Scheme 7)

Yield, 20 g (53%). 1H-NMR (CDCl3, 500 MHz): δ 1.04 (t, J=7.5 Hz, 3H), 1.14 (br s, 3H), 1.34 (t, J=7.5 Hz, 6H), 1.56-1.67 (m, 5H), 1.83-1.94 (m, 13H), 2.08-2.21 (m, 4H), 2.45 (br s, 6H), 2.62 (br s, 8H), 3.11-3.21 (m, 4H), 3.46 (s, IH), 3.65-3.46 (s, 1H), 3.65 (d, J=6.5 Hz, 2H), 4.33 (d, J=6.5 Hz, 2H), 4.90 (d, Jtrans=12.3 Hz, 1H), 4.94 (d, Jtrans=12.3 Hz, 1H), 5.28 and 5.32 (each s, each 1H, 2H), 5.73 and 5.77 (each s, each 1H, 2H), 7.19 (br s, 3H), 7.34 (s, 1H), 7.60 (br s, 1H), 7.63 (d, Jtrans=12.3 Hz, 1H), 7.67 (d, Jtrans=12.3 Hz, 1H), 7.71 (br s, 2H, 1H), 7.79 (br s, 1H), 7.84 (br s, 2H), 8.17 (s, 1H), 8.18 (s, 1H), 8.24 (br s, 1H), 8.25 (br s, 1H), 8.38 (br s, 1H), 8.40 (br d, J=8.5 Hz, 2H), 8.72 (s, 1H, H-4). HPLC purity: tR 11.16 min (96.1%); HRMS (ESI, m/z) [M+H]+, calculated for C56H44I4N3O15: 1504.8873. found: 1505.8944.

Compound 11 (5- and 6-isomers, 1:1, 11) (Scheme 7)

Yield, 0.23 (64%). 1H-NMR (DMSO-d6, 400 MHz): δ 1.19-1.90 (m, 4H), 1.24-1.28 (m, 4H), 2.04 (br s, 4H), 2.45 (br s, 6H), 3.45-3.52 (m. 3H), 3.73 (br s, 12H), 3.80, 3.81, 3.83, 3.84 (each s, each 3H, 12H), 4.10-4.15 (m. 3H), 4.24 (d, J=6.4 Hz, 2H), 4.29 (d, J=6.4 Hz, 2H), 4.83 (d, Jtrans=13.2 Hz, 1H), 4.86 (d, Jtrans=13.2 Hz, 1H), 6.40 (br d, Jtrans=12.3 Hz, 2H), 6.42 (br d, Jtrans=12.3 Hz, 2H), 6.53 (br s, 4H), 6.82 (s, 1H), 6.84 (s, 1H), 7.05 and 7.06 (each d, each J=8.8 Hz, each 1H, 2H), 7.09 and 7.14 (each d, each J=8.8 Hz, each 1H, 2H), 7.15 (br s, 3H), 7.33 (br s, 2H), 7.49 (d, Jtrans=12.4 Hz, 1H), 7.52 (d, Jtrans=12.4 Hz, 1H), 7.79 (br s, 1H), 8.20 (d, J=8.8 Hz, 1H), 8.72 (s, 1H), 8.36-8.8 (dd, J=7.2 Hz, J=8.0 Hz, 2H). HPLC purity: tR 11.36 min (97.4%); HRMS (ESI, m/z) [M+H]+, calcd for C52H44I4NO15: 1429.8811. found: 1429.8853.

Dark Toxicity Procedure for Cell Viability.

MCF-7 cells (5,000 cells/well) were seeded in 96 well plates. After the plates were incubated for 24 hr, the culture medium was aspirated and the cells were washed with cold PBS (100 µL) once. Then, prodrug in the 200 µL culture media was added to cells. The final concentrations ranging from 1 nM to 1 µM were used to perform concentration dependent cell viability and 25 nM prodrug was used to perform time dependent drug release study. After 96 hr incubation, the cell viability was determined by MTT assay detailed below. The experiments were performed in triplicate. $IC_{50}$ values were calculated with GraphPad Prism 5.

Phototoxicity Procedure for Cell Viability.

Figure 27:
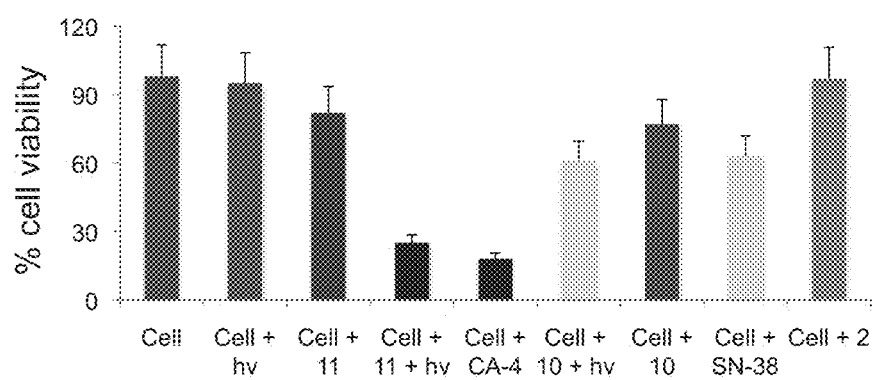
FIG. 27 is a graphical representation of the effects of different conditions on the cell viability of MCF-7 cells. The concentration of samples used was 0.05 µM, and the light exposure time was 30 min.

The cells were prepared and treated with the prodrugs the same as the dark toxic study except for the following. After incubation of cells with prodrug for 24 hr, the wells were irradiated (LC122-A from Lumacare™, 540±10 nm, 8 mW/cm$^2$) for 30 min (or 5 min, 10 min, 15 min, and 20 min for time-dependent drug release study). After being irradiated, the medium solution (200 µL/well) from each well in the plate was moved to another well with untreated cells. After an additional 96 hr incubation, the cell viability was determined by MTT assay. (FIG. 27).

MTT Assay Procedure.

Cell viability was assessed by MIT assay.[89] In brief, after thoroughly washing the cells 2× with PBS buffer, the cells were treated with 200 µL 0.5 mg/mL MIT (3-(4,5-dimethylthiazol-2-yl)-2,5-diphenyltetrazolium bromide, a yellow tetrazole). Subsequently, the cells were incubated at 37° C. under a humidified atmosphere of 5% $CO_2$ for 4 h. After 4 h of incubation, the solution from each well was taken out, and washed with PBS one time and added 100 µL DMSO. The plates were shaken at room temperature for 10 min and read immediately at 570 nm on a microplate reader (Spectra max, Molecular devices). Cell viability (%) was expressed as a ratio of treated cells to control cells.

Procedure for Live-cell Fluorescence Imaging.

MCF-7 cells suspended in 200 µL medium were seeded at 5,000 cells/wall in 96-well black microplate (3603, Cat# CLS3603-48EA). After the plates were incubated for 24 h, the culture medium was aspirated and the cells were washed with cold PBS (100 µL) once. Then, samples (1 µM 2 or 25 nM 11) in the 200 µL culture media were added to cells. After 24 h incubation, the wells were irradiated from the bottom direction (LC122-A from Lumacare™, 540±10 nm, 8 mW/cm$^2$ for 30 min). To prevent irradiation of half of the wells, right half of the wells was blocked by a black tape (from THORLABS, Cat# T743-1.0). After further 96 h of incubation, live cell stain assay was performed using calcein AM (from Molecular Probes, Tervigen Cat#4892-010-K) according to the manufacturer supplied standard protocols. All images were obtained with an Olympus IX51 inverted microscope with green fluorescence channel to visualize live cells. All images were taken at 10× magnification. Each experiment was repeated at least three times.

Example 5

Site-Specific and Far-Red Light-Activatable Prodrug of Combretastain A-4 Using Photo-Unclick Chemistry A major problem of treatment with anticancer chemotherapy drugs is that such treatment is often toxic to non-cancerous cells, creating systemic side effects. Various strategies, including tumor-targeted drug delivery, target site-activated pro-drugs, and combination therapy, have been proposed to minimize such systemic side effects.[66-70] These strategies have a shared goal of keeping the systemic concentration of the drug lower than its toxic level while keeping the drug concentration at tumor sites above the effective concentration.

With that goal, photodynamic therapy (PDT) provides an excellent foundation for inspiring a new strategy for treating tumors. In PDT, non-toxic photosensitizers are activated by tissue-penetrable light (630-800 nm in the red and NIR range) to locally generate short-lived reactive oxygen species (ROS) such as singlet oxygen (SO)[82-84] to ablate cancer cells while causing only minimal side effects. The primary factor for the selective tumor ablation is the focused irradiation on tumors. In PDT, the tissue-penetrable light can be used as an excellent tool for providing spatiotemporally controlled release of toxic chemical species.

Figure 28:
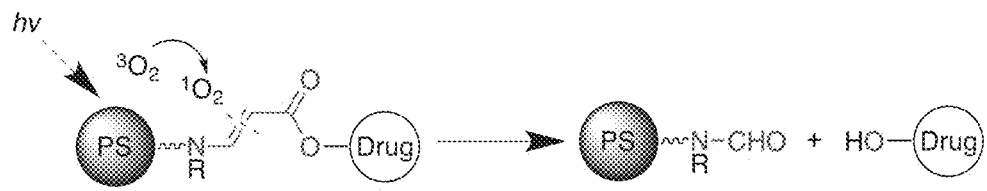
FIG. 28 schematically represents the release of a drug from tissue-penetrable light-activatable prodrug via photounclick chemistry.

While UV and short-visible light have been extensively studied for spatiotemporally controlled release of bioactive molecules (called "caged compounds"),[74,75] application of the tissue-penetrable light has been extremely limited because of the lack of chemistry that can translate the photonic energy to chemical bond cleavage. Recently, a "smart" strategy was proposed that takes advantage of the photosensitization and unique chemistry of SO.[5,7,14,35,43] Electron-rich olefins can be cleaved by SO that is generated from the photosensitization (light+photosensitizer). However, there are still some key limitations in this strategy for broader application. These include limited SO-cleavable linkers (to vinyl diether and vinyl thiodiether), facile synthetic tools for the cleavable linkers, regeneration of parent drugs, and demonstration of functionality using in vivo systems. As is disclosed herein, a "photo-unclick chemistry" of aminoacrylate has been discovered, which overcomes all of these issues (FIG. 28).[86]

Figure 29:
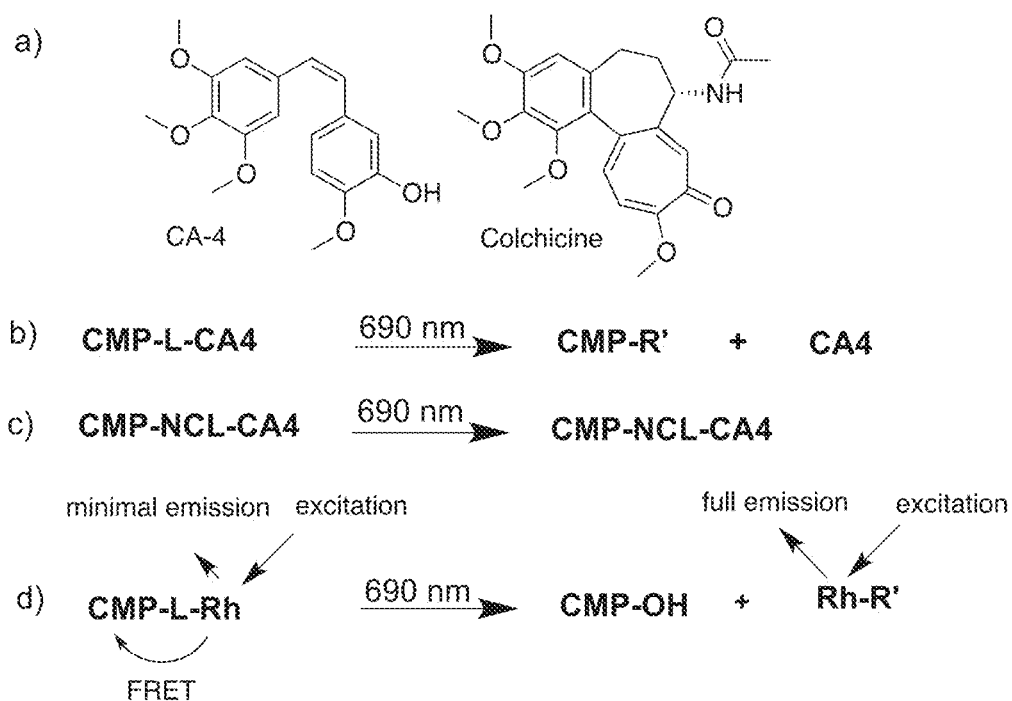
FIG. 29 illustrates the structures of CA4, colchicine, the prodrug CMP-L-CA4, and various pseudo-prodrugs.

Combretastains are well-known tubulin-binding agents that were isolated from *Combretum caffirum*.[90,91] Combretastain A-4 (CA4) is one of the most important natural molecules that strongly inhibits tubulin polymerization.[92] The cis isomer is biologically active while the trans isomer has little or no activity.[93] The cis isomer has a very similar configuration to colchicine (FIG. 29a), and it binds to the colchicine binding site of β-tubulin.21,[94,95] CA4 was chosen for a prodrug design because of its size and simple structure with a phenolic group and because of its potent in vitro cytotoxicity with a nano-molar $IC_{50}$. In addition, it was expected that the prodrug of CA4 should have significantly lower cytotoxic activity because of the bulky PS and linker at the 3' position of CA4, disturbing the CA4 binding conformation inside the colchicine binding small pocket of β-tubulin.

Based on previous studies, it was hypothesized that this novel prodrug strategy could be used to achieve antitumor effects in animal models by locally releasing active anticancer agents upon irradiation. A CA4 prodrug [CMP-L-CA4] and two pseudo-prodrugs (CMP-NCL-CA4 and CMP-L-Rh) (FIGS. 29C and 29D) were prepared. Core-modified porphyrin (CMP) was selected as a photosensitizer to generate SO using tissue-penetrable far-red light (690 nm). CMP-NCL-CA4 was prepared as an analog of CMP-L-CA4 that cannot release CA4. CMP-L-Rh was used as a special fluorescence probe that emits bright rhodamine fluorescence only after cleavage of the linker. The following discloses the synthesis of these compounds, the cleavage of the linker of CMP-L-CA4 in CDCl$_3$, and the in vitro and in vivo biological activities of these prodrugs.

Figure 30:
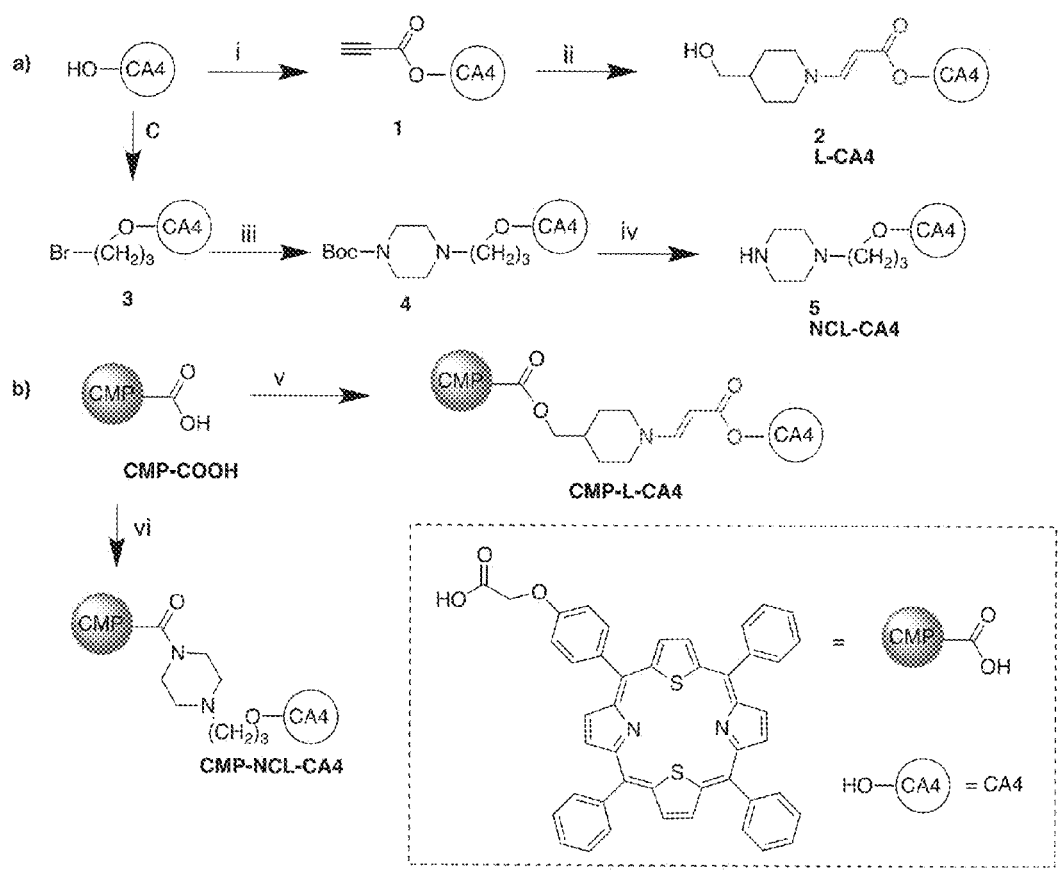
FIG. 30 schematically represents the synthesis of CMP-L-CA4 and CMP-NCL-CA4, wherein the reagents and conditions comprise: (i) prolionic acid, DCC, DMAP, room temp, 24 h, 73%; (ii) 4-piperidinemethanol, THF, room temp, 30 min, 94% yield; (iii) 1,3-dibromopropane, anhydrous K$_2$CO$_3$, acetone, reflux, 12 h, 84%; (iv) n-boc-piperazine, anhydrous K$_2$CO$_3$, anhydrous DMF, room temp, 8 h, 87% yield; (v) compound 4, TFA, anhydrous DCM, room temp, 1 h; (f) compound 2 (L-CA4), DCC, DMAP, anhydrous DCM, room temp, 24 h, 69% yield; (vi) compound 5 (NCL-CA4), DCC, DMAP, anhydrous DCM, room temp, 24 h, 74% yield.

Synthesis of Prodrugs: The synthesis of the prodrugs involved three to four facile and high-yielding reactions (FIG. 30). CA4 was esterified with propynoic acid using DCC and DMAP at 0° C. to give compound 1. The compound 2 (L-CA4) was synthesized in 94% yield through a click (yne-amine reaction) reaction of compound 1 and 4-piperidinemethanol. Then, CMP-L-CA4 was synthesized by esterification of CMP-COOH and 2 in 69% yield. The synthesis of CMP-NCL-CA4 also involved four simple and high-yield steps. The phenolic group of CA4 was alkylated with 1,3-dibromopropane under the basic condition to give the compound 3. The compound 5 (NCL-CA4) was synthesized via the substitution of bromo group by N-boc-piperazine under the basic condition and the deprotection of the boc group using TFA. Finally, CMP-NCL-CA4 was synthesized by the esterification of CMP-COOH and 5 using DCC and DMAP at 0° C. in 74% yield. The purity of CMP-L-CA4 and CMP-NCL-CA4 was confirmed by HPLC to be >95%.

Figure 31:
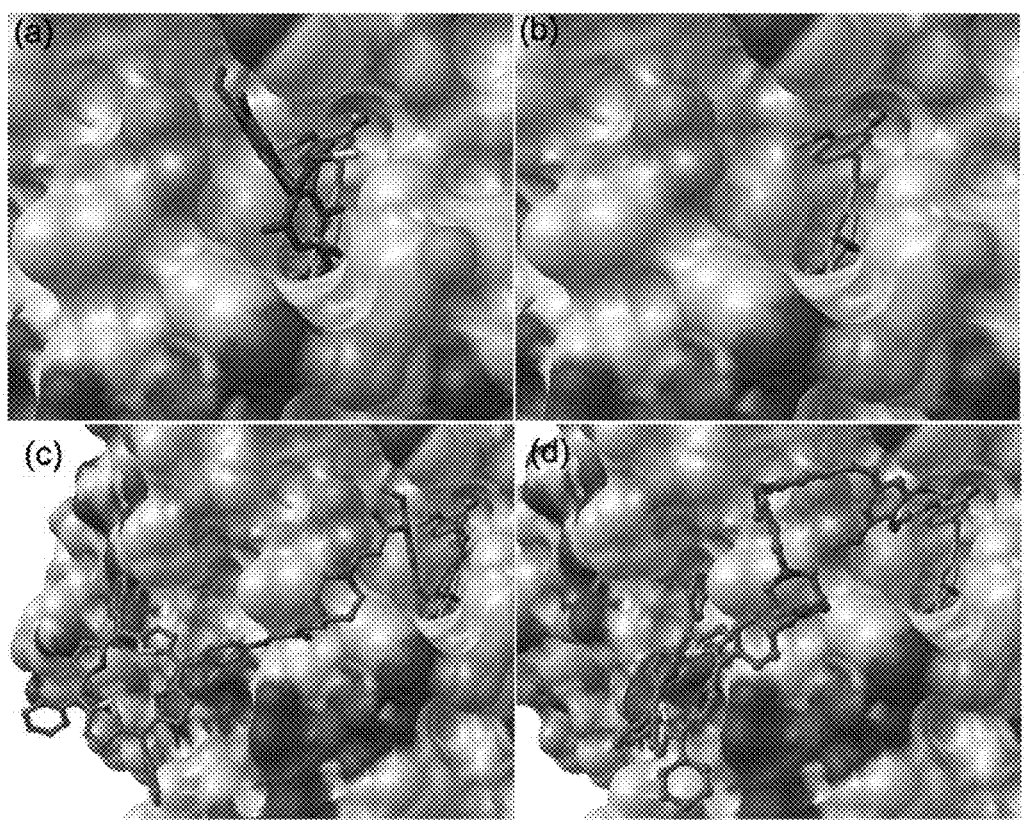
FIG. 31 illustrates an AutoDock-modeled possible binding of CA4 and its prodrugs (CMP-L-CA4 and CMP-NCL-CA4) at the colchicine binding site (PDB code 1SA0): (a) colchicine (blue) and CA4 (green), (b) CA4 (green), (c) CMP-L-CA4 (purple) and CA4 (green), and (d) CMP-NCL-CA4 (purple) and CA4 (green).

Molecular Docking: To estimate the impact of the bulky groups (i.e., CMP and linkers) of CMP-L-CA4 and CMP-NCL-CA4 on their binding to the colchicine binding site of β-tubulin, molecular docking was performed by using an available high-quality crystal structure of β-tubulin.[96] Since cis-CA4 is a well-known tubulin inhibitor and can inhibit tubulin polymerization by binding at the colchicine binding site[21,94,95], CA4 and prodrugs were docked at the colchicine binding site by using AutoDock 4.0.[97] It was predicted that the binding conformations of the prodrugs were less favored than those of CA4. While CA4 was small enough to fit inside the colchicine binding site (FIGS. 31a and b), the prodrugs were too big to fit inside the pocket (FIGS. 31c and d). Much higher Ki values were predicted for both prodrugs than for CA4 (CMP-L-CA4: Ki=74 µM, CMP-NCL-CA4: Ki=559 µM, and CA4: Ki=16 µM), presumably because of the bulky group (i.e., CMP and a linker). The binding of the prodrugs to the binding pocket might be hindered by the bulky CMP-L or CMP-NCL group. From this modeling study, it was speculated that the prodrugs might have a lower binding affinity to the CA4 target, and thus these might have lower cytotoxic activity than CA4, which is required of the prodrugs.

Figure 32:
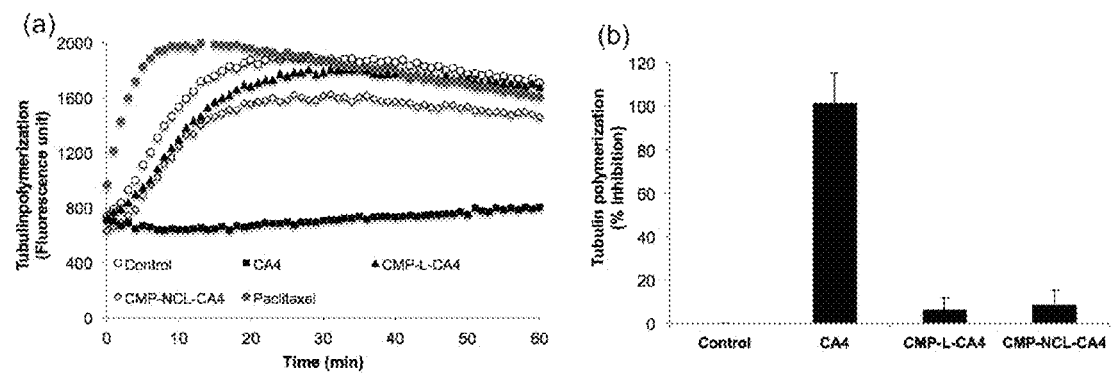
FIG. 32 is a graphical representation of the Effects of 3 µM paclitaxel, CA4, CMP-L-CA4 or CMP-NCL-CA4 on tubulin polymerization: (a) one data set of representative kinetic traces (the other two data are reported in FIGS. 33 and 34 and (b) inhibition of tubulin polymerization by CA4, CMP-L-CA4, or CMP-NCL-CA4 after 1 h incubation at 37° C. (mean±SD of three experiments).
Figure 33:
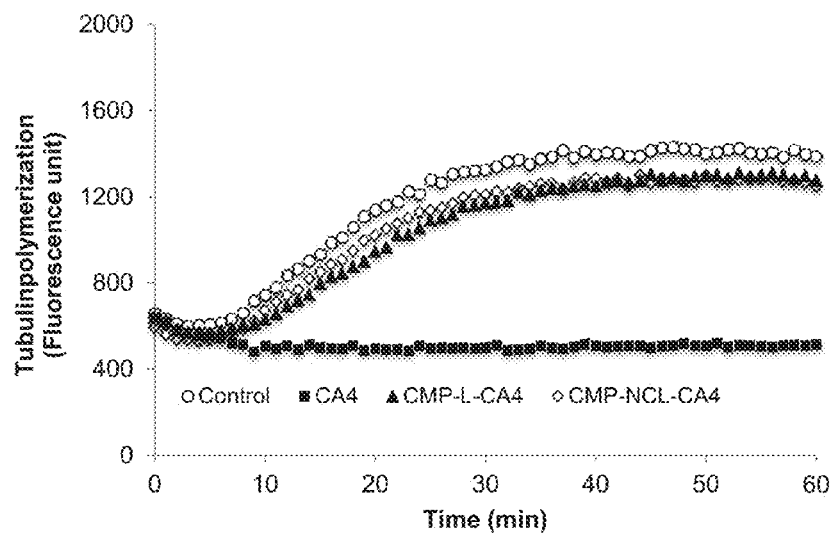
FIG. 33 is a graphical representation of the effects of CMP-L-CA4 and CMP-NCL-CA4 on tubulin polymerization.
Figure 34:
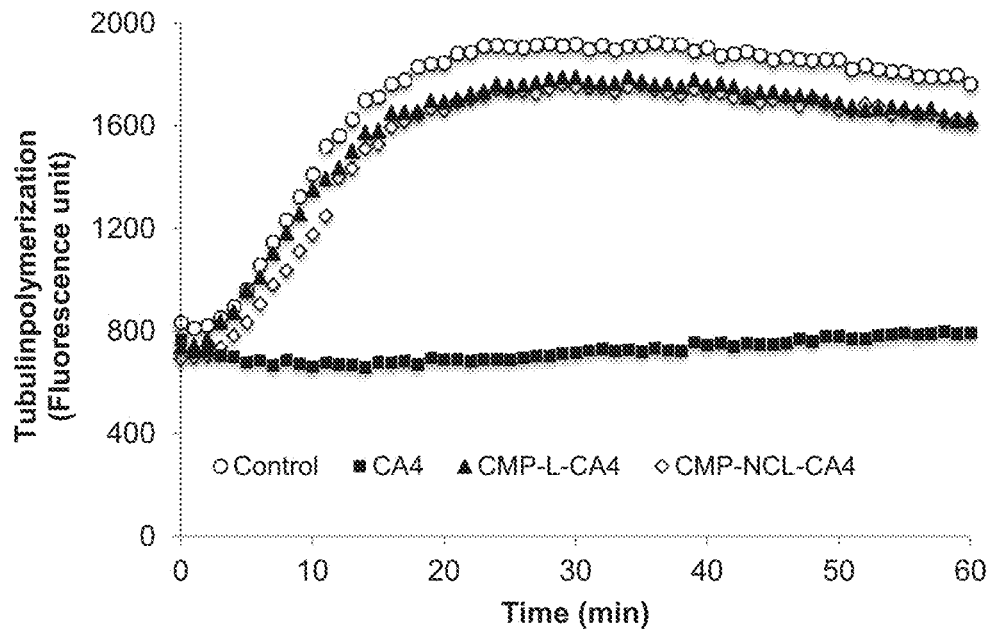
FIG. 34 is a graphical representation of the effects of CMP-L-CA4 and CMP-NCL-CA4 on tubulin polymerization.

Effect of CMP-L-CA4 and CMP-NCL-CA4 on Tubulin Polymerization: A tubulin polymerization assay was conducted to examine whether the two prodrugs had significantly lower activity in the inhibitory activity for tubulin polymerization than the activity of CA4 because of the bulky groups (CMP-L and CMLP-NCL) as predicted by the above docking study. The tubulin polymerization assay data revealed enhanced fluorescence emission as the tubulin polymerized. Paclitaxel and CA4 were used as positive control drugs (a polymerization enhancer and an inhibitor, respectively) in addition to the negative control group (FIG. 32). Additional experiments illustrating the kinetic traces of the effects of 3 µM paclitaxel, CA4, CMP-L-CA4 or CMP-NCL-CA4 on tubulin polymerization are presented in FIGS. 33 and 34. Without any drug (negative control group), tubulin polymerization reached at its maximum at about 20 min. On the other hand, paclitaxel and CA4 had typical patterns of kinetic traces of tubulin polymerization disruptors: an enhancer (paclitaxel) and an inhibitor (CA4). Compared to CA4, both prodrugs had little to no inhibitory ability on tubulin (FIG. 32b). After 1 h, CMP-L-CA4 and CMP-NCL-CA4 had only limited inhibition of polymerization (6 and 9%, respectively); CA4 completely inhibited tubulin polymerization (100%, FIG. 32b). Thus, the bulky groups (CMP-L ad CMP-NCL) may have reduced the binding activity of these prodrugs to tubulin.

Figure 35:
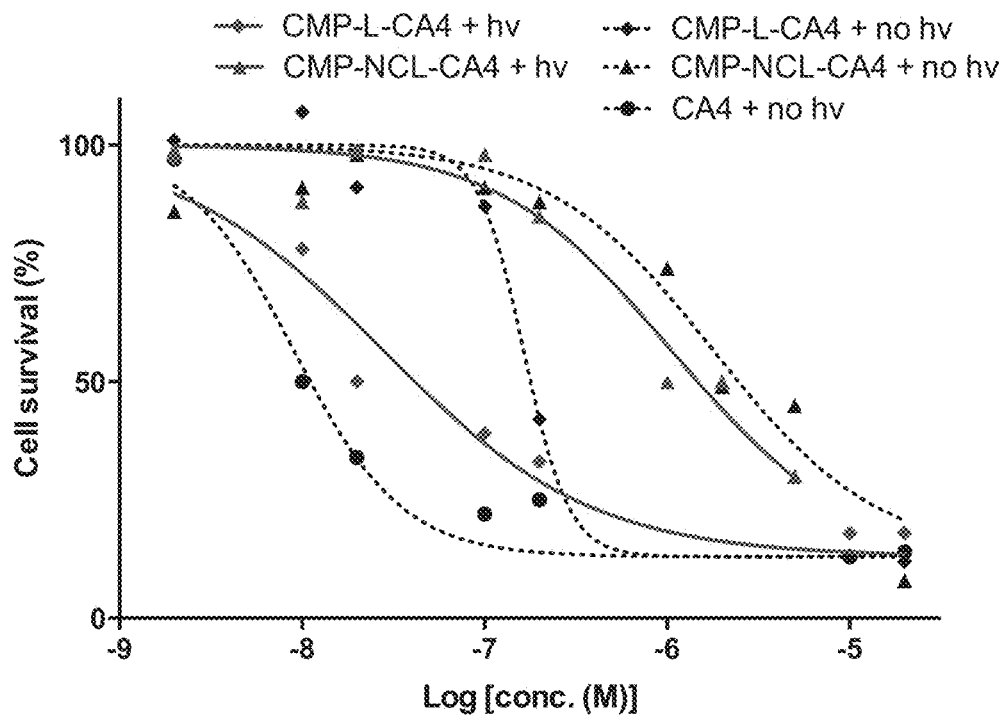
FIG. 35 is a graphical representation of the dark toxicity and phototoxicity of CMP-L-CA4 and CMP-NCL-CA4 and dark toxicity of CA4.

Dark Toxicity and Phototoxicity: The dark toxicity was determined to confirm whether the addition of CMP-L or CMP-NCL to CA4 effectively reduced the cytotoxicity of CA4 (FIG. 35). Indeed, the cytotoxicities of the prodrugs were much lower than that of CA4 itself: IC$_{50D}$=9 nM (CA4), 164 nM (CMP-L-CA4), 1802 nM (CMP-NCL-CA4)—reduction by 18 and 200-fold, respectively. It seemed that the bulky groups, CMP-L and CMP-NCL, reduced the cytotoxic activity of CA4, presumably through the interference of its binding to tubulin as estimated by the modeling study. Interestingly, the CMP-NCL group was more effective than the CMP-L group in masking the activity of CA4.

Phototoxicity was then determined to confirm the enhanced cell damage after the irradiation by the release of CA4 from CMP-L-CA4. Theoretically, two possible mechanisms could damage the cells by [CMP-L-CA4+hv] via either a photodynamic effect (i.e., SO from CMP moiety+hv) and/or the released CA4. On the other hand, only a photodynamic effect could damage cells by [CMP-NCL-CA4+hv]. A 6-fold increase was observed after irradiation in CMP-L-CA4: IC$_{50D}$=164 nM→IC$_{50D}$=28 nM, but an increase by 1.7-fold increase was observed in CMP-NCL-CA4: IC$_{50D}$: 1802 nM→IC$_{50D}$=1063 nM (CMP-NCL-CA4). It seemed that the photodynamic effect (the cytotoxicity by SO) was smaller than the cytotoxic effect by the released CA4 in [CMP-L-CA4+hv].

A Bystander Effect by CMP-L-CA4.

Figure 36:
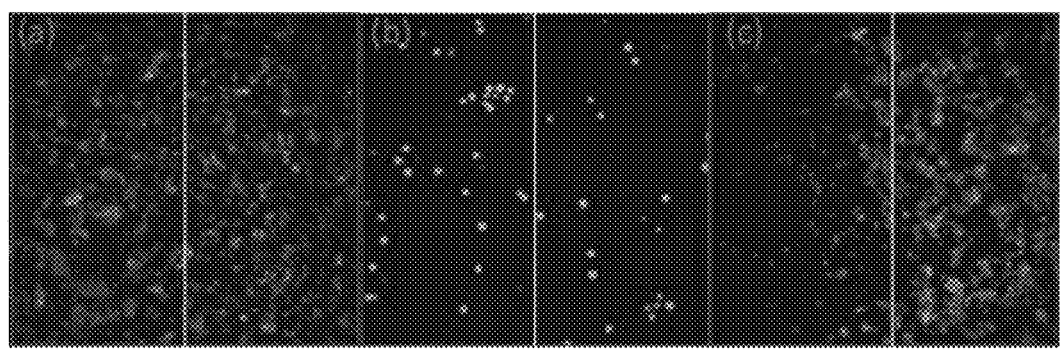
FIG. 36 illustrates fluorescence live cell images of the center of each well treated with (a) control, (b) CMP-L-CA4 (50 nM) and (c) IY69 (5 µM): only the left half of each well was irradiated with 690 nm diode laser (11 mW/cm$^2$ for 15 min). At these concentrations, CMP-L-CA4 and IY69 did not produce significant dark toxicity.

A bystander effect (killing neighboring cells) was found, which means cellular damage was caused by the released CA4, and not by SO, in [CMP-L-CA4+hv] (FIG. 36). SO, the toxic species in PDT, has a very short half-life (~40 ns) in aqueous media and its diffusion distance is estimated to be between 20 and 200 nm.[82-84] Thus, PDT cannot generate a bystander effect. In other words, the SO generated in one cell could not damage neighboring cells. To examine the bystander effect of CMP-L-CA4, only the left half of each well was irradiated, and then visualized the center of the whole well (covering parts of both the irradiated and un-irradiated half) was imaged to determine the number of live cells. As expected, a bystander effect was found for CMP-L-CA4: cells in the non-irradiated side were damaged as much as the irradiated side (FIG. 36b). On the other hand, a potent CMP photosensitizer IY69[23,98] damaged only the cells in the irradiated half of the well (FIG. 36c), resulting from the damage caused by only SO. This clearly demonstrated that CMP-L-CA4 killed the cells mostly by the released CA4.

In Vivo Optical Imaging with the FRET Probe.

Figure 37:
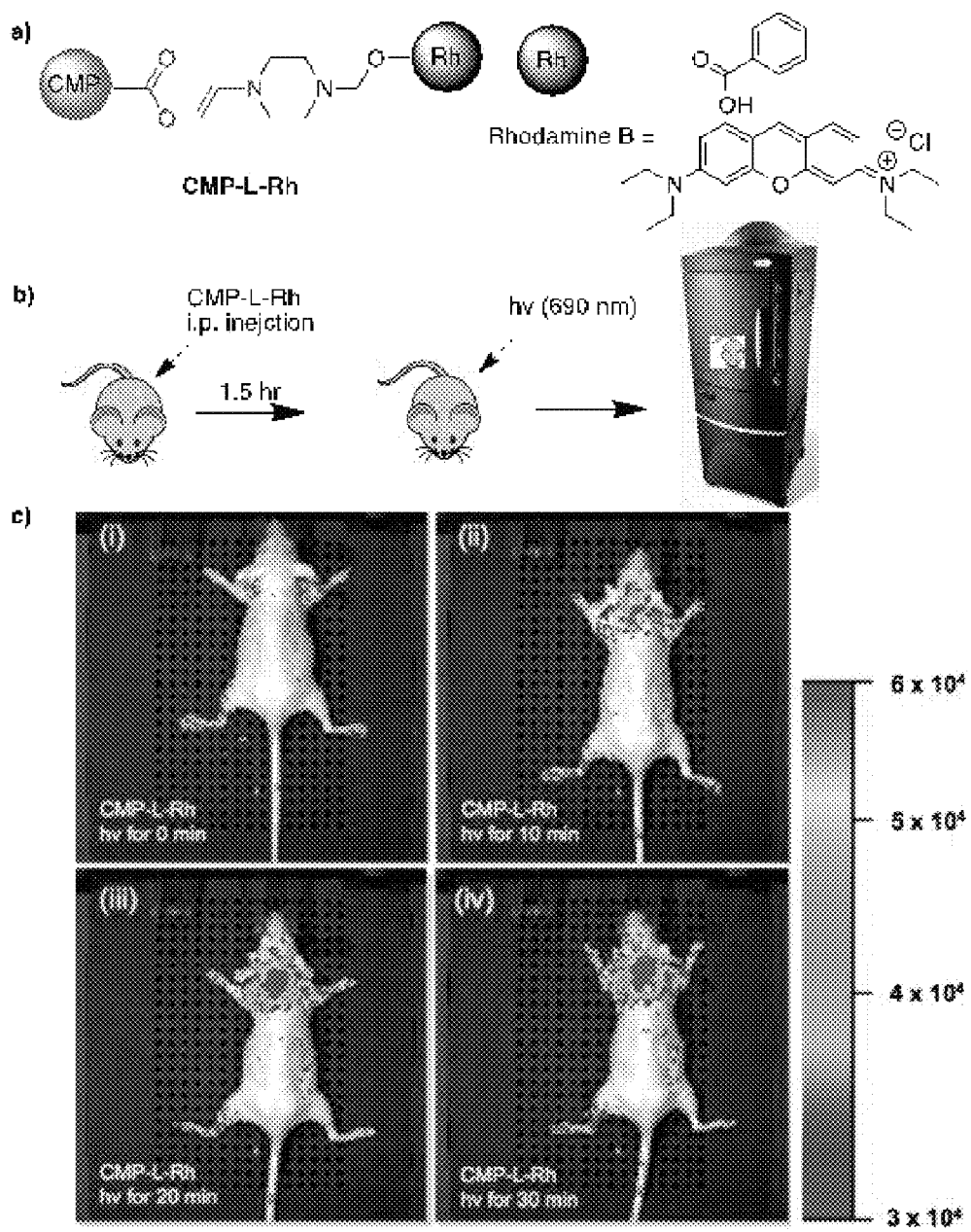
FIG. 37 illustrates an optical in vivo imaging study demonstrating the cleavage of the aminoacrylate linker. Panel A of FIG. 37 schematically represents the structure of the FRET probe (CMP-L-Rh). Panel B of FIG. 37 illustrates the procedure for in vivo optical imaging. Panel C of FIG. 37 presents optical images of the mouse after irradiation for 0 (i), 10 (ii), 20 (iii) and 30 (iv) min with 690 nm diode laser 1.5 hr-post injection of CMP-L-Rh. *scale bar unit: fluorescence arbitrary unit.

The cleavage of the aminoacrylate linker was demonstrated by using an optical in vivo imaging study with a FRET optical probe, CMP-L-Rh (Panels A and B of FIG. 37). An irradiation time-dependent increase in fluorescence emission was observed (Panel C of FIG. 37). The irradiated spot become more intense as irradiation time increased from 10 to 30 min. The corresponding increase in the fluorescence intensity upon irradiation was attributed to the localized release of fluorescent rhodamine dye after the oxidative cleavage of the aminoacrylate linker of the minimally fluorescent CMP-L-Rh. This is the first demonstration of the use of a cleavable SO linker in an animal model.

Antitumor Efficacy.

The antitumor effects of the prodrugs after irradiation were evaluated by using a mouse tumor model: BALB/c mice having s.c. tumors produced by injection of colon 26 cells. After 1.5 h-post i.p. injection of prodrugs, each tumor was irradiated by 690 nm diode laser (360 J/cm$^2$=200 mW/cm$^2$ for 30 min) on days 0, 1 and 2. The treatment conditions were determined from pilot studies although those conditions might not have been the optimal conditions.

Figure 38:
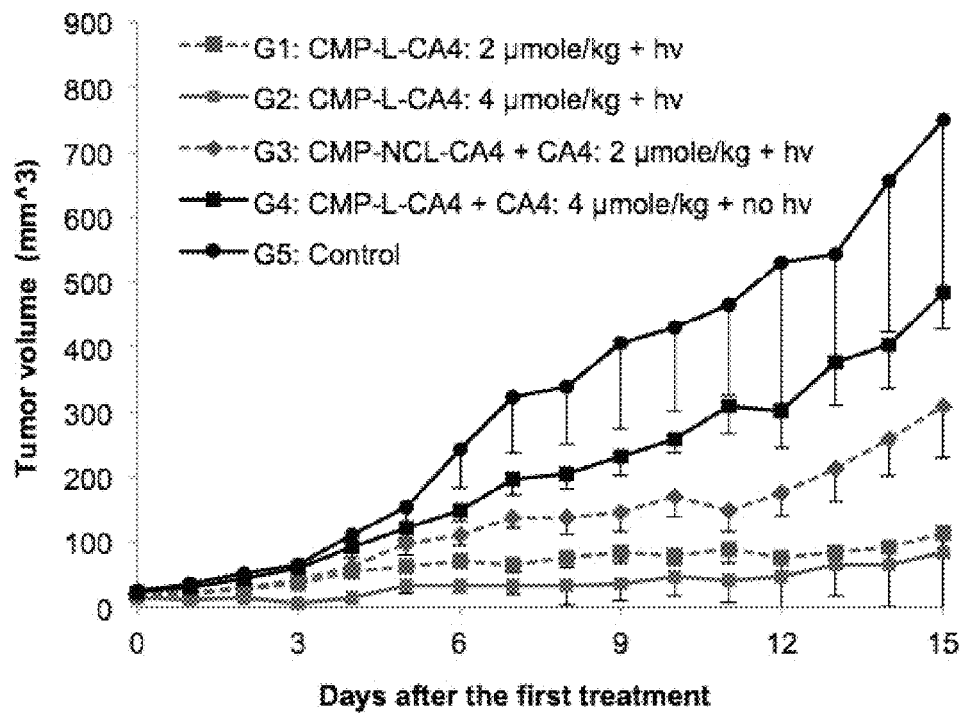
FIG. 38 graphically represents tumor growth curves. Drug administration: once a day on days 0, 1, and 2; hv=360 J/cm$^2$ with 690 nm; 6 mice were used per group except 3 mice were used in the control group. Error bars represent SE.
Figure 39:
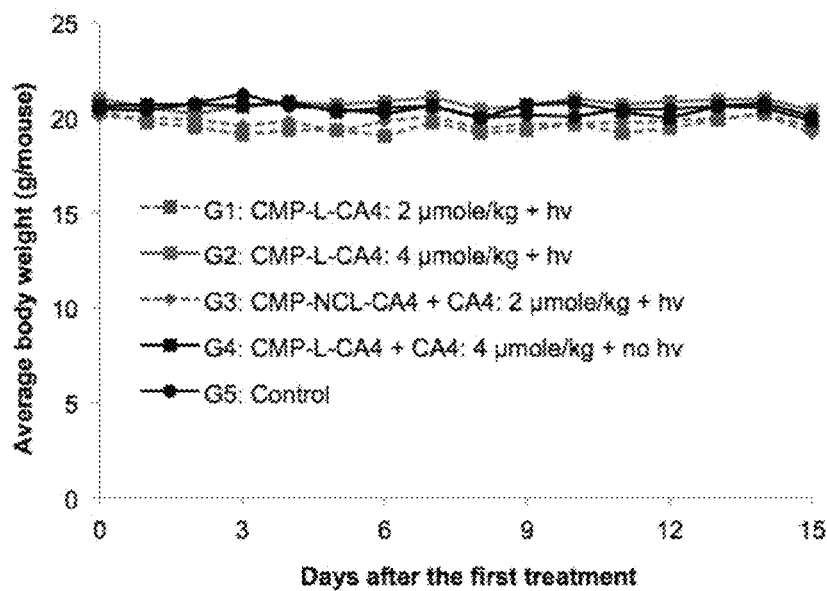
FIG. 39 graphically represents the body weight changes of the mice during the antitumor efficacy study.

A number of interesting results were observed (FIG. 38). First, the animals in the non-irradiated group G4 [CMP-L-CA4+CA4 (4 μmole/kg each)] had similar tumor growth to that of the control animals (G5, P>0.05). It seemed the anti-tumor effects of these two compounds were minimal without irradiation. Second, irradiation produced a significantly better anti-tumor effect (G2 compared to G4, P<0.05). Irradiation improved the anti-tumor effects of CMP-L-CA4, possibly because of the released CA4 and the PDT effect (CMP moiety+hv). Third, G3 group [CMP-NCL-CA4+CA4+hv] had a significant (P<0.05) delay in tumor growth when compared to the tumor growth in the control group G5 (P<0.05). This may have resulted from the PDT effect of CMP-NCL-CA4+hv, because a significant tumor growth delay caused by CA4 itself was not seen at a similar dose in the pilot studies. These data are consistent with the data from a previous report of a minimal CA4-induced antitumor effect even at a very high dose (506 μmole/kg).[99] In addition, signs of necrosis on the treated tumors were also seen, which are typical signs of a PDT effect. Last, but most important, animals in the G1 group [CMP-L-CA4 (2 μmole/kg)+hv] experienced a significantly (P<0.05) superior antitumor effect than animals in the G3 group that mimicked a combination therapy [PDT with CMP-NCL-CA4 plus a systemic CA4 (2 μmole/kg each)+hv]. This was most likely caused by the released CA4. Interestingly, significant loss of body weight was not seen in animals from any group (FIG. 39), which is one of the indicative signs for acute systemic toxicity.

It was demonstrated the application of photo-unclick chemistry in an anticancer prodrug from its synthesis to its in vivo antitumor effects. The prodrug was readily prepared via facile reactions with mild reaction conditions and high yields. The aminoacrylate linker was cleaved fast by the irradiation with tissue-penetrable far-red light (690 nm), releasing the anticancer drug, CA4. The released CA4 effectively damaged neighboring cells through bystander effects. The cleavage of the aminoacrylate linker was also confirmed in mouse tissue by using an in vivo optical imaging with a FRET molecular probe. Most significantly, it was demonstrated that the prodrug CA4 (CMP-L-CA4), which was minimally active in vivo, had an enhanced antitumor effect without any significant signs of acute toxicity. This is the first demonstration of the use of site-specific release of anticancer drug via photo-unclick chemistry in an animal model.

It was envision that this prodrug strategy will be applicable for various clinical needs to reduce the systemic side effects during local chemotherapy, such as localized neoadjuvant chemotherapy and localized adjuvant chemotherapy. In addition, this prodrug strategy can be readily adapted to more advanced drug delivery systems.

Experimental Section

General Experimental Section.

All solvents and reagents were used as obtained from Sigma Aldrich and Thermo Fisher Scientific unless otherwise stated. All reactions were monitored by TLC (silica gel matrix on aluminum plate, Sigma-Aldrich, cat # Z193291). Column chromatography was done using 40-63 μm silica gel from Sorbent Technologies. NMR spectra were recorded at 25° C. with a 300 MHz spectrometer (Varian Mercury). NMR solvents with residual solvent signals were used as internal standards. High-resolution mass spectra (HR-MS) were collected by using an Agilent 6538 UHD Accurate Mass QTOF (Santa Clara, Calif.) equipped with an electrospray ionization source in positive (and/or) negative ion mode at the Mass Spectrometry Facility at University of Oklahoma. Analytical HPLC using HP agilent 1100 was used for the purity evaluation. Mobile phase was pumped at a flow-rate of 0.5 or 0.6 mL/min. Bondapak C (5 μM) column (250×4.6 mm I.D. 12109949TS) was used, which was preceded by a guard column containing C/Corasil Bondpak (particle size 37-50 μM). Detection was effected at 254 nm and isocratic condition was used. GC-MS analyses were performed with HP/Agilent 6890A gas chromatograph with an HP/Agilent 5973C MSD with EI ion source at the Mass Spectrometry Facility at the University of Oklahoma. Power density was measured by thermal sensor (S302C, Thorlabs Inc., Newton, N.J.) and a power meter (PM100D, Thorlabs Inc.). All the procedures beginning from weighing the compound until obtaining the in vivo data were done under minimal light conditions. Female BALB/c and nude mice were purchased from NCI (Frederick, Md.). Mice were housed and handled in the animal facility of the College of Pharmacy or the Rodent Barrier Facility in the Biomedical Research Center-West at University of Oklahoma Health Science Center (OUHSC). All animal experiments were approved by the OUHSC IACUC.

Synthesis.

CA4,[100] compound 1,[101] compound 2 (L-CA4),[101] CMP-COOH,[53] IY69,[102] and CMP-L-Rh[86] were synthesized as reported previously.

CMP-L-CA4.

To a stirred solution of CMP-COOH (200 mg, 0.28 mmol) and compound 2 (267 mg, 0.55 mmol) in dry DCM (15 mL), a solution of DCC (228 mg, 1.1 mmol) and DMAP (67 mg, 33.7 mmol) in dry DCM (20 mL) was added drop wise. The reaction mixture was then stirred at r.t. for 24 h. The solvent was removed under reduced pressure to give the crude product that was then purified by column chromatography by using ethyl acetate:hexane (6:4) as an eluent to give a reddish purple solid (CMP-L-CA4) (452 mg, 69%). $^1$H NMR (300 MHz, CD$_2$Cl$_2$) δ 0.90 (m, 2H), 1.28 (m, 2H), 1.41 (m, 2H), 1.87 (m, 1H), 3.09 (s, 1H), 3.66 (s, 6H), 3.75 (d, J=6.4 Hz, 6H), 4.22 (d, J=5.2 Hz, 2H), 4.80 (d, J=12.8 Hz, 1H), 4.96 (s, 2H), 6.44 (s, 2H), 6.52 (s, 2H), 6.84 (d, J=8.4 Hz, 1H), 6.97 (s, 1H), 7.09 (d, J=6.2 Hz, 1H), 7.40 (d, J=7.7 Hz, 2H), 7.50 (d, J=12.8 Hz, 1H), 7.54 (br s, 9H), 8.27 (m, 8), 8.72 (m, 4H), 9.74 (m, 4H). HRMS ESI (m/z): Calculated for C$_{73}$H$_{62}$N$_3$O$_9$S$_2$ ([M+H]$^+$): 1188.3849. found: 1188.3875.

Compound 3.

To a solution of CA4 (1.20 g, 3.79 mmol) in acetone (20 mL), anhydrous K$_2$CO$_3$ (1.57 g 11.37 mmol) and 1,3-dibromopropane (0.76 g, 3.79 mmol) were added. The reaction mixture was refluxed in an oil bath for 12 h. After the reaction, the K$_2$CO$_3$ was removed by suction filtration and the solvent was removed under reduced pressure to give the crude product, which was then purified by using column chromatography with ethyl acetate:hexane (3:7) to give a yellow oil (compound 3, 1.39 g, 84%). $^1$H NMR (300 MHz, CDCl$_3$) δ 2.26 (m, 2H), 3.56 (t, J=6.5 Hz, 2H), 3.72 (s, 6H), 3.85 (s, 6H), 3.95 (t, J=5.6 Hz, 2H), 6.49 (d, J=12.0 Hz, 1H), 6.50 (d, J=12.0 Hz, 1H), 6.53 (s, 2H), 6.79 (d, J=7.9 Hz, 1H), 6.87 (s, 2H). HRMS ESI (m/z): Calculated for $C_{21}H_{25}Br_3O_5$ ([M+H]$^+$): 437.0885. found: 437.0964.

Compound 4.

To a solution of n-Boc-piperazine (212 mg, 1.14 mmol) in dry DMF (10 mL), anhydrous K$_2$CO$_3$ (789 mg, 5.71 mmol) and compound 3 (500 mg, 1.14 mmol) were added. The reaction mixture was stirred at room temperature for 8 h. The K$_2$CO$_3$ was removed by suction filtration and the solvent was removed under reduced pressure. The residue was dissolved with water and extracted with ethyl acetate. The combined organic layers were dried over anhydrous Na$_2$SO$_4$, and the solvent was removed by evaporation. The crude product was purified by using column chromatography with ethyl acetate:hexane (8:2) to give a yellow oil (compound 4, 539 mg, 87%). $^1$H NMR (300 MHz, CDCl$_3$) δ 1.45 (s, 9H), 1.91 (m, 2H), 2.46 (s, 4H), 2.56 (t, J=7.3 Hz, 2H), 3.41 (s, 4H), 3.69 (s, 6H), 3.82 (d, J=2.4 Hz, 6H), 3.88 (t, J=6.1 Hz, 2H), 6.43 (d, J=12.3 Hz, 1H), 6.47 (d, J=12.3 Hz, 1H), 6.51 (s, 2H), 6.76 (d, J=7.8 Hz, 1H), 6.84 (s, 2H). HRMS ESI (m/z): Calculated for $C_{30}H_{42}N_2O_7$ ([M+H]$^+$): 543.2992. found: 543.3066.

Compound 5 (NCL-CA4).

Compound 4 (425 mg, 0.78 mmol) was dissolved in dry DCM (6 mL). After TFA (0.06 mL) was added to the solution at 0° C., it was stirred under nitrogen for 1 h. The reaction mixture was then concentrated under vacuum and used directly in the next step without purification.

CMP-NCL-CA4.

It was prepared according to the method described for compound CMP-L-CA4 employing CMP—COOH (70 mg, 0.10 mmol), compound 5 (85 mg, 0.19 mmol), DCC (78 mg, 0.38 mmol) and DMAP (23 mg, 0.19 mmol) to give a reddish purple solid (compound 9, 164 mg, 74%). $^1$H NMR (300 MHz, CDCl3) δ 2.08 (t, J=5.6 Hz, 2H), 2.62 (m, 6H), 3.72 (m, 4H), 3.78 (s, 3H), 3.86 (s, 3H), 3.88 (s, 6H), 4.16 (t, J=6.5 Hz, 2H), 4.98 (s, 2H), 6.54 (d, J=11.8 Hz, 1H), 6.74 (s, 2H), 6.89 (d, J=8.2 Hz, 1H), 6.96 (d, J=7.8 Hz, 1H), 7.06 (d, J=9.8 Hz, 1H), 7.13 (s, 1H), 7.41 (d, J=8.0 Hz, 2H), 7.84 (s, 9H), 8.21 (d, J=8.3 Hz, 2H), 8.26 (s, 6H), 8.71 (m, 4H), 9.72 (m, 4H). HRMS ESI (m/z): Calculated for $C_{71}H_{62}N_4O_7S_2$ ([M+H]$^+$): 1147.4060. found: 1147.4128.

Molecular Modeling.[97]

Docking analysis was performed by using the software package, AutoDock Tools version 1.5.2 revision 2 (Molecular Graphics Laboratory, The Scripps Research Institute) and ChemDraw Ultra (Cambridge Soft Corporation).

Preparing Ligands for Docking:

The energy minimized files were generated for the designed ligands by using the website http://www.molecular-networks.com/online_demos/corina_demo or Chem3D. The AutoTors application of the AutoDock program suite was used to add gasteiger charges, to merge non-polar hydrogens, and to initialize torsions for each ligand.

Preparation of Protein Coordinate Files:

The x-ray structures of tubulin with its native ligand (PDB code 1SA0)[96] were taken from the RSCB protein data bank. There were four chains in 1SA0: Chain A (α 1-tubulin), Chain B (β1-tubulin), Chain C (α 2-tubulin) and Chain D (β 2-tubulin). The β-tubulin subunit (Chain B or D) was extracted. The native ligand and water molecules were removed. The polar hydrogens and Kollman charges were added to the 1SA0 protein coordinate files in preparation for computing grid maps.

Grid Generation:

Atomic affinity grid maps were computed for each atom type in the ligand set, as well as an electrostatics grid map, from the protein models using AutoGrid 4.0 and the standard AutoDock 4.0 force field. The wheels were adjusted so that the grid box covered the entire protein.

Docking:

The GA-LS (Lamrckin genetic algorithm) was chosen to search for the best conformers. During the docking process, the docking parameters were set to Number of GA Runs 50, Population Size of 150, Maximum Number of evaluation 2500000, Maximum Number of generations 27000, Rate of Gene Mutation 0.02, and Rate of Crossover 0.8 for each compound. The parameters were set by using the software AutoDock Tools available at http://mgltools.scripps.edu/downloads, which is made to work with AutoDock 4.0. The calculation of the autogrid and autodock was performed on a Macintosh operating system with the following system properties: Intel® Core' 2 Duo CPU 2.0 GHz and 2.0 GB 667 MHz DDR2 of SDRAM.

Docking accuracy was assessed by redocking ligands from 1SA0 co-crystallized PDB complexes starting from conformationally optimized ligand geometries. After a co-crystallized ligand was docked, RMSD for the top-ranked pose was less than 0.5 Å.

Analysis of Docking Results:

At the end of the docking run, AutoDock outputs the result that is the lowest energy conformation of the ligand, which it found during that run. This conformation is a combination of translation, quaternion and torsional angles, and is characterized by intermolecular energy, internal energy and torsional energy. The first two of these combined give the 'docking energy' while the first and third give 'binding energy'. AutoDock 4.0 also breaks down the total energy into Vander Waals (vdW) energy and electrostatic energy for each atom. We used the overall lowest binding energy output by AutoDock 4.0 and the inhibitory concentration (Ki), as the criteria for ranking. Therefore, on the basis of the clustering histogram output from the AutoDock program, the lowest energy conformation of each cluster was selected. The selected conformations were grouped based on their binding sites. For each binding site, multiple binding modes were considered. All of the conformations that were outside the active site were disregarded.

Tubulin Polymerization Assay.

The fluorescence-based tubulin polymerization was determined by using a kit supplied by Cytoskeleton, Inc. (cat #=BK011P). Its basic principle is that the fluorescence reporter increases as it is incorporated into microtubules during the course of polymerization. The assay was performed following the experimental procedure as described in version 2.1 of the tubulin polymerization assay kit manual. Briefly, the test drug (final concentration=3 μM) was added to a mixture of tubulin and GTP in a buffer solution, and the reaction mixture was incubated at 37° C. Fluorescence was monitored (excitation=360 nm and emission=450 nm) by using a fluorescence plate reader (SpectraMax Gemini EM, Molecular device). Paclitaxel and CA4 were included in the assay as positive controls in addition to the negative control (vehicle only).

Dark Toxicity and Phototoxicity.

The cytotoxicities of CMP-L-CA4 and CMP-NCL-CA4 were determined with or without irradiation. MCF-7 cells were maintained in minimum essential medium (α-MEM)

supplemented with 10% bovine growth serum, 2 mM L-glutamine, 50 units/mL penicillin G, 50 µg/mL streptomycin and 1.0 µg/mL fungizone. MCF-7 cells (5,000 cells/well) were seeded on 96-well plates in the medium and then incubated for 24 h at 37° C. in 5% $CO_2$. Stock solutions (2 mM) were prepared in DMSO. The stocks were further diluted with medium to get necessary final concentrations. The diluted solution (10 µL) was then added to each well (190 µL). The plates were incubated for 24 h and then removed from the incubator. For the phototoxicity study: The plate without a cover was placed on an orbital shaker (Lab-line, Barnstead International) and irradiated by using a diode laser (690 nm, 5.6 mW/cm$^2$) for 30 min. To ensure uniformity of the light during the irradiation, each plate was shaken gently on an orbital shaker. For the dark toxicity study: Plates were kept in the dark for 30 min, and then returned to the incubator. Cell viability was determined after 3 days by using the MTT assay. Briefly, a 10 µL solution of MTT (10 mg in 1 mL PBS buffer) was added to each well and the plate was incubated for 4 h. Then, the MTT solution was removed and the cells were dissolved in 200 µL of DMSO and the absorbance within each well was measured at 570 nm with background subtraction at 650 nm. The cell viability was then quantified by measuring the absorbance of the treated wells compared to that of the untreated wells (controls) and expressed as a percentage.

Bystander Effect by CMP-L-CA4.

Colon 26 cells were seeded at 5,000 cells/ml/well in 24-well plates and then incubated for 24 h. Stock solutions (2 mM in DMSO) were diluted with medium. The diluted solutions (25 µL) were added to the wells (1 mL) to get the appropriate final concentrations [CMP-L-CA4 (50 nM) and IY69 (5 µM)]. After 24 h incubation, the plates were irradiated from the bottom with 690 nm diode laser at 11 mW/cm$^2$ for 15 min. While irradiating, half of each well was blocked with a black masking tape (THORLABS, Cat# T743-1.0) to protect cells on the other half of each well. The irradiated plates were incubated for an additional 48 h. Then a Calcein AM live cell staining assay was performed. Briefly, the cells were washed once with the Calcein AM wash buffer (1 mL) and then fresh wash buffer (250 mL) and the working reagent (250 mL) were added to the wells. The cells were incubated for 30 min. Fluorescent images were obtained with an Olympus IX51 inverted microscope with green fluorescence channel to visualize live cells. All images were taken at 10+ magnifications.

In Vivo Optical Imaging Using the FRET Probe.

The injection solution of CMP-L-Rh was prepared by solubilizing it in Tween 80 (100 µL) using a mortar and pestle to get a viscous paste. The paste was left for 4 h at room temperature. Then, the viscous paste was stirred well and extracted into 5% dextrose solution. The solution was filtered through a 0.2 µm sterile syringe filter. The concentration of the solution was determined by diluting the formulation in DMSO and the absorbance was measured by the absorbance of CMP group. The concentration was calculated from the extinction coefficient of PS-L-Rh at 438 nm in DMSO ($\epsilon$=287,000 M$^{-1}$cm$^{-1}$) using the Beer-Lambert law.

One four-week-old female athymic nu/nu mouse (~20 g, Charles River Laboratories, Inc.) was used to investigate the cleavage of CMP-L-Rh by irradiation. The mouse was imaged by using IVIS Imaging system (Caliper Life Sciences), which consists of a cryogenically cooled imaging system coupled to a data acquisition computer running Living Image® software. The mouse was irradiated with a 690 nm diode laser at 500 mW/cm$^2$ at the neck region 1.5 h post-injection of the CMP-L-Rh (24 µmole/kg, i.p.). Fluorescence images were taken after irradiation for 0, 10, 20, and 30 min. Before taking the images, the mouse was anesthetized in an acrylic chamber with 2.5% isoflurane/air mixture. The following parameters were used to acquire images with Living Imaging® software: fluorescence mode, exposure time: 5 sec, binning: medium, F/Stop: 2, excitation: 535 nm and emission: 580 nm. During post processing, image counts were adjusted to 3×10$^4$ as minimum and 6.5×10$^4$ a.u. as maximum color scale.

Antitumor Efficacy Study.

Four- to six-week-old BALB/c mice (18-20 g, Charles River Laboratories, Inc.) were used for the murine tumor model. The mice were implanted s.c. with 2×10$^6$ colon 26 cells in PBS (100 µL) on the lower back-neck region. Tumor growth was monitored with digital caliper. Two dimensions l and w (l: the longest axis of tumor and w: the axis perpendicular to l) were used to calculate tumor volume (lw$^2$/2). Mice with a tumor of the diameter 3-5 mm were used for the experiments.

Stock solutions in DMSO (4 or 8 mM) and further dilutions in 1% Tween 80 and 5% dextrose solution to achieve final doses were as follows: CMP-L-CA4; 4 mM→2 or 4 µmole/kg, CMP-NCL-CA4+CA4; 4 mM→2 µmole/kg, CMP-L-CA4+CA4; 8 mM each→4 µmole/kg. Samples were filtered using 0.2 µm sterile syringe filter. To each mouse, 200 µL of sample was injected via i.p. once a day on day 0, 1, and 2. Then, 1 h 30 min later mice were anesthetized with ketamine 80 mgkg$^{-1}$ and xylazine 6 mgkg$^{-1}$, i.p. injection. Tumors were irradiated with a 690 nm diode laser at 200 mW/cm$^2$ for 30 min (360 J/cm$^2$). Tumor size was measured with the digital caliper every day after the treatment.

Relative Rates of Photooxidation of the Linker in CMP-L-CA4 with ROS Quenchers.

Figure 40:
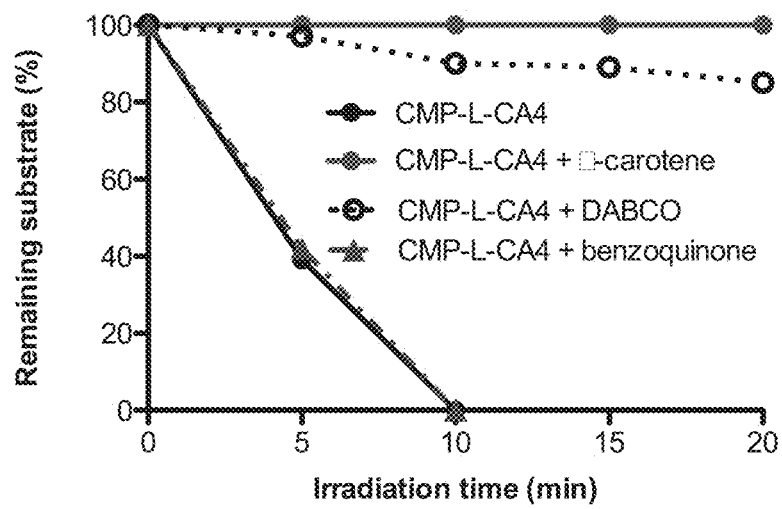
FIG. 40 graphically represents time-dependent oxidation of aminoacrylate linker of CMP-L-CA4 with or without ROS scavenger.

To confirm that the cleavage of the aminoacrylate linker was mediated by SO, CMP-L-CA4 was irradiated in the presence of an SO quencher (DABCO or β-carotene) or a superoxide quencher (1,4-benzoquinone). CMP-L-CA4 (1.2 µmol) and a SO quencher (or superoxide quencher, 1.2µmol) were dissolved in CDCl$_3$ (0.5 mL) in an NMR tube. The reaction mixture was irradiated by using diode laser (690 nm, 10 mW/cm$^2$). The oxidation of the olefin with SO was monitored every 5 min by the decrease of the olefinic peaks of the aminoacrylate in $^1$H-NMR It was shown that DABCO and β-carotene dramatically delayed the oxidation of aminoacrylate (FIG. 40). However, benzoquinone did not have any effect on the oxidation of the aminoacrylate linker. These results support the assumption that the cleavage of the aminoacrylate linker is mediated by SO and not a superoxide radical.

Stability of CMP-L-CA4 with Low Intensity Light or in Dark Condition.

Figure 41:
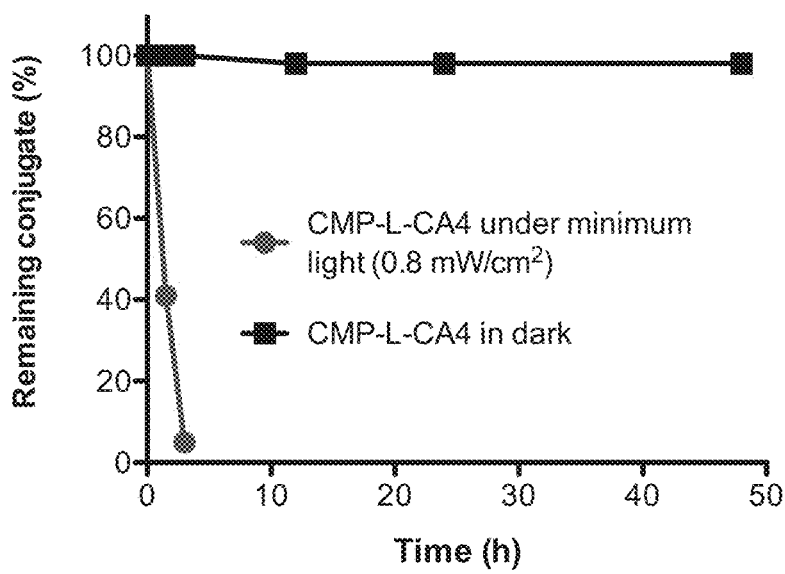
FIG. 41 graphically depicts the stability of CMP-L-CA4 (under light/in dark).

All the experiments with the conjugates were carried out under minimal light (turning off the room light). The stability of CMP-L-CA4 was examine under two conditions, low intensity light (office fluorescent lamp) and minimal light (turning off the room light) by comparing the cleavage of the linker CMP-L-CA4 under these two conditions. As shown in FIG. 41, CMP-L-CA4 kept under dark was very stable even after 48 hrs while most of CMP-L-CA4 exposed to low intensity fluorescent light was cleaved within 3 hrs.

Figure 42:
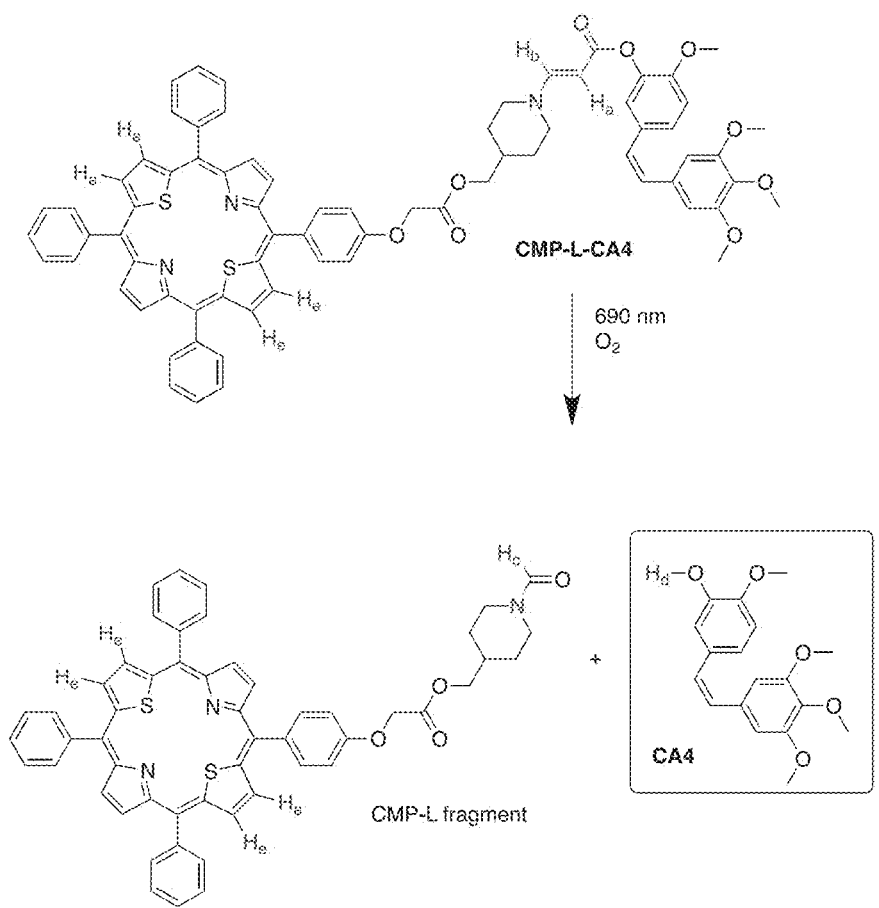
FIG. 42 schematically represents structures of CMP-L-CA4 and its photocleavage products (CMP-L fragment and CA4).

Detection of Released CA4 from CMP-L-CA4 after the Irradiation. To confirm the identity and quantity of the released CA4 from CMP-L-CA4 (FIG. 42), a number of analytics methods were used: TLC, GC-MS, and $^1$H-NMR. In a NMR tube, CMP-L-CA4 (3 mg) was dissolved in CDCl$_3$ (0.5 mL) and the solution was irradiated for 15 min using a diode laser (690 nm, 10 mW/cm$^2$). On TLC, after 15 min irradiation a CMP-L-CA4 spot disappeared completely (not visible) of the irradiation and two new spots appeared, one of which was colorless and at the same position with the CA4 standard. The other polar compound showed a spot with a typical porphyrin color (light yellowish). The colorless spot was extracted and analyzed with GC-MS. The compounds extracted from the TLC showed same retention time (~18.35 min) and mass (316 m/z) with those of CA4 standard sample. Thus, it was concluded that the released product in the TLC spot was CA4.

Next, the conversion of CMP-L-CA4 to CA4 after the irradiation was quantified using signature peaks in $^1$H-NMR spectra. In the $^1$H-NMR spectra, peaks from proton Hb and proton Hc did not show any overlap with the other peaks. The peak from proton Ha partially overlapped with the peak from the proton Hd of released CA4. The peak of the porphyrin protons He was used as an internal standard, which was unchanged under this irradiation condition. The NMR data demonstrated the near quantitative conversion from CMP-L-CA4 to the products (CMP-L fragment and CA4) during the irradiation.

In addition, also obtained was two supporting spectral data for the other cleaved product. In the $^1$H-NMR spectra, a singlet peak near 8 ppm appeared, corresponding to Hd. The exact same mass was also found for the CMP-L fragment from the extracted sample from the lower spot of the TLC.

Thus, in accordance with the presently disclosed and claimed inventive concept(s), there has been provided improved compositions comprising linkers that provide controlled drug delivery/release systems, as well as methods for producing and using same. Although the presently claimed and disclosed inventive concept(s) has been described in conjunction with the specific drawings and language set forth above, it is evident that many alternatives, modifications and variations will be apparent to those skilled in the art. Accordingly, it is intended to embrace all such alternatives, modifications and variations that fall within the spirit and broad scope of the inventive concept(s).

REFERENCES

The following references, to the extent that they provide exemplary procedural or other details supplementary to those set forth herein, are specifically incorporated herein by reference.

1. Dougherty, T. J.; Gomer, C. J.; Henderson, B. W.; Jori, G.; Kessel, D.; Korbelik, M.; Moan, J.; Peng, Q. *J. Natl. Cancer Inst.* 1998, 90, 889.
2. Allison, R. R.; Mota, H. C.; Sibata, C. H. *Photodiagn. Photodyn. Ther.* 2004, 1, 263.
3. Shum, P.; Kim, J. M.; Thompson, D. H. *Adv. Drug Delivery Rev.* 2001, 53, 273.
4. Zhang, Z. Y.; Shum, P.; Yates, M.; Messersmith, P. B.; Thompson, D. H. *Bioconjugate Chem.* 2002, 13, 640.
5. Ruebner, A.; Yang, Z.; Leung, D.; Breslow, R. *Proc. Nat. Acad. Sci. U.S.A* 1999, 96, 14692.
6. Baugh, S. D.; Yang, Z.; Leung, D. K.; Wilson, D. M.; Breslow, R. *J. Am. Chem. Soc.* 2001, 123, 12488.
7. Jiang, M. Y.; Dolphin, D. *J. Am. Chem. Soc.* 2008, 130, 4236.
8. Goeldner, M.; Richard, G. In *Dynamic studies in biology: phototriggers, photoswitches and caged biomolecules*: Wiley-VCH, 2005.
9. Wilson, B. C. In *Photosensitizing compounds: their chemistry, biology, and clinical use*; Wiley: Chichester, 1989, pp 60.
10. Faler, G. R., Ph.D. thesis, In *I. A Study of the Kinetics of the 1,2-Cycloaddition of Singlet Oxygen to Vinyl Ethers. II. An Investigation of the Reaction of Singlet Oxygen with Adamantylideneadamantane*, Wayne State University, 1977.
11. Frimer, A. A.; Bartlett, P. D.; Boschung, A. F.; Jewett, J. G. *J. Am. Chem. Soc.* 1977, 99, 7977.
12. Jefford, C. W.; Kohmoto, S. *Helv. Chim. Acta* 1982, 65, 133.
13. Gollnick, K.; Knutzen-Mies, K. *J. Org. Chem.* 1991, 56, 4017.
14. Machado, A. E. d. H.; Andrade, M. L. d.; Severino, D. *J. Photochem. Photobiol. A* 1995, 91, 179.
15. Matsumoto, M.; Kobayashi, H.; Matsubara, J.; Watanabe, N.; Yamashita, S.; Oguma, D.; Kitano, Y.; Ikawa, H. *Tetrahedron Lett.* 1996, 37, 397.
16. Suga, K.; Ohkubo, K.; Fukuzumi, S. *J. Phys. Chem. A* 2003, 107, 4339.
17. Gollnick, K. *Adv. Photochem.* 1968, 6, 1.
18. Kearns, D. R. *Chem. Rev.* 1971, 71, 395.
19. Kearns, D. R. *J. Am. Chem. Soc.* 1969, 91, 6554.
20. Rio, G.; Berthelot, J. *Bull. Soc. Chim. Fr.* 1969, 3609.
21. Bartlett, P. D.; Mendenhall, G. D.; Schaap, A. P. *Ann. N. Y. Acad. Sci.* 1970, 171, 79.
22. Sales, F.; Serratosa, F. *Tetrahedron Lett.* 1979, 20, 3329.
23. Wamser, C. C.; Herring, J. W. *J. Org. Chem.* 1976, 41, 1476.
24. Banfi, S.; Caruso, E.; Buccafurni, L.; Murano, R.; Monti, E.; Gariboldi, M.; Papa, E.; Gramatica, P. *J. Med. Chem.* 2006, 49, 3293.
25. Yang, J.; Bauld, N. L. *J. Org. Chem.* 1999, 64, 9251.
26. Bauld, N. L. and J. Yang (2000) Intramolecular site selectivity in cation radical Diels-Alder cycloadditions of difunctional and trifunctional dienophiles. *J. Phy. Org. Chem.* 13, 518-522.
27. Aoshima, S. and S. Kanaoka (2008) Synthesis of stimuli-responsive polymers by living polymerization: poly(N-Isopropylacrylamide) and poly(Vinyl Ether)s. *Adv. Pol. Sci.* 210, 169-208.
28. Davies, H. M. L. and B. Hu (1992) Highly stereoselective [3+2] annulations by cyclopropanation of vinyl ethers with rhodium(II)-stabilized vinylcarbenoids followed by a formally forbidden 1,3-sigmatropic rearrangement. *J. Org. Chem.* 57, 3186-3190.
29. Jiao, P., D. Nakashima and H. Yamamoto (2008) Enantioselective 1,3-dipolar cycloaddition of nitrones with ethyl vinyl ether: The difference between Brønsted and Lewis acid catalysis. *Angew. Chem. Int. Ed. Engl.* 47, 2411-2413.
30. Schaap, A. P. Z., K. A. In singlet oxygen; (1979) *Singlet Oxygen*. Academic Press, New York.
31. Frimer, A. A. (1979) Reaction of singlet oxygen with olefins—Question of mechanism. *Chem. Rev.* 79, 359-387.
32. Foote, C. S. and R. W. Denny (1971) Chemistry of singlet oxygen 0.12. electronic effects on rate and products of reaction with olefins. *J. Am. Chem. Soc.* 93, 5162-5167.
33. Clennan, E. L. and K. Nagraba (1988) Additions of singlet oxygen to alkoxy-substituted dienes—the mechanism of the singlet oxygen 1,2-cycloaddition reaction. *J. Am. Chem. Soc.* 110, 4312-4318.
34. Bartlett, P. D. (1976) 4-Membered rings and reaction-mechanisms. *Chem. Soc. Rev.* 5, 149-163.

35. Murthy, R. S., M. Bio and Y. J. You (2009) Low energy light-triggered oxidative cleavage of olefins. *Tetrahedron Lett.* 50, 1041-1044.
36. Kabir, M. S., M. L. Van Linn, A. Monte and J. M. Cook (2008) Stereo- and regiospecific cu-catalyzed cross-coupling reaction of vinyl iodides and thiols: a very mild and general route for the synthesis of vinyl sulfides. *Org. Lett.* 10, 3363-3366.
37. Baganz, H. (1959) Chemistry of di-dlpha-halogeno ethers. *Angew. Chem. Int. Ed. Engl.* 71, 366-371.
38. Kalabina, A. V., Kolmakov. Ef, T. I. Bychkova, Maksyuti. Yk, Denisevi. Ea and G. I. Smolina (1965) Substituted aryl vinyl and aryl ethyl ethers 0.1. Reaction of benzenesulfenyl chloride with aryl vinyl ethers. *J. Gen. Chem. Ussr.* 35, 979-982.
39. Rozinov, V. G., Mikhnevi. Vv and E. F. Grechkin (1970) Phosphorylation of trisubstituted olefins with phosphorus pentachloride. *J. Gen. Chem. Ussr.* 40, 935.
40. Bychkova, T. I., M. A. Vasileva, L. B. Krivdin and A. V. Kalabina (1984) Reaction of (2-phenyloxyethenyl)alkylsulfones or arylsulfones with sodium diethyldithiocarbamate. *Zh. Org. Khim.* 20, 2114-2118.
41. Bychkova, T. I., M. A. Vasileva, A. V. Kalabina, T. I. Rozova and G. V. Ratovskii (1984) Synthesis, properties and spectral studies of 1-phenylsulfinyl-2-aryloxyethenes. *Zh. Org. Khim.* 20, 524-529.
42. Baganz, H. and P. Klinke (1955) Uber 1.2-Diphenoxyathen. *Chem. Ber.* 88, 1647-1653.
43. M. Zamadar, G. Ghosh, A. Mahendran, M. Minnis, B. I. Kruft, A. Ghogare, D. Aebisher and A. Greer. (2011) Photosensitizer drug delivery via an optical fiber. *J. Am. Chem. Soc.* 133, 7882-7891.
44. Mahendran, A., Y. Kopkalli, G. Ghosh, A. Ghogare, M. Minnis, B. I. Kruft, M. Zamadar, D. Aebisher, L. Davenport and A. Greer (2011) A Hand-held fiber-optic implement for the site-specific delivery of photosensitizer and singlet oxygen. *Photochem. Photobiol.* 87, 1330-1337.
45. Kaberdin, R. V. and V. I. Potkin (1994) Trichloroethylene in organic-synthesis. *Usp. Khiz.* 63, 673-692.
46. Moyano, A., F. Charbonnier and A. E. Greene (1987) A simple preparation of chiral acetylenic ethers. *J. Org. Chem.* 52, 2919-2922.
47. Dudley, G. B., K. S. Takaki, D. D. Cha and R. L. Danheiser (2000) Total synthesis of (−)-ascochlorin via a cyclobutenone-based benzannulation strategy. *Org. Lett.* 2, 3407-3410.
48. Lipshutz, B. H. and E. L. Ellsworth (1990) Hydrozirconation-transmetalation—a mild, direct route to higher-order vinylic cuprates from monosubstituted acetylenes. *J. Am. Chem. Soc.* 112, 7440-7441.
49. Dussault, P. H., Q. Han, D. G. Sloss and D. J. Symonsbergen (1999) Photooxygenation of chiral dienol ethers: asymmetric synthesis of alkoxydioxines. *Tetrahedron* 55, 11437-11454.
50. Taillefer, M., A. Ouali, B. Renard and J. F. Spindler (2006) Mild copper-catalyzed vinylation reactions of azoles and phenols with vinyl bromides. *Chemistry* 12, 5301-5313.
51. Cook, J. M., M. S. Kabir, M. Lorenz and O. A. Namjoshi (2010) First application of an efficient and versatile ligand for copper-catalyzed cross-coupling reactions of vinyl halides with N-heterocycles and phenols. *Org. Lett.* 12, 464-467.
52. Kaddouri, H., V. Vicente, A. Ouali, F. Ouazzani and M. Taillefer (2009) Copper-catalyzed arylation of nucleophiles by using butadienylphosphines as ligands: mechanistic insight. *Angew. Chem. Int. Ed. Engl.* 48, 333-336.
53. You, Y., S. L. Gibson, R. Hilf, S. R. Davies, A. R. Oseroff, I. Roy, T. Y. Ohulchanskyy, E. J. Bergey and M. R. Detty (2003) Water soluble, core-modified porphyrins. 3. Synthesis, photophysical properties, and in vitro studies of photosensitization, uptake, and localization with carboxylic acid-substituted derivatives. *J. Med. Chem.* 46, 3734-3747.
54. Cermola, F., A. Guaragna, M. R. lesce, G. Palumbo, R. Purcaro, M. Rubino and A. Tuzi (2007) New insight into the reaction of singlet oxygen with sulfur-containing cyclic alkenes: dye-sensitized photooxigenation of 5,6-dihyro-1,4-dithiins. *J. Org. Chem.* 72, 10075-10080.
55. Adam, W. and J-. C. Liu (1972) Photooxygenation (singlet oxygen) of tetrahtioethylenes. *J. Am. Chem. Soc.* 94, 1206-1209.
56. Clennan, E. L. and A. Pace (2005) Advances in singlet oxygen chemistry. *Tetrahedron* 61, 6665-6691.
57. M. Meinhardt, R. Krebs, A. Anders, U. Heinrich and H. Tronnier, *J. Biom. Opt.*, 2008, 13, 044030.
58. P. Juzenas, A. Juzeniene, O. Kaalhus, V. Iani and J. Moan, *Photochem. Photobio. Sci.*, 2002, 1, 745-748.
59. C. A. L. Filgueiras, C. Celso, G. H. Coelho and B. F. G. Johnson, *Inorg. Nucl. Chem. Lett.*, 1981, 17, 283-285.
60. A. B. Lowe, C. E. Hoyle and C. N. Bowman, *J. Mat. Chem.*, 2010, 20, 4745-4750.
61. Y. Ichinose, K. Wakamatsu, K. Nozaki, J.-L. Birbaum, K. Oshima and K. Utimoto, *Chem. Lett.*, 1987, 16, 1647-1650.
62. A. R. A. S. Deshmukh, G. D. Joshi, K. G. Gore and G. H. Kulkarni, *Synthetic Commun.*, 1990, 20, 2259-2265.
63. E. J. Ngen, P. Rajaputra and Y. You, *Bioorg. Med. Chem.*, 2009, 17, 6631-6640.
64. *Handbook of Photochemistry*, 3$^{rd}$ ed. M. Montalti, A. Credi, L. Prodi, M. T. Gandolfi, Taylor & Francis Group, Boca Raton, Fla., 2006.
65. *Modern Molecular Photochemistry*, ed. N. J. Turro, University Science Books, Sausalito, C A, 1991.
66. Bao, C.; Jin, M.; Li, B.; Xu, Y.; Jina, J.; Zhu, L. Long conjugated 2-nitrobenzyl derivative caged anticancer prodrugs with visible light regulated release: preparation and functionalizations. *Org. Biomol. Chem.* 2012, 10, 5238-5244
67. Kratz, F.; Warnecke, A.; Scheuermann, K.; Stockmar, C.; Schwab, J.; Lazar, P.; Druckes, P.; Esser, N.; Drevs, J.; Rognan, D.; Bissantz, C.; Hinderling, C.; Folkers, G.; Fichtner, I.; Unger, C. Probing the cysteine-34 position of endognous serum albumin with thiol-binding doxorubicin derivatives. Improved efficacy of an acid-sensitive doxorubicin derivative with specific albumin-binding properties compared to that of the parent compound. *J. Med. Chem.* 2002, 45, 5523-5533.
68. Snyder, J. W.; Greco, W. R.; Bellnier, D. A.; Vaughan, L.; Henderson, B. W. Photodynamic therapy: A means to enhanced drug delivery to tumors. *Cancer Res.* 2003. 63. 8126-8131.
69. Ellis, G. A.; McGrath, N. A.; Palte, M. J.; Raines, R. T. Ribonuclease-activated cancer prodrug. *ACS Med. Chem. Lett.* 2012, 3, 268-272.
70. Rooseboom, M.; Commandeur, J. N.; Vermeulen, N. P. Enzyme-catalyzed activation of anticancer prodrugs. *Pharmacol. Rev.* 2004, 56, 53-102.
71. Rai, P.; Mallidi, S.; Zheng, X.; Rahmanzadeh, R.; Mir, Y.; Elrington, S.; Khurshid, A.; Hasan, T. Development and applications of photo-triggered theranosticagents. *Adv. Drug Deliv. Rev.* 2010, 62, 1094.

72. Alvarez-Lorenzo, C.; Bromberg, L.; Concheiro, A. Light-sensitive intelligent drug delivery dystems. *Photochem. Photobiol.* 2009, 85, 848-860.

73. Katz, J. S.; Burdick, Light-responsive biomaterials: development and applications. *Macromol. Biosci.* 2010, 10, 339-348.

74. Yu, H.; Li, J.; Wu, D.; Qiu, Z.; Zhang, Y. Chemistry and biological applications of photo-labile organic molecules. *Chem. Soc. Rev.* 2010, 39, 464-473.

75. Mayer, G.; Heckel, A. Biologically active molecules with a "light switch". *Angew. Chem. Int. Ed. Engl.* 2006, 45, 4900-4921.

76. Lovell, J. F.; Liu, T. W.; Chen, J.; Zheng, G. Activatable photosensitizers for imaging and therapy. *Chem. Rev.* 2010, 110, 2839-2857.

77. Kobayashi, H.; Ogawa, M.; Alford, R.; Choyke, P. L. Urano, Y. New strategies for fluorescent probe design in medical diagnostic imaging. *Chem. Rev.* 2010, 110, 2620-2640.

78. Takemoto, K.; Matsuda, T.; McDougall, M.; Kaubert, D. H.; Hasegawa, A.; Los, G. V.; Wood, K. V.; Miyawaki, A.; Nagai, T. Chromophore-assisted light inactivation of halo tag fusion proteins labeled with eosin in living cells. *ACS Chem. Biol.* 2011, 6, 401-406.

79. Ramesh, M.; Ahlawat, P.; Srinivas, N. R. Irinotecan and its active metabolite, SN-38: review of bioanalytical methods and recent update from clinical pharmacology perspectives *Biomed. Chromatogr.* 2010, 24, 104-123.

80. Nagaiah, G.; Remick, S. C. Combretastatin A4 phosphate: a novel vascular disrupting agent. *Future Oncology* 2010, 6, 1219-1228.

81. Neises, B.; Steglich, W. Organic Syntheses; Wiley & Sons: New York, Esterification of carboxylic acids with dicyclohexylcarbodomide/4-dimenthlaminopyridine:tert-butyl ethyl fumarate. 1990; Vol. 7, pp 93.

82. Skovsen, E.; Snyder, J. W.; Lambert, J. D.; Ogilby, P. R. Lifetime and diffusion of singlet oxygen in a cell. *J. Phys. Chem. B* 2005, 109, 8570-8573.

83. Niedre, M.; Patterson, M. S.; Wilson, B. C. Direct near-infrared luminescence detection of singlet oxygen generated by photodynamic therapy in cells in vitro and tissues in vivo. *Photochem. Photobiol.* 2002, 75, 382-391.

84. Moan, J. On the diffusion length of singlet oxygen in cells and tissues. *J. Photochem. Photobiol. B*: Biol. 1990, 6, 343-347.

85. Neises, B.; Steglich, W. *Organic Synthesis.* Wiley & Sons: New York, 1983; Vol. 7.

86. Bio, M.; Nkepang, G.; You, Y. Click and photo-unclick chemistry of aminoacrylate for visible light-triggered drug release. *Chem Commun (Camb)* 2012, 48, 6517-9.

87. Young, R. H.; Wehrly, K.; Martin, R. L. Solvent effects in dye-sensitized photooxidation reactions. *J Am Chem Soc* 1971, 93, 5774-5779.

88. Shiozaki, H.; Nakazumi, H.; Takamura, Y.; Kitao, T. Mechanisms and rate constants for the quenching of singlet oxygen by nickel-complexes. *Bull Chem Soc Jpn* 1990, 63, 2653-2658.

89. Mosmann, T. Rapid colorimetric assay for cellular growth and survival: application to proliferation and cytotoxicity assays. *J Immunol Methods* 1983, 65, 55-63.

90. Pettit, G. R.; Cragg, G. M.; Singh, S. B. Antineoplastic agents, 122. Constituents of *Combretum* caffrum. *J. Nat. Prod.* 1987, 50, 386-391.

91. Pettit, G. R.; Singh, S. B.; Boyd, M. R.; Hamel, E.; Pettit, R. K.; Schmidt, J. M.; Hogan, F. Antineoplastic agents. 291. Isolation and synthesis of combretastatins A-4, A-5, and A-6(1a). *J. Med. Chem.* 1995, 38, 1666-1672.

92. Dark, G. G.; Hill, S. A.; Prise, V. E.; Tozer, G. M.; Pettit, G. R.; Chaplin, D. J. Combretastatin A-4, an agent that displays potent and selective toxicity toward tumor vasculature. *Cancer Res.* 1997, 57, 1829-1834.

93. Pettit, G. R.; Rhodes, M. R.; Herald, D. L.; Hamel, E.; Schmidt, J. M.; Pettit, R. K. Antineoplastic agents. 445. Synthesis and evaluation of structural modifications of (Z)- and (E)-combretastatin A-41. *J. Med. Chem.* 2005, 48, 4087-4099.

94. Kong, Y.; Grembecka, J.; Edler, M. C.; Hamel, E.; Mooberry, S. L.; Sabat, M.; Rieger, J.; Brown, M. L. Structure-based discovery of a boronic acid bioisostere of combretastatin A-4. *Chem. Biol.* 2005, 12, 1007-1014.

95. Jin, Y.; Qi, P.; Wang, Z.; Shen, Q.; Wang, J.; Zhang, W.; Song, H. 3D-QSAR Study of Combretastatin A-4 Analogs Based on Molecular Docking. *Molecules* 2011, 16, 6684-6700.

96. Ravelli, R. B.; Gigant, B.; Curmi, P. A.; Jourdain, I.; Lachkar, S.; Sobel, A.; Knossow, M. Insight into tubulin regulation from a complex with colchicine and a stathmin-like domain. *Nature* 2004, 428, 198-202.

97. Rosenfeld, R. J.; Goodsell, D. S.; Musah, R. A.; Morris, G. M.; Goodin, D. B.; Olson, A. J. Automated docking of ligands to an artificial active site: augmenting crystallographic analysis with computer modeling. *J. Comput. Aided Mol. Des.* 2003, 17, 525-536.

98. You, Y.; Gibson, S. L.; Detty, M. R. Phototoxicity of a core-modified porphyrin and induction of apoptosis. *J Photochem. Photobiol. B* 2006, 85, 155-162.

99. Ohsumi, K.; Nakagawa, R.; Fukuda, Y.; Hatanaka, T.; Morinaga, Y.; Nihei, Y.; Ohishi, K.; Suga, Y.; Akiyama, Y.; Tsuji, T. Novel combretastatin analogues effective against murine solid tumors: design and structure-activity relationships. *J. Med. Chem.* 1998, 41, 3022-3032.

100. Gaukroger, K.; Hadfield, J. A.; Hepworth, L. A.; Lawrence, N. J.; McGown, A. T. Novel syntheses of cis and trans isomers of combretastatin A-4. *J. Org. Chem.* 2001, 66, 8135-8138.

101. Hossion, A. M. L.; Bio, M.; Nkepang, G.; Awuah, S. G.; You, Y. Visible Light Controlled Release of Anticancer Drug through Double Activation of Prodrug. *ACS Med. Chem. Lett.* 2013, 4, 124-127.

102. You, Y.; Gibson, S. L.; Hilf, R.; Ohulchanskyy, T. Y.; Detty, M. R. Core-modified porphyrins. Part 4: Steric effects on photophysical and biological properties in vitro. *Bioorg. Med. Chem.* 2005, 13, 2235-2251.

103. Kamal, A.; Mallareddy, A.; Suresh, P.; Shaik T. B.; Nayak, L.; Kishor, C.; Shetti, R. V.C.R.N.C.; Rao, S.; Tamboli, J.; Ramakrishna, S.; Addlagatta, A. Synthesis of chalcone-amidobenzothiazole conjugates as antimitotic and apoptotic inducing agents, *Bioorg. Med. Chem.* 2012, 20, 3480-3492.

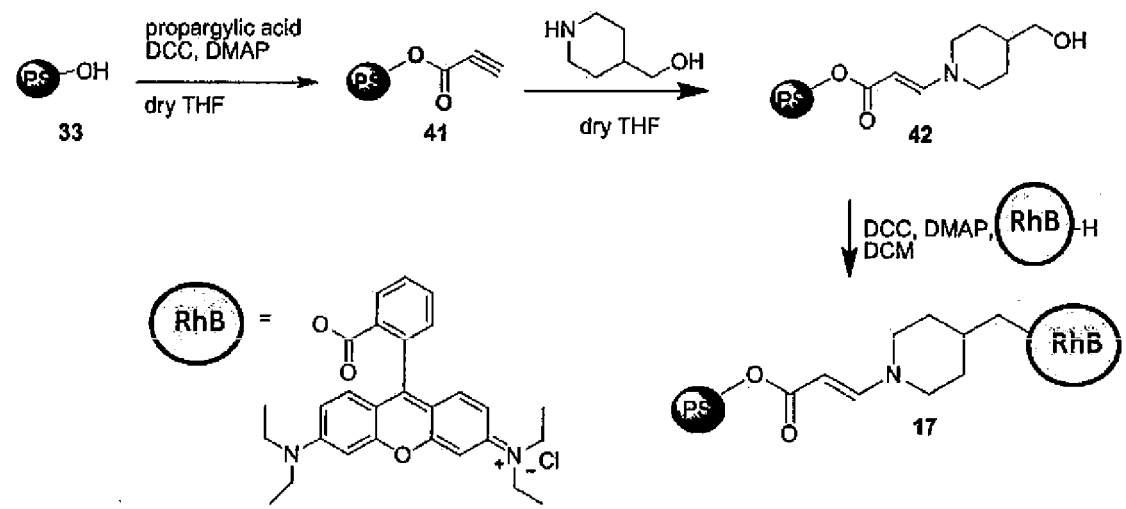

What is claimed is:

1. An activatable composition, comprising:
    at least one functional moiety;
    at least one singlet oxygen-labile linker selected from the group consisting of aminoacrylate, aminoacrylthioate, and aminoacrylamide, the at least one singlet oxygen-labile linker linked to the at least one functional moiety, wherein the at least one functional moiety is inactive until the at least one singlet oxygen-labile linker is cleaved by singlet oxygen, whereby the at least one functional moiety becomes activated; and
    a sensitizer, which when exposed to an activator results in generation of singlet oxygen by the sensitizer.

2. The activatable composition of claim 1, further defined as comprising at least one of a prodrug, a nano-carrier, and a micro-carrier in which the at least one functional moiety is encapsulated, and wherein the at least one singlet oxygen-labile linker is incorporated into a portion of the structure of the at least one prodrug, nano-carrier, or micro-carrier.

3. The activatable composition of claim 2, wherein the nano-carrier is selected from the group consisting of liposomes, polymers, nanospheres, nanocapsules, micelles, solid lipid nanoparticles, and combinations thereof.

4. The activatable composition of claim 2, further defined as being in the form of a dendrimer.

5. The activatable composition of claim 1, wherein the sensitizer is a photosensitizer selected from the group consisting of porphyrin, phthalocyanines, boron-dipyrromethene (BODIPY) or aza-BODIPY-type photosensitizers, chlorins, bacteriochlorins, non-porphyrin-based photosensitizers, and combinations thereof.

6. The activatable composition of claim 1, further comprising a spacer between the at least one singlet oxygen-labile linker and the at least one functional moiety.

7. The activatable composition of claim 6, wherein the spacer is selected from the group consisting of piperidin-4-ylmethanol, pyrrolidine-2-carboxylic acid, pyrrolidine-3-carboxylic acid, piperidin-4-ylmethyl-2-bromoacetate, 1-(3-bromoporpyl) piperazine, and combinations thereof.

8. The activatable composition of claim 1, further comprising at least one targeting/delivery moiety linked to the at least one functional moiety.

9. The activatable composition of claim 8, wherein the at least one targeting/delivery moiety is selected from the group consisting of antibodies, ligands, tumor markers, aptamers, polyethylene glycol, albumin, tumor specific peptides, affibodies, vitamins, carbohydrates, hormones, low density lipoproteins (LDL), and combinations thereof.

10. The activatable composition of claim 1, wherein the at least one functional moiety is a therapeutic moiety and/or a detectable moiety.

11. The activatable composition of claim 1, further defined as comprising two or more functional moieties, wherein the two or more functional moieties are the same or are different.

12. A method of inhibiting and/or decreasing the occurrence and/or severity of at least one condition/disorder in a patient, the method comprising the steps of:
administering an effective amount of an activatable composition to the patient, the activatable composition comprising:
at least one functional moiety, wherein the functional moiety is a therapeutic moiety and/or a detectable moiety;
at least one singlet oxygen-labile linker selected from the group consisting of aminoacrylate, aminoacrylthioate, and aminoacrylamide, the at least one singlet oxygen-labile linker linked to the at least one functional moiety, wherein the at least one functional moiety is inactive until the at least one singlet oxygen-labile linker is cleaved by singlet oxygen, whereby the at least one functional moiety becomes activated; and
a sensitizer, which when exposed to an activator results in generation of singlet oxygen by the sensitizer; and
exposing at least a portion of the patient to the activator, whereby singlet oxygen is generated, resulting in cleavage of the at least one singlet oxygen-labile linker and activation of the at least one functional moiety.

13. The method of claim 12, wherein the activator is selected from the group consisting of irradiation with visible/near IR light, irradiation with ionizing radiation, exposure to electromagnetic waves/materials, exposure to luminescence, exposure to fluorescence, and combinations thereof.

14. The method of claim 12, wherein the activator comprises irradiation with light in a range of from about 380 nm to about 1200 nm.

15. The method of claim 12, wherein the activatable composition is further defined as comprising at least one of a prodrug, a nano-carrier, and a micro-carrier in which the at least one functional moiety is encapsulated, and wherein the at least one singlet oxygen-labile linker is incorporated into a portion of the structure of the at least one prodrug, nano-carrier, or micro-carrier, thereby indirectly linking the at least one functional moiety and the at least one singlet oxygen-labile linker to one another, and wherein at least one of:
(a) the nano-carrier is selected from the group consisting of liposomes, polymers, nanospheres, nanocapsules, micelles, solid lipid nanoparticles, and combinations thereof;
(b) the nano-carrier is further defined as being in the form of a dendrimer;
(c) the activatable composition comprises a prodrug, and the sensitizer is a photosensitizer; and
(d) the activatable composition comprises a prodrug which comprises a targeting group.

16. The method of claim 12, wherein the sensitizer of the activatable composition is a photosensitizer selected from the group consisting of porphyrin, phthalocyanines, boron-dipyrromethene (BODIPY) or aza-BODIPY-type photosensitizers, chlorins, bacteriochlorins, non-porphyrin-based photosensitizers, and combinations thereof.

17. The method of claim 12, further comprising a spacer between the at least one singlet oxygen-labile linker and the at least one functional moiety.

18. The method of claim 17, wherein the spacer is selected from the group consisting of piperidin-4-ylmethanol, pyrrolidine-2-carboxylic acid, pyrrolidine-3-carboxylic acid, piperidin-4-ylmethyl-2-bromoacetate, 1-(3-bromoporpyl)piperazine, and combinations thereof.

19. The method of claim 12, wherein the activatable composition further comprises at least one targeting/delivery moiety linked to the at least one functional moiety, wherein the targeting/delivery moiety is selected from the group consisting of antibodies, ligands, tumor markers, aptamers, polyethylene glycol, albumin, tumor specific peptides, affibodies, vitamins, carbohydrates, hormones, low density lipoproteins (LDL), and combinations thereof.

20. The method of claim 12, wherein the activatable composition is further defined as comprising two or more functional moieties, wherein the two or more functional moieties are the same or are different.

21. The method of claim 12, wherein:
the at least one functional moiety is a therapeutic moiety having at least one targeting/delivery moiety linked thereto;
at least one of the at least one singlet oxygen-labile linker, the at least one targeting/delivery moiety, and the sensitizer is further defined as comprising a detectable moiety; and
the method further comprises detecting the presence of the activatable composition at a desired delivery site.

\* \* \* \* \*

UNITED STATES PATENT AND TRADEMARK OFFICE
CERTIFICATE OF CORRECTION

PATENT NO. : 9,839,690 B2
APPLICATION NO. : 15/187227
DATED : December 12, 2017
INVENTOR(S) : Youngjae You et al.

It is certified that error appears in the above-identified patent and that said Letters Patent is hereby corrected as shown below:

In the Specification

Column 15, Line 24: After "density of the" delete "it" and replace with -- $\pi$ --
Column 21, Line 65: Delete "6.00 (s, 1H, HC(Cl)=C(O)) ppm;" and replace with -- 6.00 (s, 1H, HC(Cl)=C)O)) ppm; --
Column 32, Line 42: Delete "El ion" and replace with -- EI ion --
Column 57, Line 10: Delete "D2O)," and replace with -- $D_2O$), --
Column 57, Line 40: Delete "D20)," and replace with -- $D_2O$), --
Column 57, Line 52: Delete "D20)," and replace with -- $D_2O$), --
Column 57, Line 53: Delete "D20)," and replace with -- $D_2O$), --
Column 57, Line 64: Delete "D20)," and replace with -- $D_2O$), --
Column 59, Line 35: After "Cell viability was assessed by" delete "MIT" and replace with -- MTT --
Column 59, Line 37: After "mg/mL" delete "MIT" and replace with -- MTT --
Column 64, Line 24: After "MSD with" delete "El ion" and replace with -- EI ion --

Signed and Sealed this
Fifth Day of June, 2018

Andrei Iancu
*Director of the United States Patent and Trademark Office*

CERTIFICATE OF CORRECTION (continued)
U.S. Pat. No. 9,839,690 B2

Column 37 & 38, Line 1-25: Delete –continued diagram for Scheme 5 formula and replace with the following -continued Scheme 5 diagram formula.